(12) United States Patent
Lepak et al.

(10) Patent No.: US 10,736,693 B2
(45) Date of Patent: Aug. 11, 2020

(54) ENERGY DELIVERY DEVICES

(71) Applicant: Apama Medical, Inc., Campbell, CA (US)

(72) Inventors: Jonah Lepak, Santa Cruz, CA (US); Thomas McGrath, Santa Clara, CA (US); Michael Conroy, San Jose, CA (US); Casey Miller, Campbell, CA (US)

(73) Assignee: Apama Medical, Inc., Campbell, CA (US)

( * ) Notice: Subject to any disclaimer, the term of this patent is extended or adjusted under 35 U.S.C. 154(b) by 0 days.

(21) Appl. No.: 15/663,523

(22) Filed: Jul. 28, 2017

(65) Prior Publication Data

US 2017/0333125 A1  Nov. 23, 2017

Related U.S. Application Data

(63) Continuation of application No. PCT/US2016/062323, filed on Nov. 16, 2016.
(Continued)

(51) Int. Cl.
*A61B 18/14* (2006.01)
*A61B 1/00* (2006.01)
(Continued)

(52) U.S. Cl.
CPC ...... *A61B 18/1492* (2013.01); *A61B 1/00009* (2013.01); *A61B 1/00039* (2013.01); *A61B 1/00082* (2013.01); *A61B 1/00087* (2013.01); *A61B 1/00096* (2013.01); *A61B 1/00181* (2013.01); *A61B 1/015* (2013.01); *A61B 1/05* (2013.01); *A61B 1/0676* (2013.01); *A61B 1/0684* (2013.01); *A61B 5/0538* (2013.01); *A61B 5/4848* (2013.01); *A61B 34/20* (2016.02); *A61B 2018/0022* (2013.01);
(Continued)

(58) Field of Classification Search
CPC .................................................. A61B 18/0022
See application file for complete search history.

(56) References Cited

U.S. PATENT DOCUMENTS 4,448,188 A  5/1984 Loeb
4,547,193 A  10/1985 Rydell
(Continued)

FOREIGN PATENT DOCUMENTS

CN  1085416 A  4/1994
CN  1781161 A  5/2006
(Continued)

OTHER PUBLICATIONS

International Search Report and Written Opinion issued in PCT/US2016/062323, dated Apr. 5, 2017, 15 pages.
(Continued)

*Primary Examiner* — Michael F Peffley
*Assistant Examiner* — Bo Ouyang
(74) *Attorney, Agent, or Firm* — Faegre Drinker Biddle & Reath LLP

(57) ABSTRACT

Diagnostic and therapeutic medical devices and methods that include an elongate shaft, a balloon, a plurality of electrodes carried by the balloon, and electronics to electrically connect the electrodes to a proximal end of the shaft. The devices can include a visualization system within the balloon.

6 Claims, 43 Drawing Sheets

Related U.S. Application Data

(60) Provisional application No. 62/326,546, filed on Apr. 22, 2016, provisional application No. 62/309,359, filed on Mar. 16, 2016, provisional application No. 62/259,596, filed on Nov. 24, 2015, provisional application No. 62/255,895, filed on Nov. 16, 2015.

(51) Int. Cl.

| | | |
|---|---|---|
| *A61B 1/015* | (2006.01) | |
| *A61B 1/05* | (2006.01) | |
| *A61B 1/06* | (2006.01) | |
| *A61B 34/20* | (2016.01) | |
| *A61B 5/053* | (2006.01) | |
| *A61B 5/00* | (2006.01) | |
| *A61B 90/00* | (2016.01) | |
| *A61B 18/00* | (2006.01) | |

(52) U.S. Cl.
CPC ............ *A61B 2018/00023* (2013.01); *A61B 2018/00029* (2013.01); *A61B 2018/00255* (2013.01); *A61B 2018/00351* (2013.01); *A61B 2018/00577* (2013.01); *A61B 2018/00982* (2013.01); *A61B 2018/1465* (2013.01); *A61B 2018/1467* (2013.01); *A61B 2034/2048* (2016.02); *A61B 2090/065* (2016.02); *A61B 2218/002* (2013.01)

(56) References Cited

U.S. PATENT DOCUMENTS

| | | |
|---|---|---|
| 4,602,281 A | 7/1986 | Nagasaki et al. |
| 4,611,888 A | 9/1986 | Prenovitz et al. |
| 4,633,879 A | 1/1987 | Ong |
| 4,634,432 A | 1/1987 | Kocak |
| 4,638,207 A | 1/1987 | Radice |
| 4,646,721 A | 3/1987 | Arakawa |
| 4,692,139 A | 9/1987 | Stiles |
| 4,726,382 A | 2/1988 | Boehmer et al. |
| 4,739,766 A | 4/1988 | Riederer |
| 4,784,133 A | 11/1988 | Mackin |
| 4,809,680 A | 3/1989 | Yabe |
| 4,827,907 A | 5/1989 | Tashiro |
| 4,832,003 A | 5/1989 | Yabe |
| 4,843,275 A | 6/1989 | Radice |
| 4,890,623 A | 1/1990 | Cook et al. |
| 4,961,738 A | 10/1990 | Mackin |
| 4,968,306 A | 11/1990 | Huss et al. |
| 5,010,895 A | 4/1991 | Maurer et al. |
| 5,029,574 A | 7/1991 | Shimamura et al. |
| 5,041,089 A | 8/1991 | Mueller et al. |
| 5,069,674 A | 12/1991 | Fearnot et al. |
| 5,090,959 A | 2/1992 | Samson et al. |
| 5,109,861 A | 5/1992 | Walinsky et al. |
| 5,115,472 A | 5/1992 | Park et al. |
| 5,135,001 A | 8/1992 | Sinofsky et al. |
| 5,180,376 A | 1/1993 | Fischell |
| 5,187,572 A | 2/1993 | Nakamura et al. |
| 5,209,741 A | 5/1993 | Spaeth |
| 5,213,576 A | 5/1993 | Abiuso et al. |
| 5,228,442 A | 7/1993 | Imran |
| 5,233,416 A | 8/1993 | Inoue |
| 5,301,090 A | 4/1994 | Hed |
| 5,306,250 A | 4/1994 | March et al. |
| 5,309,910 A | 5/1994 | Edwards et al. |
| 5,311,866 A | 5/1994 | Kagan et al. |
| 5,325,847 A | 7/1994 | Matsuno |
| 5,343,860 A | 9/1994 | Metzger et al. |
| 5,377,682 A | 1/1995 | Ueno et al. |
| 5,385,148 A | 1/1995 | Lesh et al. |
| 5,391,200 A | 2/1995 | KenKnight et al. |
| 5,409,000 A | 4/1995 | Imran |
| 5,411,016 A | 5/1995 | Kume et al. |
| 5,430,475 A | 7/1995 | Goto et al. |
| 5,443,470 A | 8/1995 | Stern et al. |
| 5,494,483 A | 2/1996 | Adair |
| 5,505,730 A | 4/1996 | Edwards |
| 5,515,843 A | 5/1996 | Chang |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,241 A | 10/1996 | Edwards |
| 5,571,086 A | 11/1996 | Kaplan et al. |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,594,497 A | 1/1997 | Ahern et al. |
| 5,607,436 A | 3/1997 | Pratt et al. |
| 5,609,574 A | 3/1997 | Kaplan et al. |
| 5,609,606 A | 3/1997 | O'Boyle |
| 5,611,807 A | 3/1997 | O'Boyle |
| 5,626,564 A | 5/1997 | Zhan et al. |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,722,403 A | 3/1998 | McGee et al. |
| 5,735,846 A | 4/1998 | Panescu et al. |
| 5,769,846 A | 6/1998 | Edwards et al. |
| 5,769,880 A | 6/1998 | Truckai et al. |
| 5,779,698 A | 7/1998 | Clayman et al. |
| 5,795,325 A | 8/1998 | Valley et al. |
| 5,797,837 A | 8/1998 | Minami |
| 5,800,408 A | 9/1998 | Strauss et al. |
| 5,827,273 A | 10/1998 | Edwards |
| 5,830,213 A | 11/1998 | Panescu et al. |
| 5,836,874 A | 11/1998 | Swanson et al. |
| 5,846,196 A | 12/1998 | Siekmeyer et al. |
| 5,846,238 A | 12/1998 | Jackson et al. |
| 5,846,239 A | 12/1998 | Swanson et al. |
| 5,853,411 A | 12/1998 | Whayne et al. |
| 5,860,974 A | 1/1999 | Abele |
| 5,871,483 A | 2/1999 | Jackson et al. |
| 5,879,348 A | 3/1999 | Owens et al. |
| 5,881,727 A | 3/1999 | Edwards |
| 5,888,577 A | 3/1999 | Griffin, III et al. |
| 5,904,651 A | 5/1999 | Swanson et al. |
| 5,916,213 A | 6/1999 | Haissaguerre et al. |
| 5,935,075 A | 8/1999 | Casscells et al. |
| 5,938,660 A | 8/1999 | Swartz et al. |
| 5,940,126 A | 8/1999 | Kimura |
| 5,957,950 A | 9/1999 | Mockros et al. |
| 5,961,513 A | 10/1999 | Swanson et al. |
| 5,967,986 A | 10/1999 | Cimochowski et al. |
| 5,984,860 A | 11/1999 | Shan |
| 5,991,650 A | 11/1999 | Swanson et al. |
| 5,997,571 A | 12/1999 | Farr et al. |
| 6,004,269 A | 12/1999 | Crowley et al. |
| 6,006,119 A | 12/1999 | Soller et al. |
| 6,012,457 A | 1/2000 | Lesh |
| 6,024,740 A | 2/2000 | Lesh et al. |
| 6,052,607 A | 4/2000 | Edwards et al. |
| 6,071,302 A | 6/2000 | Sinofsky et al. |
| 6,102,905 A | 8/2000 | Baxter et al. |
| 6,117,101 A | 9/2000 | Diederich et al. |
| 6,123,718 A | 9/2000 | Tu et al. |
| 6,124,883 A | 9/2000 | Suzuki et al. |
| 6,134,463 A | 10/2000 | Wittkampf et al. |
| 6,142,993 A | 11/2000 | Whayne et al. |
| 6,159,203 A | 12/2000 | Sinofsky |
| 6,163,726 A | 12/2000 | Wolf |
| 6,164,283 A | 12/2000 | Lesh |
| 6,168,591 B1 | 1/2001 | Sinofsky |
| 6,178,346 B1 | 1/2001 | Amundson et al. |
| 6,205,361 B1 | 3/2001 | Kuzma et al. |
| 6,206,912 B1 | 3/2001 | Goldsteen et al. |
| 6,215,231 B1 | 4/2001 | Newnham et al. |
| 6,231,516 B1 | 5/2001 | Keilman et al. |
| 6,233,491 B1 | 5/2001 | Kordis et al. |
| 6,258,087 B1 | 7/2001 | Edwards et al. |

(56) References Cited

U.S. PATENT DOCUMENTS

| | | |
|---|---|---|
| 6,270,492 B1 | 8/2001 | Sinofsky |
| 6,292,689 B1 | 9/2001 | Wallace et al. |
| 6,315,712 B1 | 11/2001 | Rovegno |
| 6,375,654 B1 | 4/2002 | McIntyre |
| 6,384,915 B1 | 5/2002 | Everett et al. |
| 6,391,024 B1 | 5/2002 | Sun et al. |
| 6,402,746 B1 | 6/2002 | Whayne et al. |
| 6,416,463 B1 | 7/2002 | Tsuzuki et al. |
| 6,425,877 B1 | 7/2002 | Edwards |
| 6,460,545 B2 | 10/2002 | Kordis |
| 6,485,414 B1 | 11/2002 | Neuberger |
| 6,500,174 B1 | 12/2002 | Maguire et al. |
| 6,511,478 B1 | 1/2003 | Burnside et al. |
| 6,514,249 B1 | 2/2003 | Maguire et al. |
| 6,517,534 B1 | 2/2003 | McGovern et al. |
| 6,527,769 B2 | 3/2003 | Langberg et al. |
| 6,558,375 B2 | 5/2003 | Sinofsky et al. |
| 6,558,378 B2 | 5/2003 | Sherman et al. |
| 6,572,609 B1 | 6/2003 | Farr et al. |
| 6,572,612 B2 | 6/2003 | Stewart et al. |
| 6,579,285 B2 | 6/2003 | Sinofsky |
| 6,595,989 B1 | 7/2003 | Schaer |
| 6,599,288 B2 | 7/2003 | Maguire et al. |
| 6,605,055 B1 | 8/2003 | Sinofsky et al. |
| 6,605,084 B2 | 8/2003 | Acker et al. |
| 6,607,502 B1 | 8/2003 | Maguire et al. |
| 6,635,027 B1 | 10/2003 | Cragg et al. |
| 6,635,054 B2 | 10/2003 | Fjield et al. |
| 6,641,553 B1 | 11/2003 | Chee et al. |
| 6,652,515 B1 | 11/2003 | Maguire et al. |
| 6,659,940 B2 | 12/2003 | Adler |
| 6,659,953 B1 | 12/2003 | Smanaweera et al. |
| 6,660,002 B1 | 12/2003 | Edwards et al. |
| 6,676,656 B2 | 1/2004 | Sinofsky |
| 6,692,430 B2 | 2/2004 | Adler |
| 6,692,431 B2 | 2/2004 | Kazakevich |
| 6,692,455 B2 | 2/2004 | Goode et al. |
| 6,692,461 B2 | 2/2004 | Wantink |
| 6,692,462 B2 | 2/2004 | Mackenzie et al. |
| 6,692,463 B1 | 2/2004 | Marteau et al. |
| 6,692,464 B2 | 2/2004 | Graf |
| 6,692,490 B1 | 2/2004 | Edwards |
| 6,702,782 B2 | 3/2004 | Miller et al. |
| 6,736,811 B2 | 5/2004 | Panescu et al. |
| 6,743,226 B2 | 6/2004 | Cosman et al. |
| 6,752,805 B2 | 6/2004 | Maguire et al. |
| 6,771,996 B2 | 8/2004 | Bowe et al. |
| 6,780,183 B2 | 8/2004 | Jimenez, Jr. et al. |
| 6,808,524 B2 | 10/2004 | Lopath et al. |
| 6,814,730 B2 | 11/2004 | Li |
| 6,869,431 B2 | 3/2005 | Maguire et al. |
| 6,872,183 B2 | 3/2005 | Sampson et al. |
| 6,872,206 B2 | 3/2005 | Edwards et al. |
| 6,887,235 B2 | 5/2005 | O'Connor et al. |
| 6,911,027 B1 | 6/2005 | Edwards et al. |
| 6,932,809 B2 | 8/2005 | Sinofsky |
| 6,937,899 B2 | 8/2005 | Sheldon et al. |
| 6,942,657 B2 | 9/2005 | Sinofsky et al. |
| 6,949,072 B2 | 9/2005 | Furnish et al. |
| 6,955,173 B2 | 10/2005 | Lesh |
| 6,976,956 B2 | 12/2005 | Takahashi et al. |
| 6,978,174 B2 | 12/2005 | Gelfand et al. |
| 7,004,923 B2 | 2/2006 | Deniega et al. |
| 7,030,904 B2 | 4/2006 | Adair et al. |
| 7,048,733 B2 | 5/2006 | Hartley et al. |
| 7,115,122 B1 | 10/2006 | Swanson et al. |
| 7,137,395 B2 | 11/2006 | Fried et al. |
| 7,150,745 B2 | 12/2006 | Stern et al. |
| 7,162,303 B2 | 1/2007 | Levin et al. |
| 7,166,075 B2 | 1/2007 | Varghese et al. |
| 7,169,140 B1 | 1/2007 | Kume |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,267,674 B2 | 9/2007 | Brucker et al. |
| 7,285,116 B2 | 10/2007 | de la Rama et al. |
| 7,286,866 B2 | 10/2007 | Okerlund et al. |
| 7,291,146 B2 * | 11/2007 | Steinke .......... A61B 18/1492 606/41 |
| 7,293,562 B2 | 11/2007 | Malecki et al. |
| 7,300,397 B2 | 11/2007 | Adler et al. |
| 7,310,150 B2 | 12/2007 | Guillermo et al. |
| 7,320,677 B2 | 1/2008 | Brouillette |
| 7,344,533 B2 | 3/2008 | Pearson et al. |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,367,975 B2 | 5/2008 | Maiecki et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,427,265 B1 | 9/2008 | Keilman et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,517,346 B2 | 4/2009 | Sloan et al. |
| 7,519,096 B2 | 4/2009 | Bouma et al. |
| 7,529,393 B2 | 5/2009 | Peszynski et al. |
| 7,534,204 B2 | 5/2009 | Starksen et al. |
| 7,538,859 B2 | 5/2009 | Tearney et al. |
| 7,585,273 B2 | 9/2009 | Adler et al. |
| 7,588,535 B2 | 9/2009 | Adler et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,683,323 B2 | 3/2010 | Kymissis |
| 7,756,583 B2 | 7/2010 | Demarais et al. |
| 7,758,499 B2 | 7/2010 | Adler |
| 7,853,333 B2 | 12/2010 | Demarais |
| 7,879,029 B2 | 2/2011 | Jimenez |
| 7,928,113 B2 | 4/2011 | Neamati et al. |
| 7,935,108 B2 | 5/2011 | Baxter et al. |
| 7,937,143 B2 | 5/2011 | Demarais et al. |
| 7,951,144 B2 * | 5/2011 | Mahajan .................. A61B 5/01 374/10 |
| 8,007,440 B2 | 8/2011 | Magnin et al. |
| 8,025,661 B2 | 9/2011 | Arnold et al. |
| 8,078,266 B2 | 12/2011 | Saadat et al. |
| 8,167,805 B2 | 5/2012 | Emery et al. |
| 8,172,747 B2 | 5/2012 | Wallace et al. |
| 8,194,121 B2 | 6/2012 | Blumzvig et al. |
| 8,295,902 B2 | 10/2012 | Salahieh et al. |
| 8,323,241 B2 | 12/2012 | Salahieh et al. |
| 8,333,012 B2 | 12/2012 | Rothe et al. |
| 8,337,492 B2 | 12/2012 | Kunis et al. |
| 8,361,041 B2 | 1/2013 | Fang et al. |
| 8,369,921 B2 | 2/2013 | Tegg et al. |
| 8,417,321 B2 | 4/2013 | Saadat et al. |
| 8,419,613 B2 | 4/2013 | Saadat et al. |
| 8,465,421 B2 | 6/2013 | Finkman et al. |
| 8,479,585 B2 | 7/2013 | Shaw-Klein |
| 8,540,704 B2 | 9/2013 | Melsky et al. |
| 8,560,086 B2 | 10/2013 | Just et al. |
| 8,617,150 B2 | 12/2013 | Tsoref et al. |
| 8,702,682 B2 | 4/2014 | Atanasoska et al. |
| 8,708,953 B2 | 4/2014 | Salahieh et al. |
| 8,728,073 B2 | 5/2014 | McDaniel |
| 8,777,857 B2 | 7/2014 | Sliwa et al. |

(56) References Cited

U.S. PATENT DOCUMENTS

| | | |
|---|---|---|
| 8,805,466 B2 | 8/2014 | Salahieh et al. |
| 8,808,281 B2 | 8/2014 | Emmons et al. |
| 8,840,601 B2 | 9/2014 | Salahieh et al. |
| 8,894,643 B2 | 11/2014 | Watson et al. |
| 8,920,369 B2 | 12/2014 | Salahieh et al. |
| 8,939,970 B2 | 1/2015 | Stone et al. |
| 8,968,591 B2 | 3/2015 | Nishikubo et al. |
| 8,981,625 B2 | 3/2015 | Nishikubo et al. |
| 9,037,259 B2 | 5/2015 | Mathur |
| 9,174,050 B2 | 11/2015 | Mathur et al. |
| 9,333,031 B2 | 5/2016 | Salahieh et al. |
| 9,445,862 B2 | 9/2016 | Brewster et al. |
| 9,586,025 B2 | 3/2017 | Salahieh et al. |
| 9,610,006 B2 | 4/2017 | Salahieh et al. |
| 9,655,677 B2 | 5/2017 | Salahieh et al. |
| 9,717,557 B2 | 8/2017 | Salahieh et al. |
| 2002/0002384 A1 | 1/2002 | Gilson et al. |
| 2002/0068934 A1 | 6/2002 | Edwards et al. |
| 2002/0087208 A1 | 7/2002 | Koblish et al. |
| 2002/0095147 A1 | 7/2002 | Shadduck |
| 2002/0111548 A1 | 8/2002 | Swanson et al. |
| 2002/0154215 A1 | 10/2002 | Schechterman et al. |
| 2002/0165535 A1 | 11/2002 | Lesh et al. |
| 2002/0183623 A1 | 12/2002 | Tang et al. |
| 2003/0050637 A1 | 3/2003 | Maguire et al. |
| 2003/0065371 A1 | 4/2003 | Satake |
| 2003/0097121 A1 | 5/2003 | Jolly et al. |
| 2003/0097129 A1 | 5/2003 | Davison et al. |
| 2003/0135101 A1 | 7/2003 | Webler |
| 2003/0233099 A1 | 12/2003 | Danaek et al. |
| 2003/0236443 A1 | 12/2003 | Cespedes et al. |
| 2004/0054363 A1 | 3/2004 | Vaska et al. |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0167503 A1 | 8/2004 | Sinofsky |
| 2004/0243118 A1 | 12/2004 | Ayers et al. |
| 2005/0004440 A1 | 1/2005 | Vanney |
| 2005/0065504 A1 | 3/2005 | Melsky et al. |
| 2005/0171527 A1 | 8/2005 | Bhola |
| 2005/0203597 A1 | 9/2005 | Yamazaki et al. |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2005/0245892 A1 | 11/2005 | Elkins et al. |
| 2006/0041277 A1 | 2/2006 | Deem et al. |
| 2006/0089632 A1 | 4/2006 | Barthe et al. |
| 2006/0100618 A1 | 5/2006 | Chan et al. |
| 2006/0173300 A1 | 8/2006 | Oslund et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0241589 A1 | 10/2006 | Heim et al. |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0032727 A1 | 2/2007 | Omata |
| 2007/0073135 A1 | 3/2007 | Lee et al. |
| 2007/0078507 A1 | 4/2007 | Zacouto |
| 2007/0112422 A1 | 5/2007 | Dehdashtian |
| 2007/0118094 A1 | 5/2007 | Bingham et al. |
| 2007/0129720 A1 | 6/2007 | Demarais et al. |
| 2007/0129760 A1 | 6/2007 | Demarais et al. |
| 2007/0135875 A1 | 6/2007 | Demarais et al. |
| 2007/0213616 A1 | 9/2007 | Anderson et al. |
| 2007/0213671 A1 | 9/2007 | Hiatt |
| 2007/0219451 A1 | 9/2007 | Kula et al. |
| 2007/0225634 A1 | 9/2007 | Ferren et al. |
| 2007/0233185 A1 | 10/2007 | Anderson et al. |
| 2007/0244501 A1 | 10/2007 | Horn et al. |
| 2007/0255097 A1 | 11/2007 | Jung et al. |
| 2007/0270686 A1 | 11/2007 | Ritter et al. |
| 2007/0287994 A1 | 12/2007 | Patel |
| 2008/0004652 A1 | 1/2008 | Abboud et al. |
| 2008/0058590 A1 | 3/2008 | Saadat et al. |
| 2008/0058591 A1 | 3/2008 | Saadat et al. |
| 2008/0058836 A1 | 3/2008 | Moll et al. |
| 2008/0071173 A1 | 3/2008 | Aldrich |
| 2008/0108867 A1 | 5/2008 | Zhou |
| 2008/0125772 A1 | 5/2008 | Stone et al. |
| 2008/0188912 A1 | 8/2008 | Stone et al. |
| 2008/0205481 A1 | 8/2008 | Faries, Jr. et al. |
| 2008/0262489 A1 | 10/2008 | Steinke |
| 2008/0275300 A1 | 11/2008 | Rothe et al. |
| 2008/0275445 A1 | 11/2008 | Kelly et al. |
| 2008/0281293 A1 | 11/2008 | Peh et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0030276 A1 | 1/2009 | Saadat et al. |
| 2009/0030412 A1 | 1/2009 | Willis et al. |
| 2009/0046171 A1 | 2/2009 | Kogan |
| 2009/0051763 A1 | 2/2009 | Adler et al. |
| 2009/0054786 A1 | 2/2009 | Beckermus |
| 2009/0054787 A1 | 2/2009 | Adler et al. |
| 2009/0054803 A1 | 2/2009 | Saadat et al. |
| 2009/0076498 A1 | 3/2009 | Saadat et al. |
| 2009/0125022 A1 | 5/2009 | Saadat et al. |
| 2009/0137893 A1 | 5/2009 | Seibel et al. |
| 2009/0203962 A1 | 8/2009 | Miller et al. |
| 2009/0227885 A1 | 9/2009 | Lowery et al. |
| 2009/0227999 A1 | 9/2009 | Willis et al. |
| 2009/0240249 A1 | 9/2009 | Chan et al. |
| 2009/0247933 A1 | 10/2009 | Maor et al. |
| 2009/0254142 A1 | 10/2009 | Edwards et al. |
| 2009/0275799 A1 | 11/2009 | Saadat et al. |
| 2009/0299354 A1 | 12/2009 | Melsky et al. |
| 2009/0312754 A1 | 12/2009 | Lenihan et al. |
| 2009/0318757 A1 | 12/2009 | Singh |
| 2009/0318759 A1 | 12/2009 | Jacobsen et al. |
| 2009/0326320 A1 | 12/2009 | Sinofsky et al. |
| 2009/0326321 A1 | 12/2009 | Jacobsen et al. |
| 2009/0326572 A1 | 12/2009 | Peh et al. |
| 2010/0016957 A1 | 1/2010 | Jager et al. |
| 2010/0087782 A1 | 4/2010 | Ghaffari et al. |
| 2010/0121142 A1 | 5/2010 | Ouyang et al. |
| 2010/0204560 A1 | 8/2010 | Salahieh et al. |
| 2010/0204561 A1 | 8/2010 | Saadat et al. |
| 2010/0238279 A1 | 9/2010 | Thoms et al. |
| 2011/0034790 A1 | 2/2011 | Mourlas et al. |
| 2011/0034912 A1 | 2/2011 | de Graff et al. |
| 2011/0040172 A1 | 2/2011 | Carpentier et al. |
| 2011/0046600 A1 | 2/2011 | Crank |
| 2011/0077579 A1 | 3/2011 | Harrison et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0152352 A1 | 6/2011 | Hata et al. |
| 2011/0160514 A1 | 6/2011 | Long et al. |
| 2011/0160584 A1 | 6/2011 | Paul et al. |
| 2011/0201973 A1 | 8/2011 | Stephens et al. |
| 2011/0237940 A1 | 9/2011 | Raleigh |
| 2011/0257523 A1 | 10/2011 | Hastings et al. |
| 2011/0292258 A1 | 12/2011 | Adler et al. |
| 2011/0301418 A1 | 12/2011 | Gharib et al. |
| 2011/0319752 A1 | 12/2011 | Steinberg et al. |
| 2012/0004529 A1 | 1/2012 | Tolkowsky et al. |
| 2012/0004537 A1 | 1/2012 | Tolkowsky et al. |
| 2012/0069367 A1 | 3/2012 | Iguchi |
| 2012/0071870 A1* | 3/2012 | Salahieh ............... A61B 5/01 606/33 |
| 2012/0116438 A1 | 5/2012 | Salahieh et al. |
| 2012/0130171 A1 | 5/2012 | Barak et al. |
| 2012/0165669 A1 | 6/2012 | Barley et al. |
| 2012/0302877 A1 | 11/2012 | Harks et al. |
| 2013/0079645 A1 | 3/2013 | Amirana et al. |
| 2013/0085493 A1 | 4/2013 | Bloom et al. |
| 2013/0137920 A1 | 5/2013 | Schaeffer et al. |
| 2013/0138082 A1 | 5/2013 | Salahieh et al. |
| 2013/0172726 A9 | 7/2013 | Saadat et al. |

(56) References Cited

U.S. PATENT DOCUMENTS

| | | |
|---|---|---|
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0204125 A1 | 8/2013 | Chang et al. |
| 2013/0204126 A1 | 8/2013 | Namati et al. |
| 2013/0231533 A1 | 9/2013 | Papademetriou et al. |
| 2013/0289350 A1 | 10/2013 | Lerner et al. |
| 2013/0304065 A1 | 11/2013 | Lopes et al. |
| 2013/0317497 A1 | 11/2013 | Edwards et al. |
| 2014/0031810 A1 | 1/2014 | Mahvi et al. |
| 2014/0058197 A1 | 2/2014 | Salahieh et al. |
| 2014/0107623 A1 | 4/2014 | Salahieh et al. |
| 2014/0121470 A1 | 5/2014 | Scharf et al. |
| 2014/0171942 A1 | 6/2014 | Werneth et al. |
| 2014/0180273 A1 | 6/2014 | Nair |
| 2014/0213850 A1 | 7/2014 | Levy et al. |
| 2014/0243680 A1 | 8/2014 | Raleigh |
| 2014/0296643 A1 | 10/2014 | Levy et al. |
| 2014/0296866 A1 | 10/2014 | Salman et al. |
| 2014/0309495 A1 | 10/2014 | Kirma et al. |
| 2014/0316198 A1 | 10/2014 | Krivopisk et al. |
| 2014/0320617 A1 | 10/2014 | Parks et al. |
| 2014/0333743 A1 | 11/2014 | Gilreath et al. |
| 2014/0357956 A1 | 12/2014 | Arnr Saiahieh et al. |
| 2014/0358140 A1 | 12/2014 | Emmons et al. |
| 2014/0364691 A1 | 12/2014 | Krivopisk et al. |
| 2014/0364692 A1 | 12/2014 | Salman et al. |
| 2014/0364694 A1 | 12/2014 | Avron et al. |
| 2014/0370072 A1 | 12/2014 | Hossainy et al. |
| 2015/0073341 A1 | 3/2015 | Salahieh et al. |
| 2015/0094656 A1 | 4/2015 | Salahieh et al. |
| 2015/0327753 A1 | 11/2015 | Amirana et al. |
| 2015/0351836 A1 | 12/2015 | Prutchi |
| 2016/0000500 A1 | 1/2016 | Salahieh et al. |
| 2016/0051321 A1 | 2/2016 | Salahieh et al. |
| 2016/0157954 A1 | 6/2016 | Sagon et al. |
| 2016/0345947 A1 | 12/2016 | Salahieh et al. |
| 2017/0027601 A1 | 2/2017 | Salahieh et al. |
| 2017/0042614 A1 | 2/2017 | Salahieh et al. |
| 2017/0042615 A1 | 2/2017 | Salahieh et al. |
| 2017/0080184 A1 | 3/2017 | Salahieh et al. |
| 2017/0080186 A1 | 3/2017 | Salahieh et al. |
| 2017/0143201 A1 | 5/2017 | Claude et al. |
| 2017/0173303 A1 | 6/2017 | Salahieh et al. |
| 2017/0203077 A1 | 7/2017 | Salahieh et al. |

FOREIGN PATENT DOCUMENTS

| | | |
|---|---|---|
| CN | 101511292 A | 8/2009 |
| CN | 101888813 A | 11/2010 |
| CN | 101956919 A | 1/2011 |
| DE | 4104092 A1 | 8/1991 |
| EP | 0322852 A1 | 7/1989 |
| EP | 0802768 A | 10/1997 |
| EP | 0637943 B1 | 4/1998 |
| EP | 623360 B1 | 3/1999 |
| EP | 0723467 B1 | 4/2002 |
| EP | 0693955 B1 | 1/2003 |
| EP | 1382366 A1 | 1/2004 |
| EP | 1463441 A2 | 10/2004 |
| EP | 1604613 A1 | 12/2005 |
| EP | 1991301 A2 | 11/2008 |
| EP | 2335757 A2 | 6/2011 |
| JP | 08504333 A | 5/1996 |
| JP | 2000504242 A | 4/2000 |
| JP | 2003510126 A | 3/2003 |
| JP | 2004237077 A | 8/2004 |
| JP | 2008142346 A | 6/2006 |
| JP | 2007516010 A | 6/2007 |
| JP | 2009507617 A | 2/2009 |
| JP | 2009539575 A | 11/2009 |
| JP | 2010507404 A | 3/2010 |
| JP | 2012525898 A | 10/2012 |
| WO | WO87/05748 A1 | 9/1987 |
| WO | WO95/05775 A1 | 3/1995 |
| WO | WO95/10319 A1 | 4/1995 |
| WO | WO98/31271 A2 | 7/1998 |
| WO | WO99/00060 A1 | 1/1999 |
| WO | WO99/02096 A1 | 1/1999 |
| WO | WO99/26530 A1 | 6/1999 |
| WO | WO99/42176 A1 | 8/1999 |
| WO | WO99/44519 A2 | 9/1999 |
| WO | WO99/45855 A1 | 9/1999 |
| WO | WO00/38580 A1 | 7/2000 |
| WO | WO00/56237 A2 | 9/2000 |
| WO | WO00/66014 A1 | 11/2000 |
| WO | WO00/67648 A1 | 11/2000 |
| WO | WO00/67656 A1 | 11/2000 |
| WO | WO01/08575 A2 | 2/2001 |
| WO | WO01/08576 A2 | 2/2001 |
| WO | WO01/13812 A1 | 3/2001 |
| WO | WO01/68178 A1 | 9/2001 |
| WO | WO01/72373 A2 | 10/2001 |
| WO | WO01/87169 A1 | 11/2001 |
| WO | WO01/87174 A1 | 11/2001 |
| WO | WO01/95820 A1 | 12/2001 |
| WO | WO02/40089 A2 | 5/2002 |
| WO | WO03/013624 A2 | 2/2003 |
| WO | WO2005/032370 A1 | 4/2005 |
| WO | WO2005/065563 A1 | 7/2005 |
| WO | WO2006/077573 A1 | 7/2006 |
| WO | WO2007/001981 A2 | 1/2007 |
| WO | WO2007/047993 A2 | 4/2007 |
| WO | WO2007/059195 A1 | 5/2007 |
| WO | WO2008/061152 A2 | 5/2008 |
| WO | WO2009/067695 A1 | 5/2009 |
| WO | WO2009/088678 A1 | 7/2009 |
| WO | WO2009/132137 A1 | 10/2009 |
| WO | WO2009/151600 A2 | 12/2009 |
| WO | WO2009/155441 A2 | 12/2009 |
| WO | 2011143468 A3 | 11/2011 |
| WO | WO2011/153434 A2 | 12/2011 |
| WO | WO2012/033837 A2 | 3/2012 |
| WO | WO2013/049601 A2 | 4/2013 |
| WO | WO2013/098732 A1 | 7/2013 |
| WO | WO2014/100259 A1 | 6/2014 |

OTHER PUBLICATIONS

Denham et al.; Ultrasonic resonant modes of piezoelectric balloons under internal pressure; J. Acoust. Soc. Am.; 132(3); pp. 1368-1377; Sep. 2012.

Drafts, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

Foley et al.; Computer Graphics Principles and Practice; 2nd Edition; Addison Wesley (publisher); pp. 835-843; Jun. 1990.

Gibson; Visualization of lesion transmurality and depth of necrosis using an ablation catheter that incorporates ultrasound imaging: a small step or a major leap forward on the road to a more durable catheter ablation procedure for treatment of atrial fibrillation; Heart Rhythm; 8(2); pp. 313-314; Feb. 2011.

Hu et al.; In-vivo pan/tilt endoscope with integrated light source; Intelligent Robots and Systems; IROS 2007. IEEE/RSJ International Conference on; pp. 1284-1289; San Diego, CA, USA: Oct. 29-Nov. 2, 2007.

Wippermann et al.; Low cost video endoscopes with simplified integration; In SPIE Photonics Europe; International Society for Optics and Phtonics; vol. 7716; pp. 77160M-1-77160M-9; Apr. 30, 2010.

Wright et al.; Real-time lesion assessment using a novel combined ultrasound and radiofrequency ablation catheter; Heart Rhythm; 8(2); pp. 304-312; Feb. 2011.

Wu et al.; Transmural ultrasound imaging of thermal lesion and action potential changes in perfused canine cardiac wedge preparations by high intensity focused ultrasound ablation; Plos One; 8(12); pp. 1-13; Dec. 2013.

Salahieh et al.; U.S. Appl. No. 13/830,624 entitled "Local Sympathectomy for PVD," filed Mar. 14, 2013.

(56) References Cited

OTHER PUBLICATIONS

Salahieh et al.; U.S. Appl. No. 61/622,495 entitled "Energy Delivery Device with Rapid Exchange Features," filed Apr. 10, 2012.
Salahieh et al.; U.S. Appl. No. 61/624,206 entitled "Energy delivery device and methods of use," filed Apr. 13, 2012.
Salahieh et al.; U.S. Appl. No. 15/640,306 entitled "Ablation catheters," filed Jun. 30, 2017.
Extended European Search Report issued in EP Application 15811644.2, dated Dec. 12, 2017, 8 pages.
Extended European Search Report issued in EP Application 14782484.1, dated Oct. 31, 2016, 9 pages.
International Preliminary Report on Patentability issued in PCT/US2014/033393, dated Oct. 13, 2015, 11 pages.
International Preliminary Report on Patentability issued in PCT/US2016/039646, dated Jan. 4, 2018, 6 pages.
International Preliminary Report on Patentability issued in PCT/US2016/062323, dated May 31, 2018, 10 pages.
International Search Report issued in PCT/US2014033393, dated Aug. 19, 2014, 5 pages.
Salahieh et al., U.S. Appl. No. 15/375,027, entilted "Steerable medical devices, systems, and methods of use," filed Dec. 9, 2016.
Salahieh et al., U.S. Appl. No. 15/082,923 entitled "Steerable Medical Devices, Systems, and Methods of Use," filed Mar. 28, 2016.
Salahieh et al., U.S. Appl. No. 15/092,442 entitled "Intravascular Tissue Disruption," filed Apr. 6, 2016.
Salahieh et al., U.S. Appl. No. 15/138,050 entitled "Steerable Medical Devices, Systems, and Methods of Use," filed Apr. 25, 2016.
Salahieh et al., U.S. Appl. No. 15/167,509 entitled "Intravascular Tissue Disruption," filed May 27, 2016.
Salahieh et al., U.S. Appl. No. 15/339,724 entitled "Ablation Catheters," filed Oct. 31, 2016.
Salahieh et al., U.S. Appl. No. 15/339,745 entitled "Ablation catheters," filed Oct. 31, 2016.
Salahieh et al., U.S. Appl. No. 15/452,413 entitled "Steerable delivery sheaths," filed Mar. 7, 2017.
Tymecki et al., "Strip thick-film silver ion-selective electrodes", Sensors and Actuators B; 96(3); pp. 482-488, Dec. 1, 2003.

* cited by examiner

Fig. 27

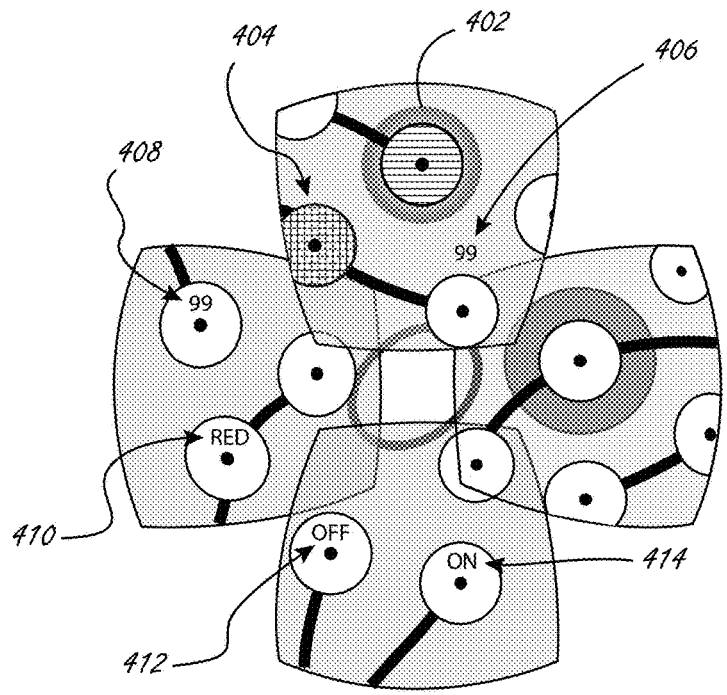
Fig. 29
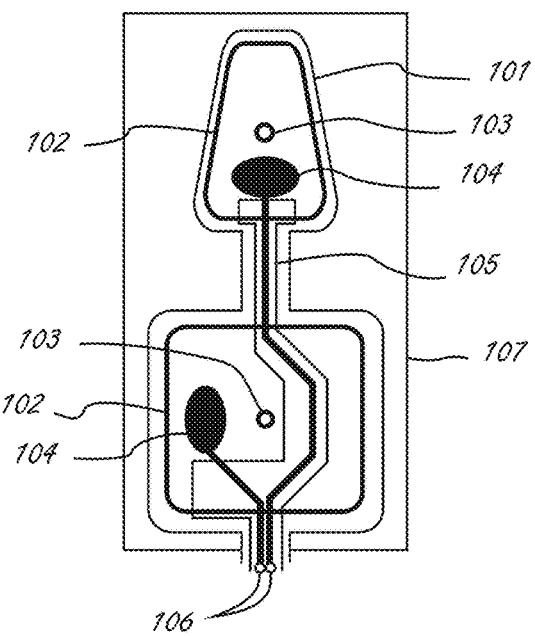
Fig. 30
Fig. 31
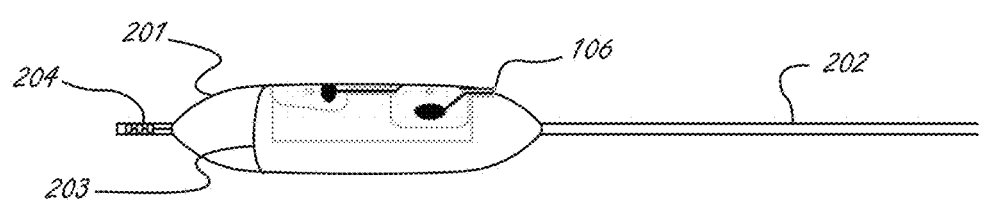

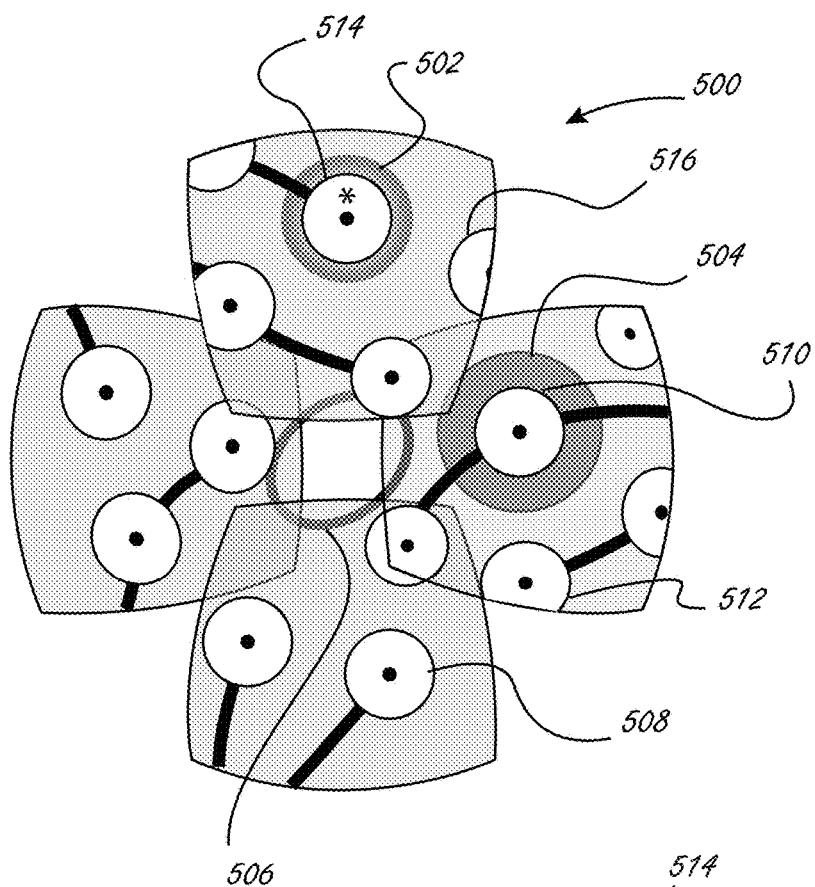
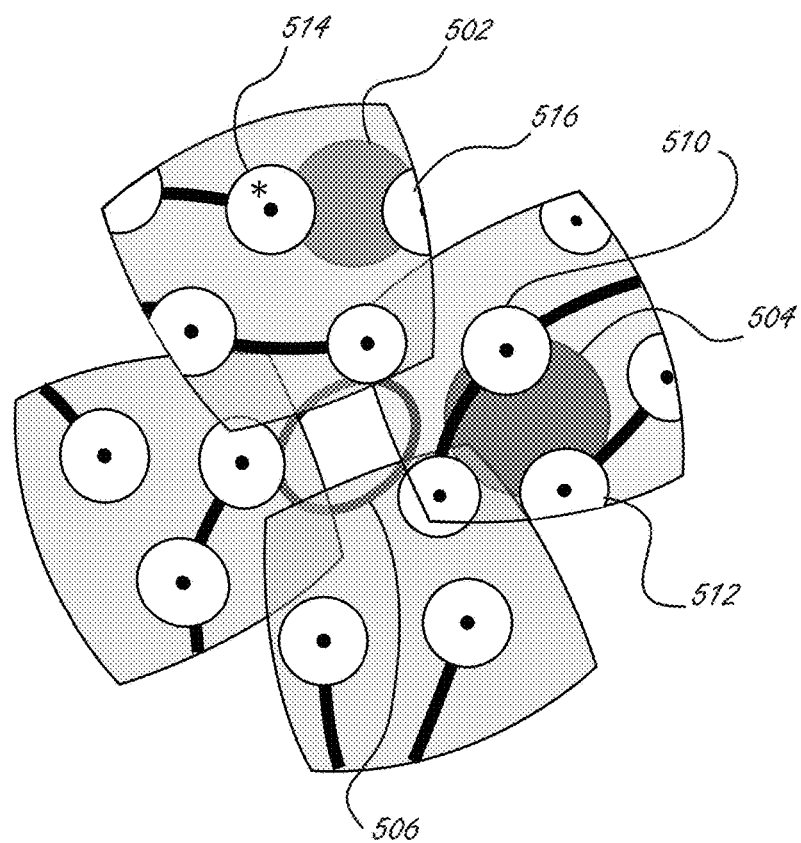
Fig. 32A
Fig. 32B

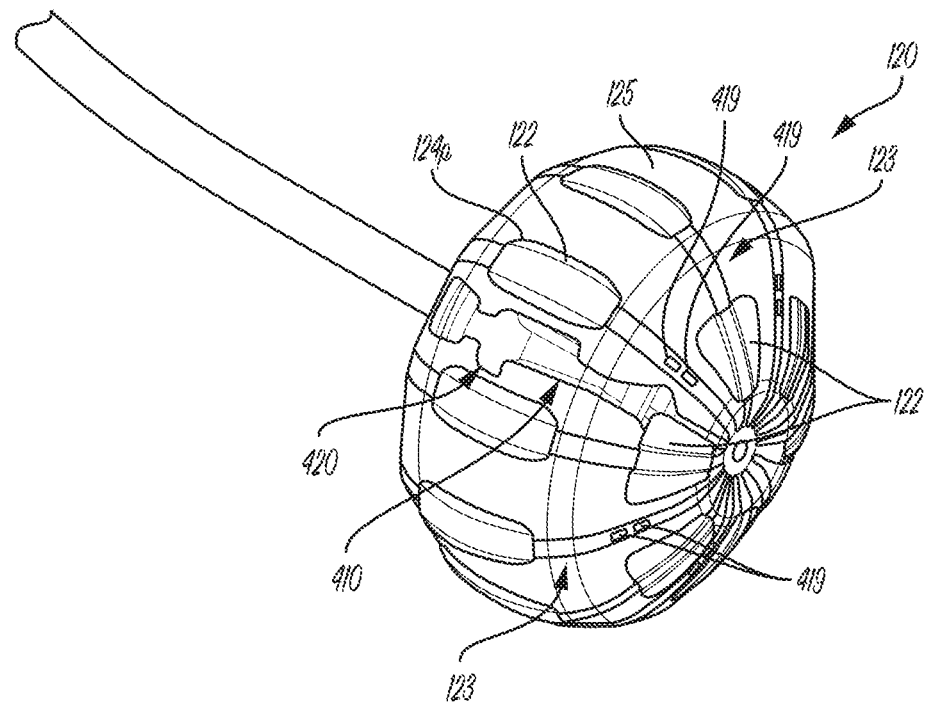
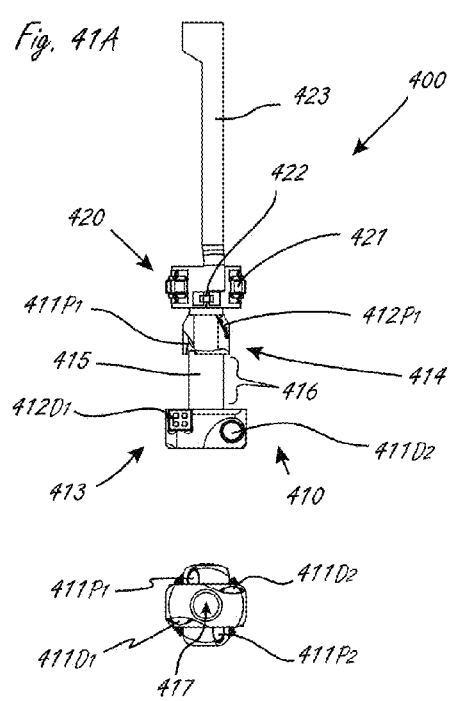
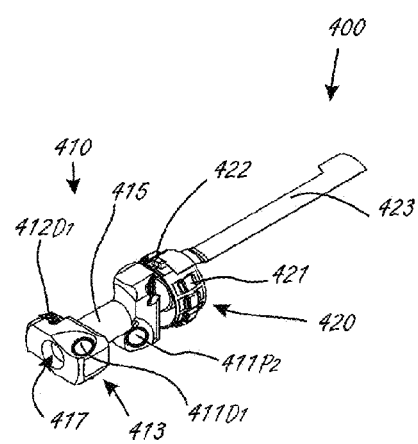
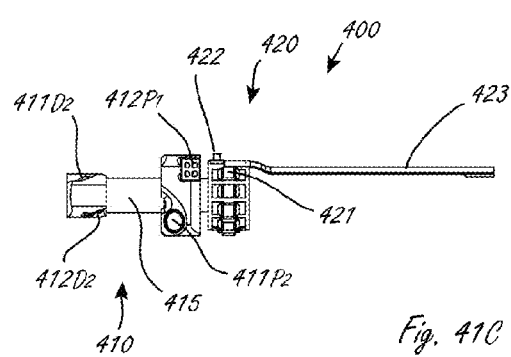

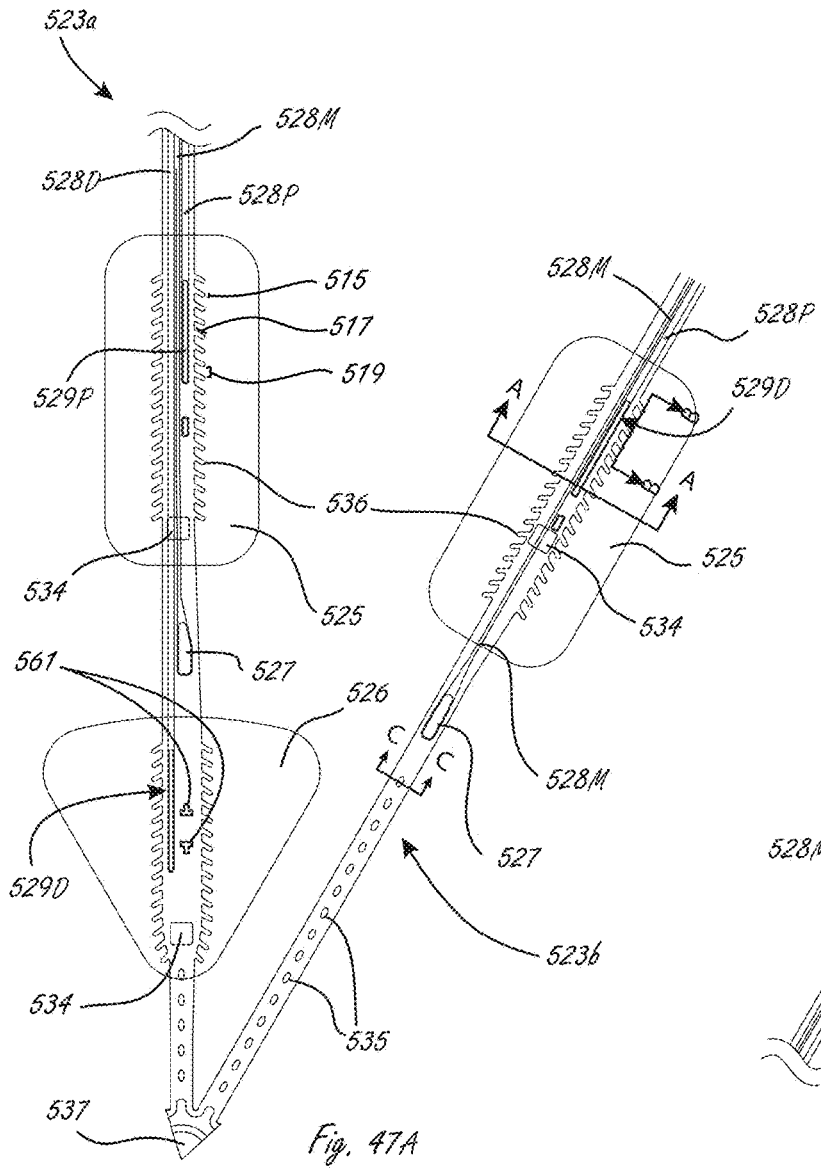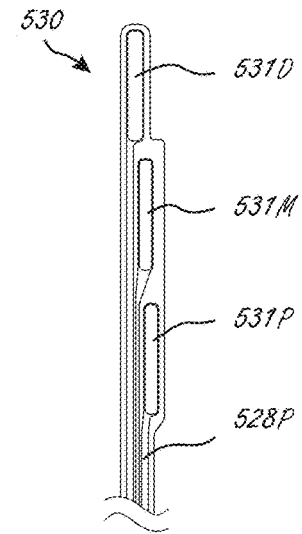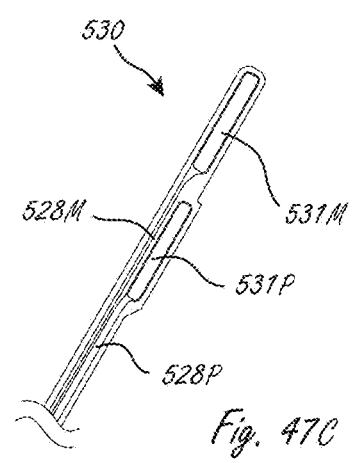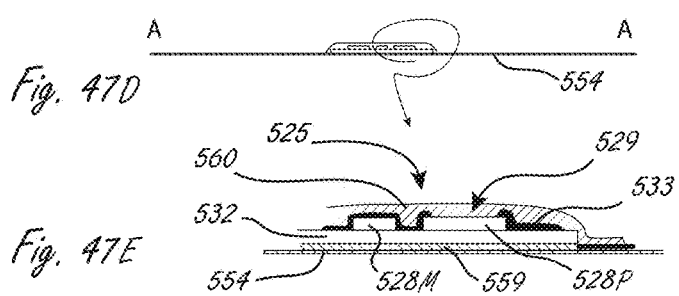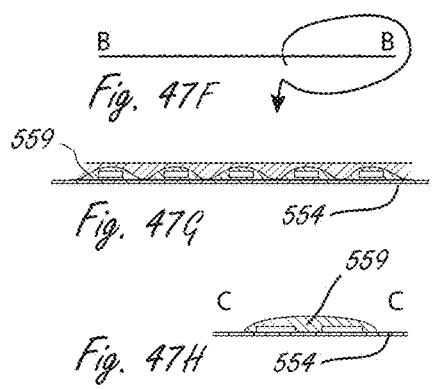

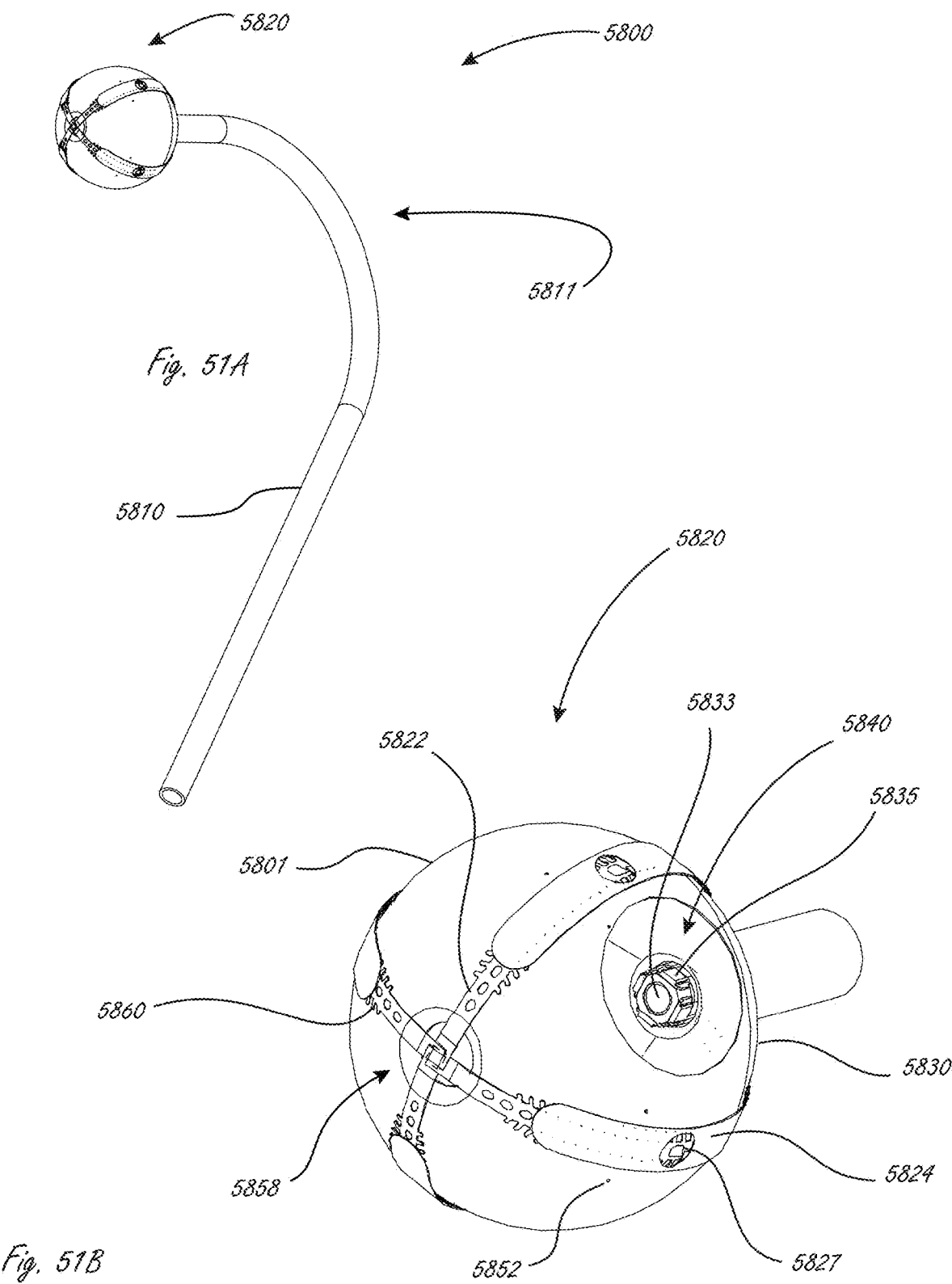

ENERGY DELIVERY DEVICES

CROSS REFERENCE TO RELATED APPLICATIONS

This application is a continuation of International Application PCT/US2016/062323, with an international filing date of Nov. 16, 2016, which claims priority to the following U.S. Provisional Applications: 62/255,895, filed Nov. 16, 2015; 62/259,596, filed Nov. 24, 2015; 62/309,359, filed Mar. 16, 2016; and 62/326,546, filed Apr. 22, 2016. All of the aforementioned applications are incorporated by reference herein. This application incorporates by reference herein the disclosures of the following: U.S. Pat. Nos. 8,295,902; 8,805,466; and U.S. Pub. No. 2014/0357956.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Therapeutic and/or diagnostic medical devices having one or more electrodes have been described. For example without limitation, catheters with electrodes carried by one or more expandable or deformable members have been described. Depending on the design and use, some previously described medical device with one or more electrodes may have some deficiencies or drawbacks. The disclosure herein describes examples of devices and methods of use that provide some advantages to those previously described.

SUMMARY OF THE DISCLOSURE

The disclosure includes a tissue ablation and visualization apparatus, comprising: an inflatable balloon disposed at a distal region of an elongate shaft; an ablation element carried by the balloon; a first lens disposed inside the inflatable balloon and providing a first field of view; and a second lens disposed inside the inflatable balloon and providing a second field of view different than the first field of view, the second lens axially spaced at a fixed distance from the first lens.

The apparatus can include a first image sensor disposed inside the inflatable balloon, the first image sensor positioned to receive light passing through the first lens, and a second image sensor disposed inside the inflatable balloon, the second image sensor positioned to receive light passing through the second lens, the second image sensor axially spaced at a fixed distance from the first image sensor.

The apparatus can further include a third lens disposed inside the inflatable balloon, the third lens axially spaced at a fixed distance from the first lens. The apparatus can further include a third image sensor disposed inside the inflatable balloon, the third image sensor positioned to receive light passing through the third lens, the third image sensor axially spaced at a fixed distance from the first image sensor. The apparatus can further comprise a fourth lens disposed inside the inflatable balloon, the fourth lens axially spaced at a fixed distance from the second lens. The first and fourth lenses can be axially aligned, or are at a fixed axial distance from each other that is less than the distance between the first and second lenses. The apparatus can further comprise a fourth image sensor positioned to receive light passing through the fourth lens, the fourth image sensor axially spaced at a fixed distance from the second image sensor. The second and third lenses can be axially aligned, or are at a fixed axial distance from each other that is less than the distance between the first and second lenses.

The apparatus can further comprise a third lens disposed inside the inflatable balloon, the third lens axially spaced at a fixed distance from the first lens. The apparatus can further comprise a fourth lens disposed inside the inflatable balloon, the fourth lens axially spaced at a fixed distance from the second lens.

The apparatus can further comprise a visualization housing assembly disposed inside the balloon, the visualization housing assembly comprising the first and second lenses. The apparatus can further comprise an elongate member disposed within the balloon and extending axially through the balloon, the elongate member secured to a distal end of the balloon, the elongate member disposed within the visualization housing assembly and axially moveable relative to the visualization housing assembly.

The apparatus can further comprise a plurality of electrodes carried by the balloon, each of the plurality of electrodes having a portion disposed at an apex of the balloon. The apparatus can further comprise a plurality of second electrodes carried by the balloon, each of which has a distal end that extends further distally than distal ends of each of the plurality of electrodes.

The disclosure includes a tissue ablation device, comprising: an inflatable balloon disposed at a distal region of an elongate shaft; a flexible circuit, carried by the balloon, comprising first and second arms spaced from one another along at least a portion of their lengths, the first arm comprising a first conductive member and the second arm comprising a second conductive member, the first conductive member extending to a proximal region of the first arm, and the second conductive member extending to a proximal region of the second arm; and a first electrode in electrical communication with the first conductive member, and a second electrode in electrical communication with the second conductive member, wherein the first arm has a proximal end that extends further proximally than a proximal end of the second arm.

The first and second arms can each comprise a substrate to which the respective conductive members are secured, each of the substrates extending to proximal ends of the respective arms.

Each of the first and second conductive members can include a proximal pad that is an electrical extension of the respective trace.

The first and second electrodes can be non-integral with their respective conductive members. Each of the electrodes can be disposed over a respective arm.

The first and second electrodes can be part of the first and second arms, respectively, the first and second electrodes being part of the same layer of material as the conductive members.

The device can further comprise a plurality of first arms, the first arm being one of the plurality of first arms, and a plurality of second arms, the second arm being one of the plurality of second arms, each of the plurality of first arms having a proximal end that extends further proximally than a proximal end of each of the plurality of second arms. The plurality of first arms and the plurality of second arms can be carried by the balloon in an alternating arrangement around at least a portion of the balloon. Each of the plurality of first arms can be adjacent to two of the plurality of plurality of second arms, and each of the plurality of second arms is adjacent to two of the plurality of first arms around the balloon. The plurality of first arms can comprise at least four arms, and wherein the plurality of second arms comprises at least four arms. Each of the plurality of first and second arms can comprise at least six arms. Each of the plurality of first arms can have a proximal end that extends to the same axial position along the device as each of the other proximal ends of the plurality of first arms. Each of the plurality of second arms can have a proximal end that extends to the same axial position along the device as each of the other proximal ends of the plurality of second arms.

The first arm can comprise a third conductive member extending to a proximal region of the first arm, the first conductive member having a proximal end that extends further proximally than a proximal end of the third conductive member, the third conductive member being in electrically communication with a third electrode.

The disclosure includes a tissue ablation device, comprising: an inflatable balloon disposed at a distal region of an elongate shaft; a substrate secured to an outer surface of the balloon, the substrate comprises a plurality of protrusions extending laterally and distally from at least one side of the substrate, the plurality of protrusions enhancing the substrate's adhesion to the balloon; an adhesive disposed between first and second of the plurality of protrusions, and in contact with the balloon; and a conductive element secured to the substrate and in electrical communication with an electrode.

The plurality of protrusions can extend laterally from first and second sides of the substrate.

At least 50% of the plurality of protrusions can have the same general configuration.

At least some of the plurality of protrusions can comprise two sides that are generally parallel.

At least some of the plurality of protrusions have a width from 0.001 inch to 0.5 inches.

At least some of the plurality of protrusions have a length from 0.001 inches to 0.05 inches.

At least some of the plurality of protrusions are axially spaced from 0.001 inches to 0.5 inches apart.

The substrate can comprise at least 5 protrusions on a first side. The substrate can comprise at least 5 protrusions on a second side.

The electrode can be disposed over the substrate covering at least some of the plurality of protrusions.

The disclosure includes a tissue ablation device, comprising an inflatable balloon disposed at a distal region of an elongate shaft; and a flexible circuit, carried by the balloon, comprising a plurality of arms spaced apart from one another along at least a portion of their lengths, wherein each of the plurality of arms comprises at least one ablation electrode, and wherein a first arm is adjacent to a second arm, the first arm having a different number of ablation electrodes than the second arm.

The plurality of arms can comprise a plurality of first arms and a plurality of second arms, the plurality of first arms having a first number of ablation electrodes, and the plurality of second arms having a second number of ablation electrodes different than the first number of ablation electrodes.

The plurality of arms can be arranged around the balloon such that the plurality of first arms and the plurality of second arms are in an alternating arrangement. The plurality of first arms can each have two ablation electrodes, and the plurality of second arms each have one ablation electrode. The plurality of arms can be arranged around the balloon such that the plurality of first arms and the plurality of second arms are in an alternating arrangement. The first and second arms can each comprise a mapping electrode.

The plurality of first arms can each include an electrode that is part of a first array of electrodes axially aligned along the length of the balloon. The plurality of second arms can each include an electrode that is part of a second array of electrodes axially aligned along the length of the balloon, the second array axially spaced from the first array. The plurality of second arms can also each comprise an electrode that is part of the first array of electrodes axially aligned along the length of the balloon.

The disclosure includes a tissue ablation device, comprising: an inflatable balloon disposed at a distal region of an elongate shaft; a plurality of electrodes carried by an outer surface of the balloon, each of the plurality of electrodes sized and positioned such that any two adjacent electrodes will, when activated in bipolar mode and with a power input 25 W or less, optionally 15 W or less, cause a complete burn to occur in tissue between the two electrodes.

The disclosure includes a method of ablating tissue at certain power densities, comprising: providing expandable device comprising an inflatable balloon and a plurality of electrodes carried thereby; moving at least two of the plurality of electrodes into contact with tissue; delivering RF energy between two adjacent electrodes in bipolar mode, at a power of 25 W or less, optionally 15 W or less, to create a power density based on the surface area of the electrodes and the space between the electrodes, of 40 W/cm$^2$ or less; and ablating tissue between the two electrodes by delivering the RF energy.

The disclosure includes a method of ablating tissue at certain power densities, comprising: providing expandable device comprising an inflatable balloon and a plurality of electrodes carried thereby; moving at least two of the plurality of electrodes into contact with tissue; and delivering RF energy between two adjacent electrodes in bipolar mode such that the energy density is 40 W/cm$^2$ or less.

The disclosure includes a tissue ablation device, comprising: an inflatable balloon disposed at a distal region of an elongate shaft; and a plurality of distal electrodes carried by an outer surface of the balloon, and a plurality of proximal electrodes carried by an outer surface of the balloon, the proximal electrodes and distal electrodes all having substantially the same surface area, optionally within 5% of each other, wherein the proximal electrodes have a first configuration and the distal electrodes have a second configuration, the first and second configurations being different.

BRIEF DESCRIPTION OF THE DRAWINGS

FIGS. 26 and 27 illustrate aspects of an external console.

FIG. 29 illustrates exemplary information and indicators that can be superimposed on the images from the cameras.

FIG. 30 represents an exemplary flexible circuit for application to the outer surface of a balloon.

FIG. 31 shows an assembled flexible circuit affixed to a balloon.

FIGS. 32A and 32B illustrate a composite view as described herein from a four camera array as presented to the user on a display.

FIGS. 40A, 40B, and 40C illustrate an exemplary diagnostic and/or therapeutic medical device.

FIGS. 41A, 41B, 41C, and 41D illustrate an exemplary visualization system for a diagnostic and/or therapeutic medical device.

FIGS. 47A, 47B, 47C, 47D, 47E, 47F, 47G, and 47H illustrate a portion of the exemplary flex circuit and electrode design from FIG. 46.

FIGS. 51A and 51B illustrate an exemplary embodiment of a steerable energy delivery and/or diagnostic device comprising flexible low-profile electrodes and sensor assemblies with an onboard imaging system in a compact design.

DETAILED DESCRIPTION

The disclosure describes methods of, and systems and devices configured for, diagnosing, preventing, and/or treating cardiac arrhythmias. The disclosure includes methods of and devices configured for ablating cardiac tissue. The disclosure is related to and incorporates by reference the devices and methods described in U.S. Pat. No. 8,295,902, issued Oct. 23, 2012, and U.S. Pub. No. 2012/0071870, published Mar. 22, 2012, the disclosures of which are incorporated by reference herein. Devices herein can incorporate suitable structural features in embodiments in the aforementioned applications even if the disclosure fails to expressly include them. Additionally, the methods of use herein can include suitable method steps in embodiments in the aforementioned applications even if the disclosure fails to expressly include them.

Figure 1A:
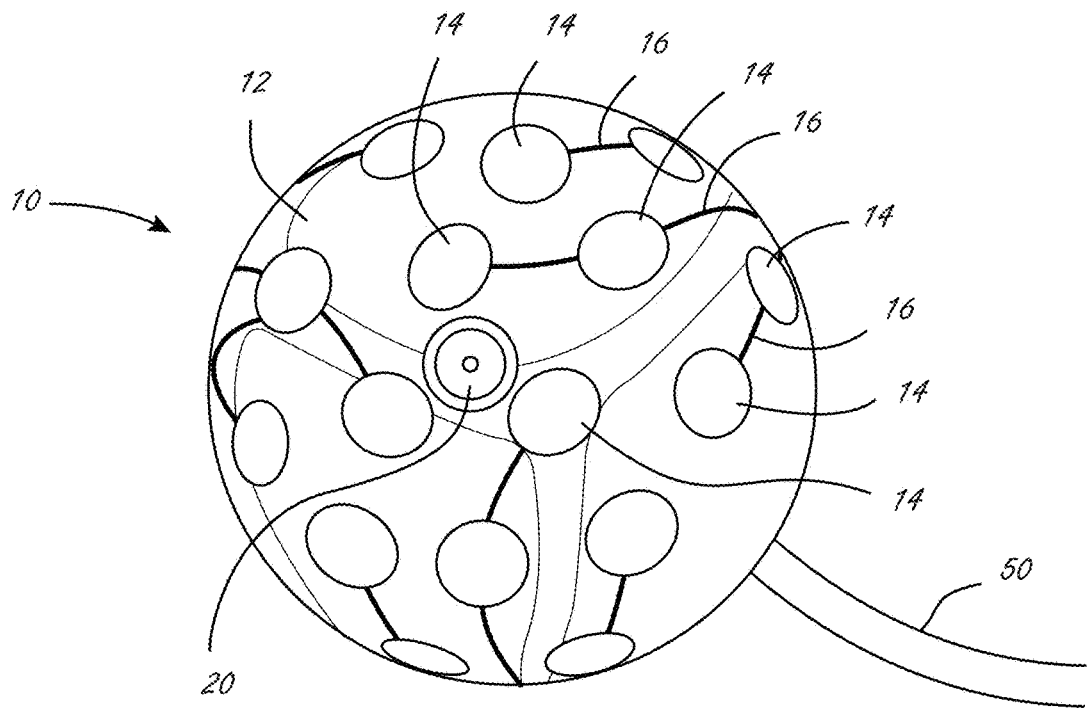
FIGS. 1A, 1B, and 1C illustrate an exemplary ablation device in an expanded configuration.
Figure 1B:
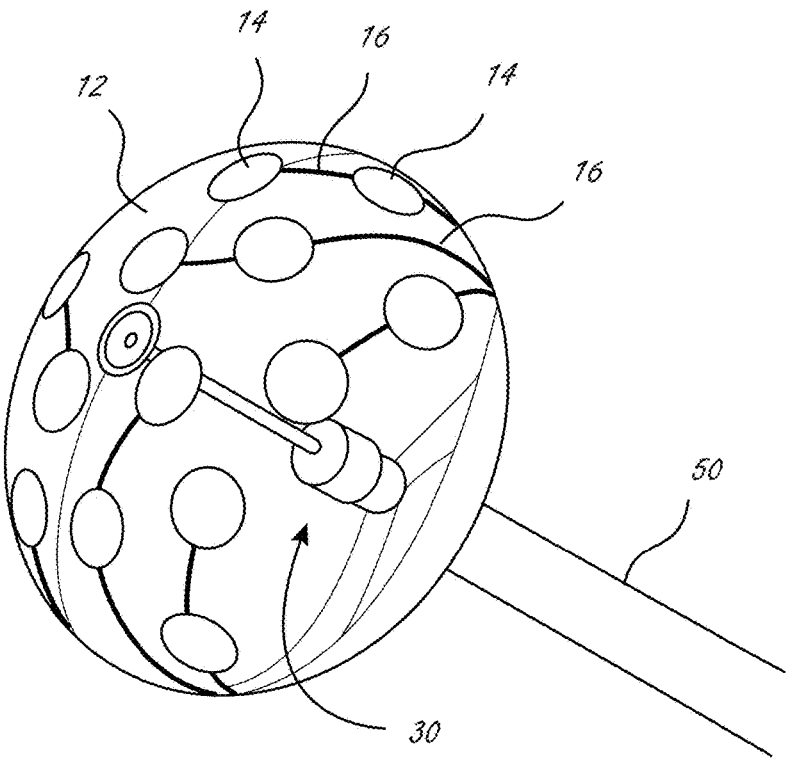
Figure 1C:
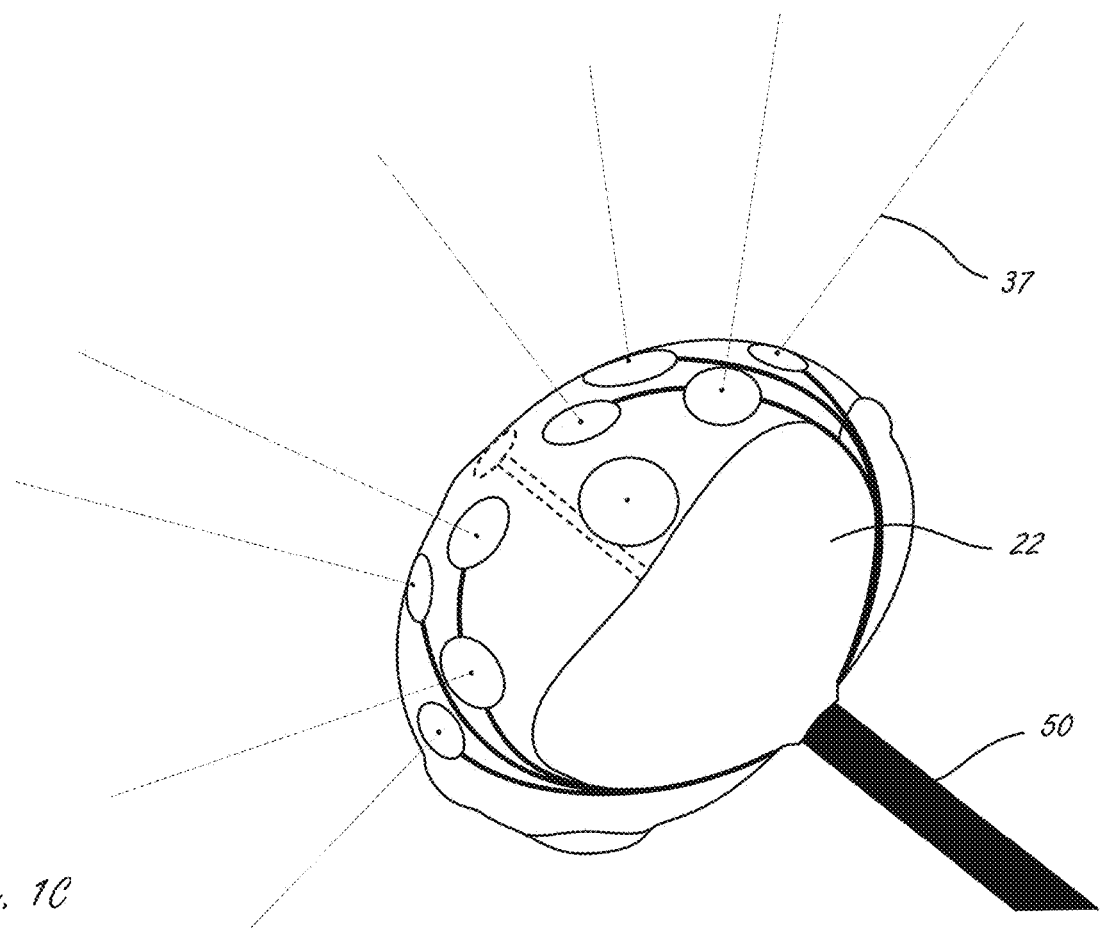

FIGS. 1A-1C illustrate a distal portion of an exemplary cardiac ablation catheter. FIGS. 1A-1C shows expandable member 10 in an expanded configuration. FIG. 1A is a distal view, FIG. 1B is a perspective view, and FIG. 1C is a side view.

The cardiac ablation catheter is configured to deliver ablative energy to tissue such as cardiac tissue and to ablate the tissue. Expandable member 10 includes membrane, or balloon, 12 and a plurality of energy delivery elements 14 secured to the exterior of membrane 12. In this embodiment energy delivery elements 14 are electrodes configured and positioned to deliver ablative RF energy to tissue when expandable member 10 is inflated and to ablate the tissue, and are in electrical communication with an RF generator (not shown) configured to generate RF energy.

Figure 1D:
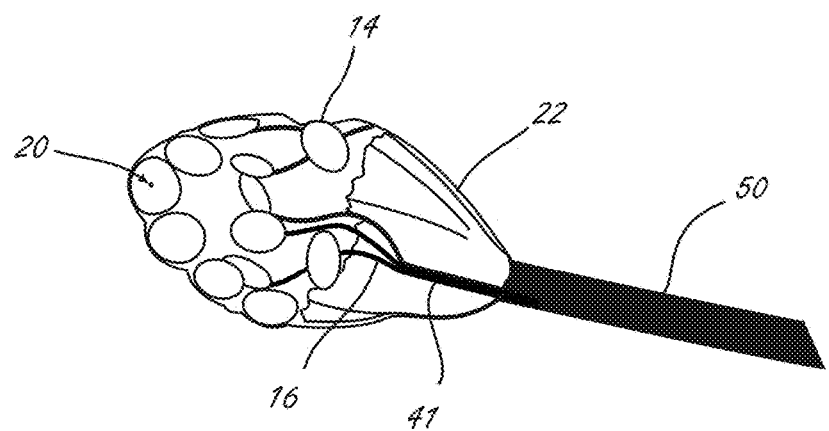
FIG. 1D illustrates an exemplary ablation device in a collapsed configuration.

FIG. 1D illustrates expandable member 10 in a collapsed, or deflated, configuration prior to full inflation.

Figure 2A:
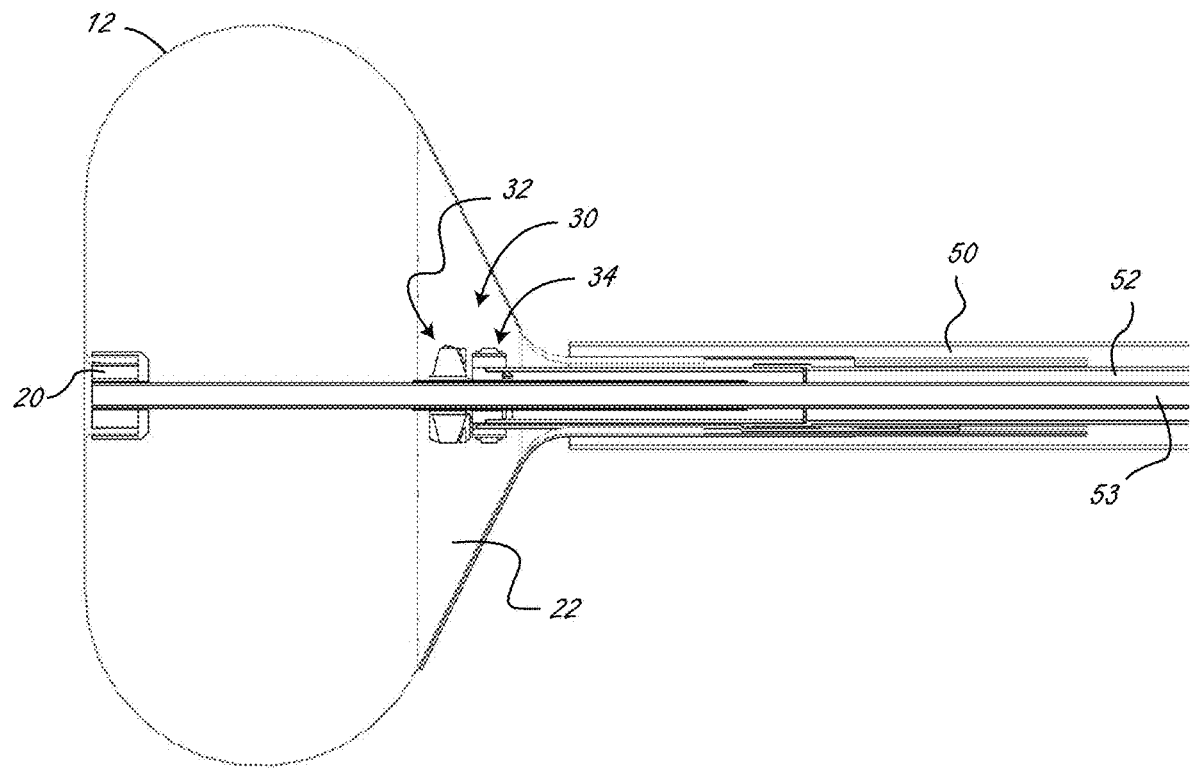
FIG. 2A is a side view of an exemplary distal region of an ablation catheter.
Figure 2B:
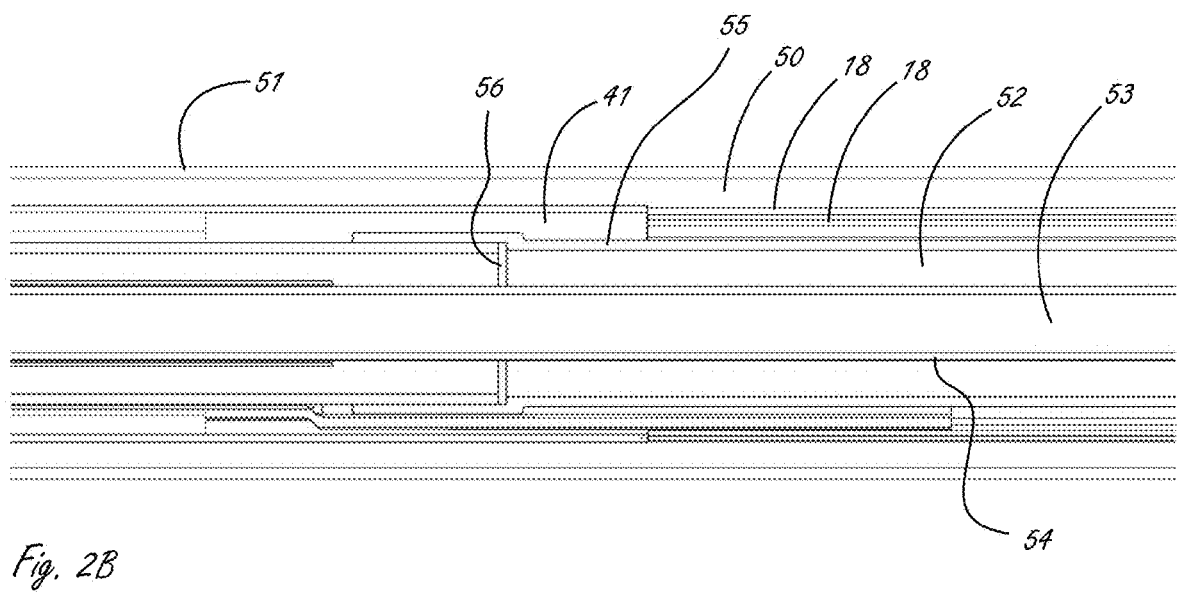
FIG. 2B is a close up side view of the inside of the catheter from FIG. 2A.

FIG. 2A is a side sectional view of the distal portion of the ablation catheter shown in FIGS. 1A-1C. FIG. 2B is a highlighted side sectional view of components within outer shaft 51. FIG. 2A shows membrane 12 expanded at the distal end of outer lumen 50, which is the annular space between outer shaft 51 and irrigation shaft 55. The distal end of membrane 12 is secured, such as by press-fit and/or adhesive, to distal hub assembly 20, between an inner member and an outer member of assembly 10 as shown. The proximal end of membrane 12 is secured to the outer surface of irrigation shaft 55. Hub 20 is secured to guide wire shaft 54, which in this embodiment defines guidewire lumen 53 so that the ablation catheter can be advanced over a guidewire (not shown). Guidewire shaft 54 and irrigation shaft 55 are adapted to be axially movable relative to one another, which allows the distal end of membrane 12 to be moved relative to the proximal end of membrane 12. Relative movement between the two components can allow for the shape of the balloon to be changed. The movement also assists in transitioning expandable member 10 to a collapsed configuration, as shown in FIG. 1D.

Visualization system 30 includes a camera assembly 32 and illumination sources 35 disposed on the guide wire shaft 54. The cameras are configured to enable real-time imaging of the procedure from within the expandable member 10 to visualize the membrane and electrodes, cardiac tissue when the membrane/electrodes and cardiac tissue interface, as well as lesion formation during the ablation procedure, as is described in more detail below.

FIG. 2B shows radially outer shaft 51, irrigation shaft 55 that defines irrigation lumen 52, and guide wire shaft 54 that defines guidewire lumen 53.

The materials of the membranes 12 described herein can vary. Generally, the membrane material is thin, readily foldable into a low profile and refoldable after expansion. The materials can be elastic, inelastic, stretchy, non-stretchy, compliant, semi-compliant, or non-compliant. In an embodiment, membrane 12 has an expandable structure and can be constructed of materials such as those materials used in the construction of balloon catheters known in the art, including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS) and the like.

Membrane 12 can be constructed of relatively inelastic polymers such as PE, POC, PET, polyimide or a nylon material. Membrane 12 can be constructed of relatively compliant, elastomeric materials including, but not limited to, a silicone, latex, urethanes, or Mylar elastomers. Membrane 12 can be embedded with other materials such as for example, metal, Kevlar or nylon fibers. Membrane 12 can be constructed of a thin, non-extensible polymer film such as polyester or other flexible thermoplastic or thermosetting polymer film. In one embodiment flexible membrane 12 can be about 0.001" to about 0.002" in thickness to provide sufficient burst strength and allow for foldability. In some embodiments it is preferable to have the electrode mechanical properties as close to the membrane mechanical properties as possible. One way of providing this is to use an inelastic membrane that will not stretch as it is expanded. This helps secure the branches to the membrane. Membrane 12 has a front, or distal, face that is generally flat but can have other shapes as well.

Expandable member 10 includes what is generally referred to in U.S. Pat. No. 8,295,902, issued Oct. 23, 2012, and U.S. Pub. No. 2012/0071870, published Mar. 22, 2012, as flex circuits. A flex circuit as used herein generally refers to a conductive layer, an insulation layer, and optionally a substrate layer. A flex circuit is in electrical communication with at least one electrode.

Figure 8:
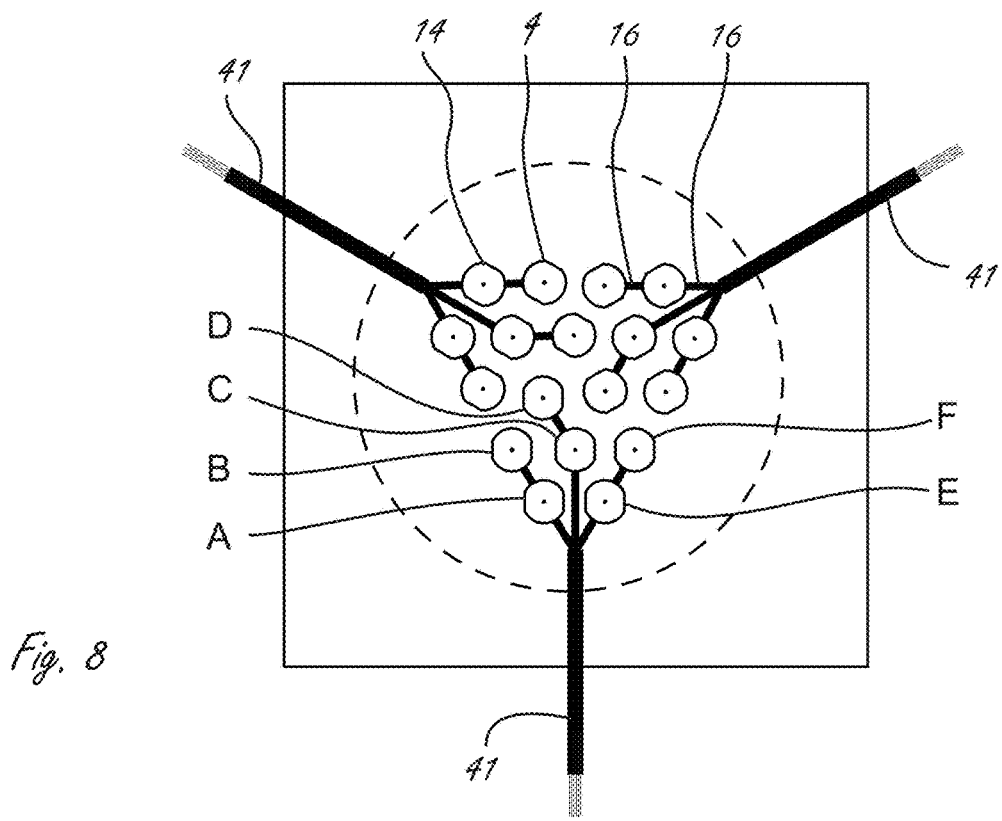
FIG. 8 is a flat view showing three individual flex circuits that are secured to the exterior of a membrane and to electrodes.

FIG. 8 is a flat view showing three individual flex circuits that are secured to the exterior of membrane 12. Each of the three flex circuits includes six energy delivery elements 14, and a tail terminating in termination 41 for the six conductive traces, one for each of the six electrodes. The terminations may be in the form of a connector or solder pads or other such suitable interface. The terminations 41 extend proximally from energy delivery elements on the expandable member, one of which can be seen in FIG. 1D. Each of the tails branch off into three branches 16, each one of which includes two energy delivery elements. Each of the two side branches 16 extend away from the longitudinal axis of the connector at substantially the same angle and each of two electrodes on a side branch is disposed at the same axial position (in the distal/proximal direction) as the other corresponding electrode on the other side branch. The central branch, however, initially extends along the same general direction as the longitudinal axis of a tail, and the first electrode on the central branch is axially disposed at the same general location as the second electrodes on the right and left branch. The central branch then extends away from the longitudinal axis of the tail, and the second (distal) electrode on the central branch is disposed further distally than the other five electrodes on the flex circuit, and is disposed radially (relative the longitudinal axis of tail) at the same general position as the first (proximal) electrode on one of the other side branches. In FIG. 8, the six electrodes on one of the flex circuits are labeled A-F. The two side branches of the flex circuit include electrodes A-B and E-F respectively. The central branch includes electrodes C and D. In the flat view, electrode C (the distal electrode of the central branch) is axially disposed at the same general position as electrodes B and F. Electrode D is disposed further distally than the other five electrodes, and is positioned radially in the same general position as electrode A. Electrodes A and E are disposed in the same general axial position, as are electrodes B, C, and F. Each of the three flex circuits is positioned on the expandable member, and the arrangement and size of electrodes provides for eighteen electrodes secured to the expandable member. As can be seen in FIGS. 1A and 1B, there are three electrodes closely surrounding hub 20.

Figure 9A:
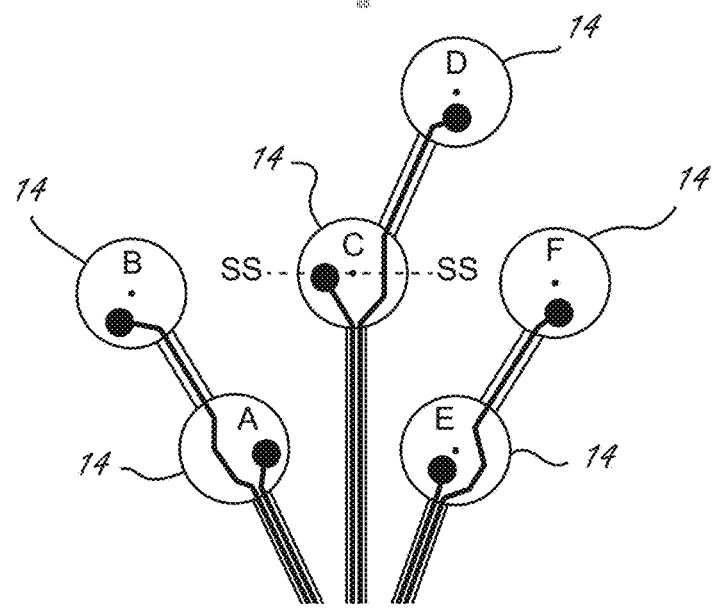
FIG. 9A illustrates a portion of one of the flex circuits and electrodes in FIG. 8.
Figure 9B:
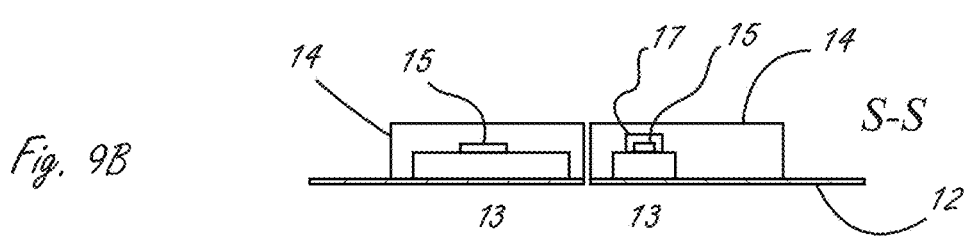
FIG. 9B illustrates the exemplary different layers of the flex circuit from section S-S from FIG. 9A.

FIG. 9A illustrates a portion of one of the flex circuits in FIG. 8 (the flex circuit in which termination 41 is at the "6 o'clock" position), including six energy delivery elements 14. FIG. 9A shows as alternative embodiment in which the distal electrode on the central branch 16 extends to the right on the page rather than the left, as is shown in FIG. 8. This arrangement provides the same general arrangement of the eighteen electrodes on the balloon. In the embodiment in FIGS. 1A-1C, there are three of the flex circuits from FIG. 9A disposed on membrane 12, and thus eighteen energy delivery elements secured to membrane 12. FIG. 9B illustrates the exemplary different layers of the flex circuit from section S-S from FIG. 9A. Electrically non-conductive substrate layer 13 is deposited on membrane 12, upon which conductive layers, or traces, 15 are deposited. Insulation layer 17 is deposited on top of conductive layers 15 except where the electrodes 14 are located. For example, to the left in FIG. 9B, an electrode 14 is disposed on electrically conductive element 15, thus electrically coupling electrode 14 and conductive layer 15, which is electrically coupled to an RF generator. On the right side of FIG. 9B, insulation layer 17 prevents conductor 15 on the right side from being electrically coupled to electrode 14. Instead, the conductor 15 on the right side will be electrically coupled to the distal electrode on that branch. Each individual conductor 15 is therefore electrically coupled to only one electrode 14. In the figure shown in 9A, there are six individual conductive traces 15, each of which is individually coupled to one electrode. As is described in detail in U.S. Pat. No. 8,295,902, issued Oct. 23, 2012; U.S. Pub. No. 2012/0071870, published Mar. 22, 2012, the electrodes are sized and configured to extend over a portion of the flex circuit and a portion of membrane not covered by the flex circuit. In this manner a large surface area electrode can be deposited onto and secured to the membrane. Each electrode is shown with an irrigation aperture in the middle thereof, as is described herein to irrigate tissue adjacent the electrodes and to prevent the irrigation fluid inside the membrane from becoming too hot and interfering with the tissue ablation.

The conductor or conductive layer 15 can be a material such as, but not limited to, a metal or metal foil of copper, gold, silver, tin, nickel, steel, cupronickel (copper-nickel alloy), KOVAR (nickel-cobalt ferrous alloy) or other material. In an embodiment, more than one conductive material can be used in the conductive layer 15. In an embodiment, a conductive layer 15 of copper can be plated with a thin layer of an additional conductive material at the conductive pad beneath electrode 14. In an embodiment, the thin layer of additional conductive material can be gold. The flex circuit and its components can be manufactured using techniques as known in the art.

The materials used to create the electrodes 14 can vary. The electrodes 14 can be a thin film of an electro-conductive or optical ink. The ink can be polymer-based for better adhesion to the membrane. The electrode material can be a biocompatible, low resistance metal such as silver, silver flake, gold, and platinum which are additionally radiopaque. Inks may additionally comprise materials such as carbon and/or graphite in combination with the more conductive materials already described. The addition of carbon and/or graphite can increase the conductivity of the polymer matrix. When incorporated as fibers the carbon and/or graphite add additional structural integrity to the ink electrode. Other fiber materials may be substituted to attain the same end. When the electrode material is not particularly radiopaque, additives such as tantalum and tungsten may be blended with the electrode material to enhance radiopacity. An example of an electro-conductive ink is provided by Engineered Conductive Materials, LLC (ECM) which is a polyurethane-based silver loaded ink. Another example is Creative Materials Inc., which manufactures conductive inks, films, as well as radiopaque inks. As mentioned above, the electrodes 14 can be applied to the membrane 12 and flex circuit using an adhesive. Alternatively, the electrode material can have adhesive properties or be an adhesive-loaded with conductive particles such as silver flakes such that electrodes 14 can adhere the components of the flex circuit to the membrane 12. If an additional adhesive layer is used to adhere the electrode 14 to the membrane 12 and flex circuit, the adhesive layer can include a conductive or non-conductive material. The electrodes formed with electro-conductive or optical ink or thin metal film can be visualized under fluoroscopy to provide a general sense of the shape of the membrane and location of the electrode. To enhance visualization under fluoroscopy, radiopaque additives can be included in the electrode material or radiopaque markers laid out next to, on top or below the electrodes as will be discussed in more detail below. Additionally, the bonding layer or substrate will be optimally comprised of a minimally reflective material.

Each of the electrodes is individually addressable, or can be used with any other electrode. The electrodes can operate in monopolar mode or bipolar mode, as is indicated in the exemplary schematic shown in FIG. 34. Electrodes sets can be chosen such that the lesion is, for example without limitation, linear, a spot, or a hollow circle.

Figure 3:
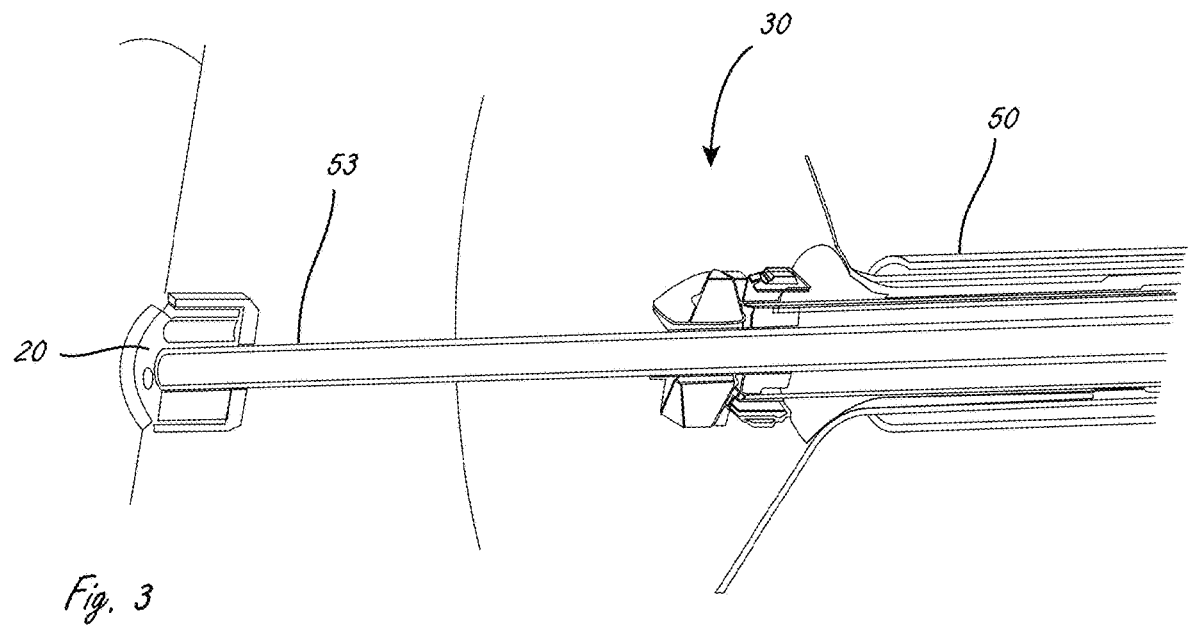
FIG. 3 is a perspective sectional view showing inside the expandable membrane.

FIG. 3 illustrates the coupling of the distal end of membrane 12 and hub 20, which can be press fit, adhesive coupling or a combination of both.

To prevent or reduce the likelihood of charring of tissue that is in contact with the energy delivery elements and coagulation of blood adjacent the electrodes, each of the flex circuits at the locations of the electrodes includes an irrigation aperture therethrough, and as shown are in the center of the electrodes. The irrigation apertures also prevent the inflation/irrigation fluid inside the membrane from becoming too hot, which would interfere with the ablation. Irrigation fluid, which is also the fluid that inflates membrane 12 causing it to be reconfigured toward its expanded configuration, is pumped from a fluid source through irrigation lumen 52, into membrane 12, through the irrigation apertures (not labeled), and towards the tissue that is in contact with the electrodes to cool the target tissue. One of the drawbacks of previous attempts at cardiac ablation is that the ablation procedures cause blood to coagulate or tissue to char due to lack of a cooling feature. Additionally, since each electrode is individually addressable, and the visualization system allows the operator to identify whether an individual electrode is in contact with tissue, only electrodes in contact with tissue may be turned on. Thus energy is more efficiently coupled to just the sites where ablation is desired and little to no energy is dissipated into the blood.

One of the significant advantages of ablation catheters herein is that, when in use, the ablation procedures can be visualized with an imaging, or visualization, member with a perspective from within the inflatable membrane. In the embodiment in FIGS. 1A-1D, imaging member 30 includes camera assembly 32 that includes a plurality of cameras 33 and a plurality of illumination, or light, sources, 35 (e.g., LEDs). Expandable member 10 also includes diffuse reflector 22 that is secured to the external surface of membrane 12.

Reflector 22 is a diffuse reflector adapted to create diffuse reflection of light incident upon it from the illumination sources. Reflector 22 is adapted to reflect light in a diffuse manner, as opposed to specular reflection, to better illuminate as much of the camera field of view as possible. If the reflector were adapted for specular reflection rather than diffuse reflection, light from the illumination sources that is reflected from the reflector would appear in the camera's field of view as a localized spot and would not illuminate as much of the field of view as possible.

Illumination sources 35 are configured and positioned to provide illumination generally radially outward towards reflector 22. Diffuse reflector 22 thus diffusely reflects light forward toward the camera's fields of view. The illumination sources thus provide lighting for the cameras to visualize the procedure, including the tissue, and the lesion formation.

In some embodiments the diffuse reflector is printed on the exterior of the balloon. The diffuse reflector can be comprised of silicone or urethane resins filled with nonconductive white pigment such as TiO, BaO, BaSo4, styrene or other polymer beads, or of metal particles. Optimal materials will be minimally reflective such as a black adhesive.

In this embodiment the diffuse reflector is secured to the membrane such that it does not completely overlap any of the electrodes, and is positioned so that the illumination sources, when activated, emit light towards the reflector. In this embodiment the diffuse reflector, or reflectors, is secured to the membrane at a location that does not extend all the way to the distal end of the membrane. In this embodiment the reflector is secured to the membrane such that it does not extend further distally than the proximal-most electrode. In alternative embodiments, however, the reflector can extend distally to the proximal-most electrode in some locations around the membrane. For example, the distal edge of the reflector can be curved rather than straight, and depending on the electrode layout on the membrane, some portions of the reflector may extend distally relative to the proximal-most electrode. If the membrane in its inflated configuration can be divided in half between the distal most location and proximal most location defining a distal portion and proximal portion, the reflector is disposed at least on the proximal portion. In the embodiment shown in FIGS. 1A-1C, the reflector is disposed only on the proximal portion.

One aspect of the disclosure is an expandable member that includes a diffuse reflector but does not include any ablation element. For example, medical devices that include an inflatable member and at least one camera and at least one light source therein can benefit from a diffuse reflector even if the device is not used for ablation procedures.

While the reflector herein is described as being a diffuse reflector, there may be some uses in which a reflector that reflects light in a specular manner may be beneficial. Alternatively, a reflector can have portions that reflect light in a diffuse manner and portions that reflect light in a specular manner.

Figure 4:
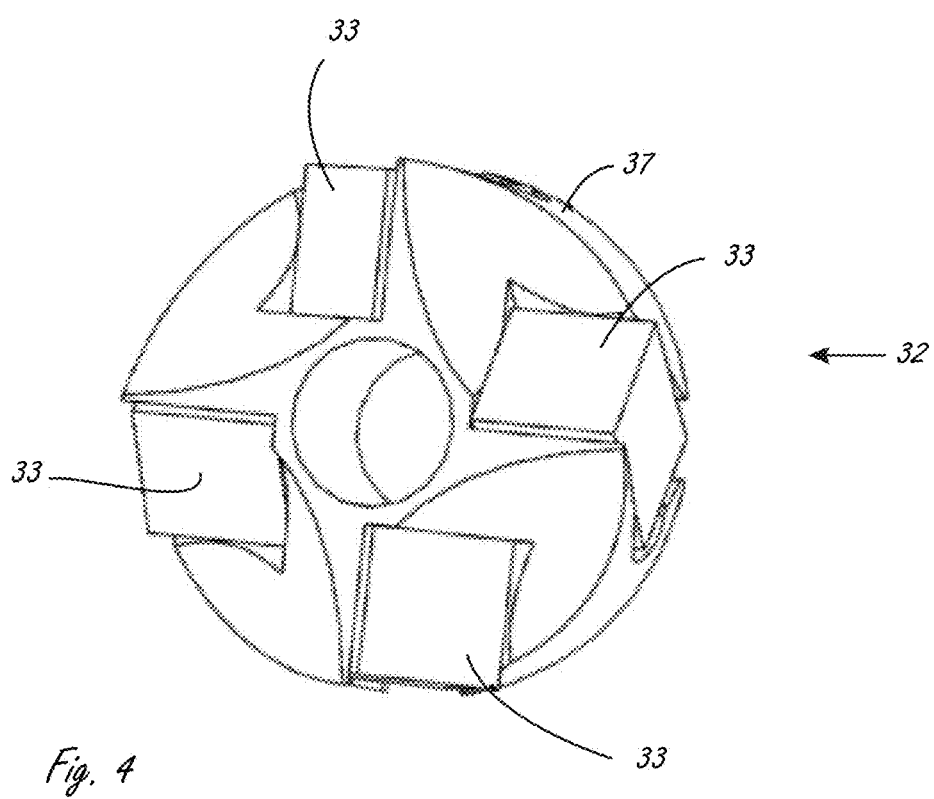
FIG. 4 illustrates a camera assembly.

FIG. 4 shows an exemplary camera assembly 32 that includes four cameras 33, which are disposed within camera hub 37 at an angle relative to the longitudinal axis of the catheter. Camera hub 37 is secured to guide wire shaft 54, and includes lumen 39 configured to receive guide wire shaft 54 therein.

Figure 5:
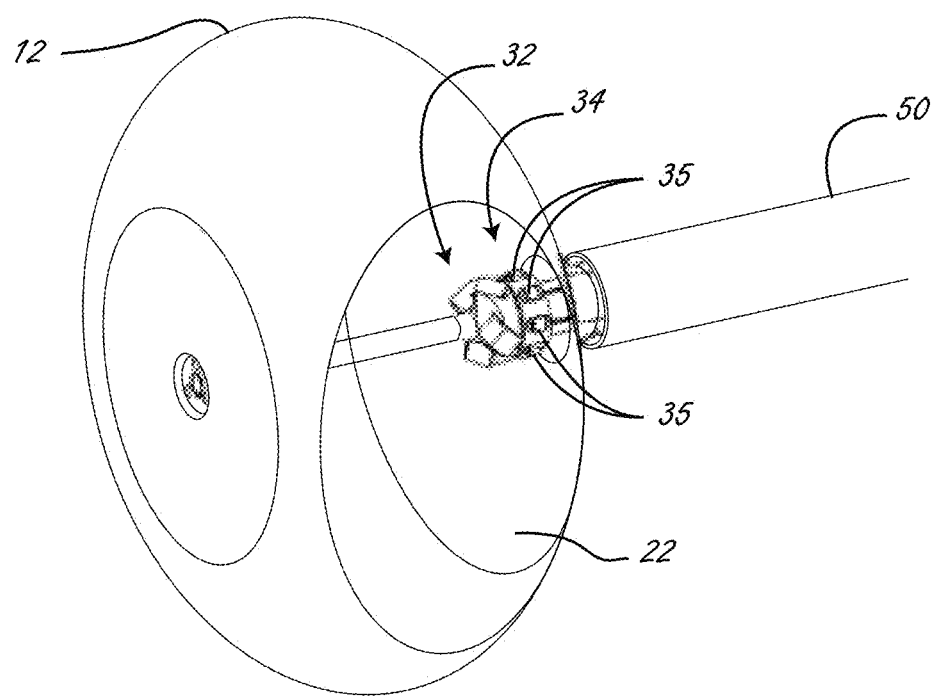
FIG. 5 is a perspective view of a distal region of an ablation catheter, with a cutaway of an expandable member.
Figure 6:
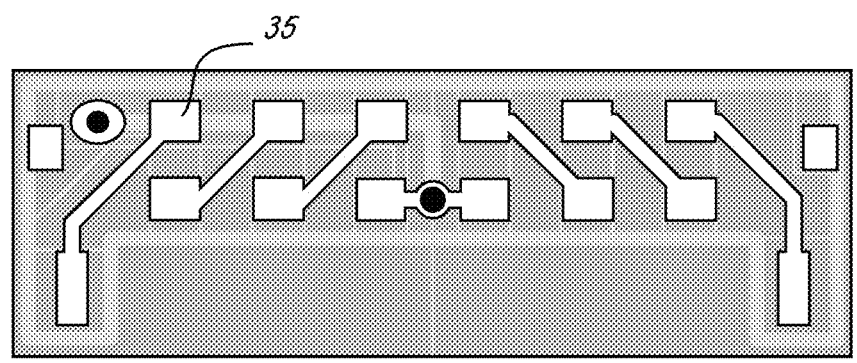
FIG. 6 is an exemplary flat view of an LED flex circuit.

FIG. 5 is another perspective view of expandable member 10 with a cutaway of the membrane. FIG. 6 is an exemplary flat view of the LED flex circuit, including the LEDs, that is wrapped around the illumination hub proximal to the cameras.

As set forth above, light is reflected from the diffuse reflector to provide illumination in the field of the view of the at least one camera. The field of view of the camera can include the view of an electrode secured to the membrane. As set forth herein, the electrodes can be highly reflective, such as if they are comprised of silver. Reflective electrodes causes light incident upon the electrodes to reflect into the camera field of view, which can cause the electrodes to appear as bright spots on the display, possibly interfering with viewing the procedure. It can thus be beneficial to include in the catheter a reflection adjuster that is adapted to reduce specular reflection of light from at least one of the plurality of ablation electrodes into the field of view of an imaging member.

In some embodiments the reflection adjuster is a light absorber. The light absorber can be positioned between the bottom of the electrodes and the membrane. In some embodiments the light absorber is a black adhesive that adheres portions of the electrode to the membrane, as well as acts as a light absorber.

In some embodiments the reflection adjuster is an anti-reflective coating. Exemplary anti-reflective coatings include, for example without limitation, a deposited thin layer of $TiO_2$, $MgF_2$, and "moth eye" structures comprised of nanoparticles approximately 200 nm in diameter spaced 300 nm range, random microstructure secured to or created on the interior surface of the membrane that is adapted to reduce reflection. The anti-reflective coating can be adhered to only a portion of the membrane, such as the portion where the electrodes are disposed. For example, an anti-reflective coating could be applied to only the distal portion of the inner membrane.

A reflection adjuster will reduce the amount of reflection from the bottom of the electrodes, creating a clearer image of the membrane and electrodes from within the membrane.

When the images or video provided by the at least camera are displayed on the display, it can be helpful to be able to visually identify the electrodes on the display. For example, a user interface can be used to control delivery parameters for any of the electrodes, and enabling the physician to easily determine and confirm that a given electrode on the video is a particular electrode on the user interface simplifies the procedures and ensures that the correct electrodes are being activated and used as intended.

In some embodiments the catheter includes an electrode identifier associated with at least one of the plurality of electrodes, and is some embodiments the catheter includes an electrode identifier with each of the plurality of electrodes. The electrode identifier need not be unique to each of the electrode, but in some embodiments it is unique to each electrode. The electrode identifier is visually identifiable and allows an individual to visually associate the identifier with an electrode.

In some embodiments the electrode identifier is an alphanumeric characters disposed on or near each of the electrodes. An example of this type of identifier is described and shown below. For example, an alphanumeric character can be printed on the back of an electrode, or the back of a portion of the flex circuit that is associated with an electrode. An alphanumeric character can also be printed on the membrane near the electrode so that the identifier can be easily associated with a particular electrode.

In some embodiments the electrode identifiers are colors associated with one or more of the electrodes. For example, the electrodes can be color-coded so that a user can visually identify each of the electrodes. In some embodiments a group of electrodes can have a particular color, such as all of the electrodes connected to the same flex circuit are all one color. An additional example of an electrode identifier is the shape of the electrode so that the electrode or group of electrodes can be visually identified based on their shape. For example, groups of electrodes can be circular, oval, hexagonal, rectangular, square, etc. Each electrode could have a unique shape to it as well.

An example of electrode identifiers is described below in the context of overlaying field of view images from a plurality of cameras.

Figure 10:
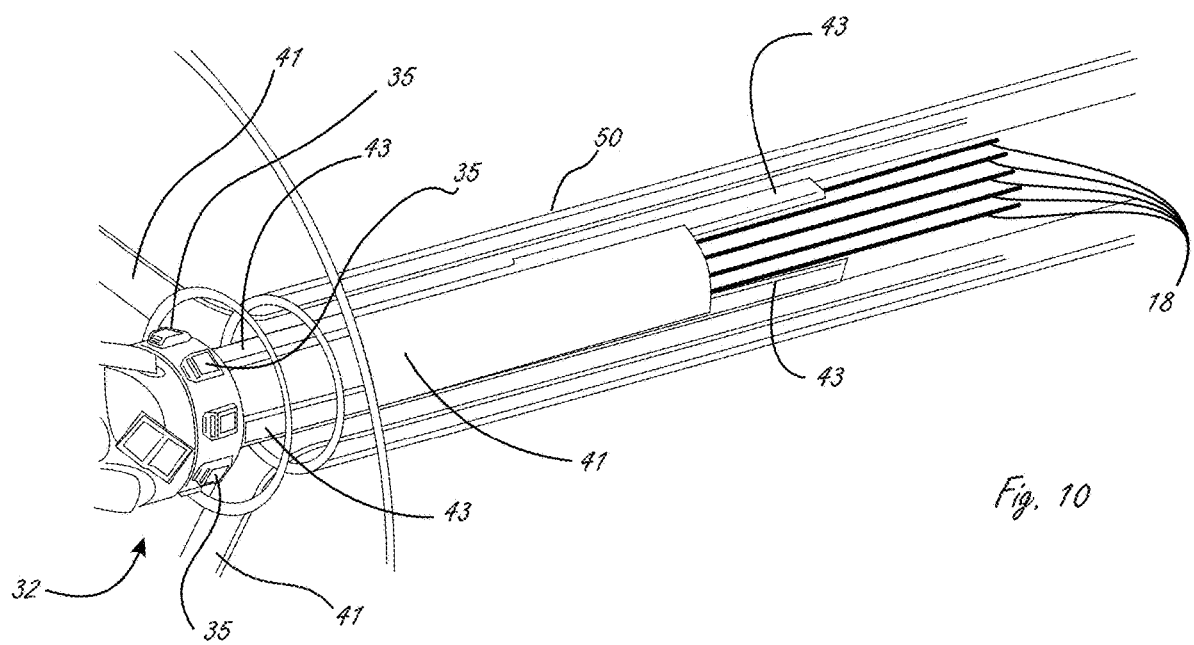
FIG. 10 illustrates each of the three flex circuit tails terminating in terminations extending proximally from the distal end of the balloon and extending proximally within an outer shaft and secured to the outer surface of the proximal end of the balloon and irrigation shaft.

FIG. 10 illustrates each of the three flex circuit tails terminating in terminations 41 (one for each flex circuit) extending proximally from the distal end of the balloon and extending proximally within outer shaft 51 and secured to the outer surface of the proximal end of the balloon and irrigation shaft 55. The proximal aspect of the configuration can also be seen in FIG. 2B. In FIG. 10, six conductive wires 18 can be seen extending proximally from one of the terminations 41, each one of which is in electrical communication with one of the six electrodes in that particular flex circuit. The six wires 18 extend the length of the catheter and are in communication with the RF generator. In an alternate embodiment, not shown, the six conductive traces 15 extend the length of the catheter and are in communication with the RF generator. Camera flex circuit 43 for the visualization system is also shown in FIG. 10, extending proximally from the visualization system in the catheter.

Exemplary materials for the membrane and flex circuit materials can be found in U.S. Pat. No. 8,295,902, issued Oct. 23, 2012; U.S. Pub. No. 2012/0071870, published Mar. 22, 2012. Additional examples of membrane material include PET, Polyurethane, etc. Exemplary materials for the reflector include metalized paints, silicone or urethane resin filled with nonconductive white pigment such as TiO or BaO or BaSo4, preferably non-conductive. Exemplary materials for the electrodes include silver filled silicone or urethane. Exemplary materials for the conductive traces are conductive metals including copper or other such conductive materials. The insulation layers can be known dielectric materials. Exemplary materials for the substrate include Kapton.

In use, the visualization system allows for real-time visualization of the procedure with a view by one or more cameras disposed within the balloon. The visualization allows for the entire procedure to be visualized, allowing physicians to assess the degree of tissue contact, and see the electrodes, tissue, and lesion formation as it occurs. For clarity, FIG. 29 illustrates only one of the four field of views for one of the four cameras in the camera assembly. FIG. 30 illustrates the four field of views from the four cameras, each overlaid with at least one other field of view, to give the physician a 360 degree view (with the longitudinal axis of the catheter as the reference) of the treatment area. While there is a blind spot shown in the center of the four images, different lensing systems than those used in the current embodiments can allow for elimination of that spot. Since there are electrodes disposed around the entire catheter, the 360 degree view allows the physician to visualize an entire lesion that utilizes electrodes disposed around the catheter. The visualization of the entire procedure including lesion formation at any of the electrode locations is immensely helpful to the physician.

The description herein of overlaying camera field of views is related to the disclosure in U.S. Pub. No. 2012/0071870, in particular FIGS. 38H-38R, and the textual descriptions thereof. One aspect of this disclosure is an exemplary method of generating a panoramic image display using images from a plurality of cameras attached to an endoscopic catheter. In some embodiments a plurality of images captured from a plurality of cameras are overlayed with at least one other image to create the panoramic image around the longitudinal axis of the ablation catheter. Two or more cameras can image various sections of the expandable member (from within the expandable member) and the anatomy, and the geometric relationships between the cameras are either known a priori (by design or measurement), or can be estimated from the images themselves using common anatomical features of the balloon as landmarks.

In general, for each camera, a mapping function that maps a pixel into a virtual unwrapped display screen, e.g. a dome-shaped screen, surrounding the cameras is computed. The images are then projected back to this virtual display screen using inverse projection, i.e., using cameras as projectors. Data in overlapping regions are combined using compositing including blending or some other means.

Figure 11:
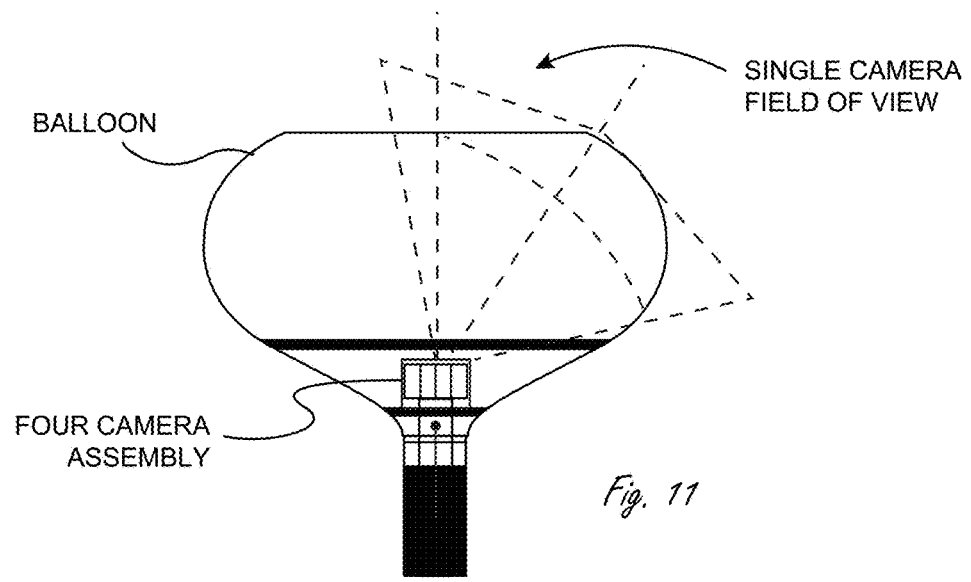
FIG. 11 is a side view of a distal portion of an exemplary visualization catheter.

FIG. 11 is a side view of a distal portion of an exemplary visualization catheter. FIG. 11 shows the geometry of the distal portion, which includes four cameras attached to the distal end of the central shaft of the catheter, surrounded by a membrane filled with saline. Each camera is imaging a section of the closed membrane from within the membrane. The conical shape shown in FIG. 11 represents the field of view of one of the plurality of cameras. In this embodiment, while not shown in FIG. 11, a plurality of radio frequency electrodes are secured to the exterior of the membrane. When the distal portion is positioned inside a cardiac chamber such as the left atrium, the cameras are able to visualize blood or tissue outside the balloon as well as the inner surface of the balloon. This provides a way to verify that the electrodes are in contact with tissue prior to starting the ablation and the balloon is located properly relative to anatomical landmarks such as a pulmonary vein.

Figure 12A:
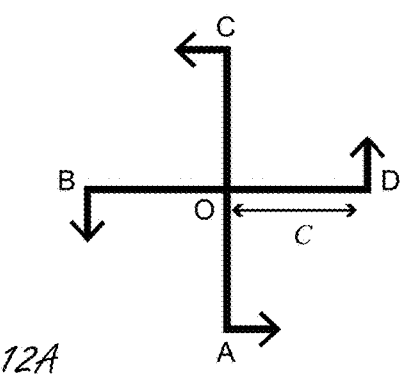
FIGS. 12A, 12B, 12C, and 12D show the orientations of the axes of four cameras in relationship to the longitudinal axis of a catheter shaft.
Figure 12B:
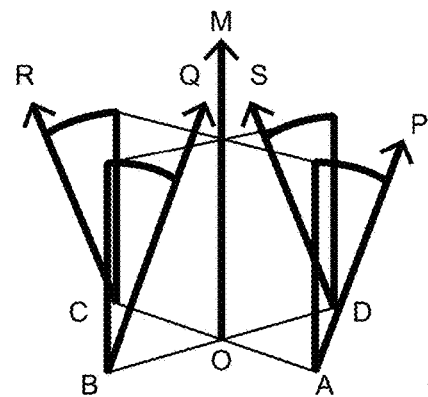
Figure 12C:
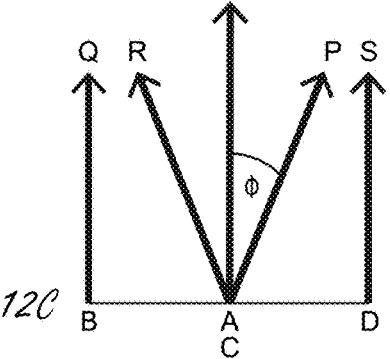
Figure 12D:
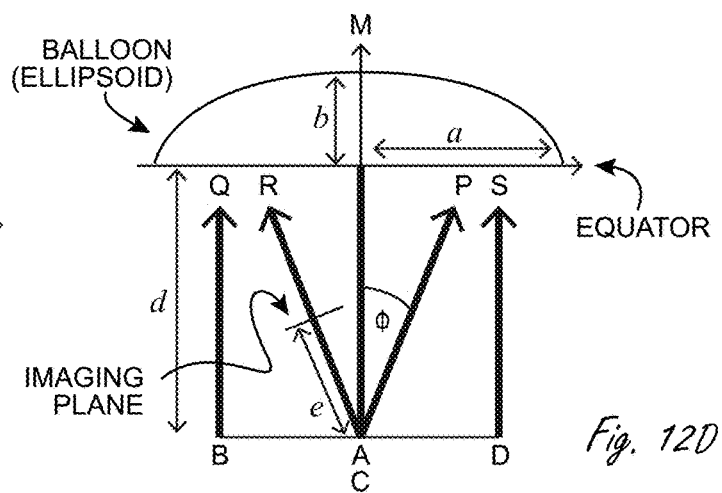

FIGS. 12A-12D show the orientations of the axes of the four cameras in relationship to the longitudinal axis of the catheter shaft. Arrows AP, BQ, CR and DS shown in FIG. 12C represent the axes of the respective cameras. OM is the longitudinal axis of the catheter shaft. The parameter "c" is the shortest distance between the axis of the catheter shaft OM and an axis of a camera (see FIG. 12A). The camera axis is also at an angle Φ relative to the axis of the catheter shaft OM (see FIG. 12B). The distal surface of the membrane can be modeled as an elliptical solid of revolution, as shown in the side geometrical view of FIG. 12D. Parameters a and b define the ellipsoid. The equator of the ellipsoid, as labeled in FIG. 12D, is at a distance "d" from the point "O" shown in FIG. 12D. The imaging plane of the camera with the axis CR is at a distance e from C, as shown in FIG. 12D.

Figure 13:
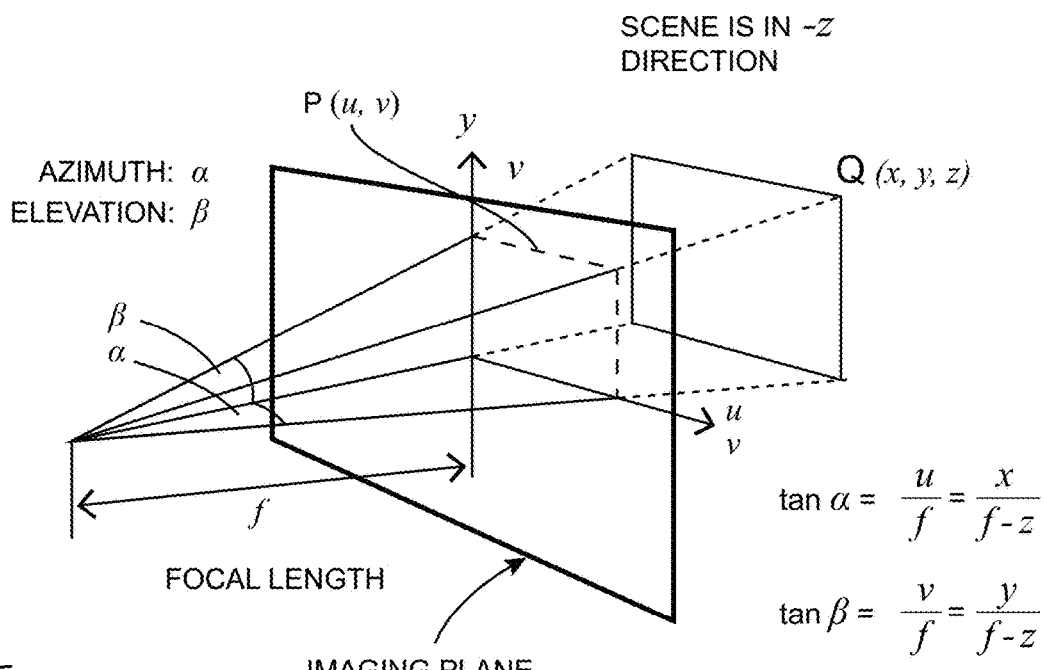
FIG. 13 shows the geometry of one of the four cameras, and all four have the same geometry.

FIG. 13 shows the geometry of one of the four cameras field of view, and all four have the same geometry. A pixel in the imaging plane, P(u, v), is related to a point Q(x, y, z) in space by equations (1) and (2), where f is the focal length of the camera.

$$\frac{u}{f} = \frac{x}{f-z} \qquad (1)$$

and $$\frac{v}{f} = \frac{y}{f-z} \qquad (2)$$

Figure 14:
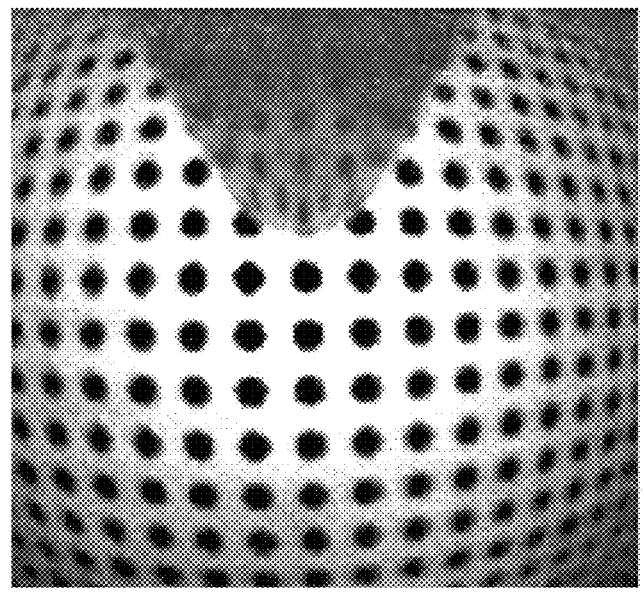
FIG. 14 shows a picture of a regular grid pattern target taken by a representative camera.

Furthermore, the image captured by the camera can have lens barrel aberration. FIG. 14 shows a picture of a regular grid pattern target taken by a representative camera. As can be seen, barrel aberration causes the grid points farther away from center 390 to appear smaller and compressed to each other.

The mapping function that maps the original pixel coordinates, P(u, v), to a distorted pixel coordinate system due to barrel aberration, $\tilde{P}(\tilde{u}, \tilde{v})$, can be determined by using the grid target:

$$\begin{bmatrix} \tilde{u} \\ \tilde{v} \end{bmatrix} = \begin{bmatrix} F(u) \\ G(v) \end{bmatrix} \quad (3)$$

Figure 15A:
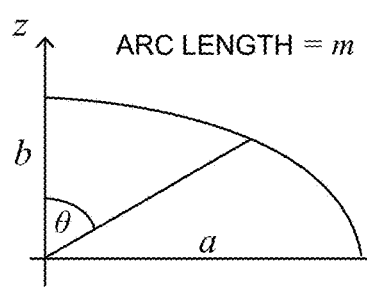
FIGS. 15A, 15B, and 15C show parameterization that can be used to unwrap the 3D surface of the ellipsoidal balloon into a 2D plane.
Figure 15B:
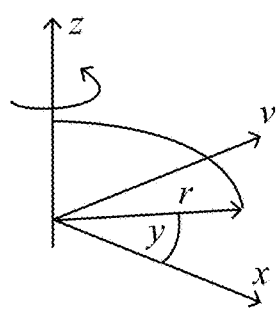
Figure 15C:
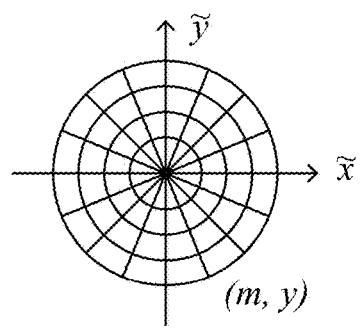

The 3D surface of the ellipsoidal balloon can be unwrapped into a 2D plane using the parameterization shown in FIGS. 15A-15C. In FIG. 15A, the parameters of a and b describe the balloon as an elliptical solid of revolution. The parameter m corresponds to the arc length along the balloon surface, starting from the zenith. In FIG. 15B the rotation angle γ describes the azimuthal angle of the solid of revolution. In FIG. 15C, the unwrapped balloon surface is defined by the parameters (m, γ) in polar coordinates or ($\tilde{x}$, $\tilde{y}$) in rectilinear coordinates.

A point on the balloon surface can be: (x, y, z). A planar unwrapped image can be constructed from the ellipsoidal balloon geometry by unwrapping the balloon surface as follows:

$$\begin{bmatrix} x \\ y \\ z \end{bmatrix} = \begin{bmatrix} a \sin \theta \cos \gamma \\ a \sin \theta \sin \gamma \\ b \cos \gamma \end{bmatrix} \quad (4)$$

Where:

$$\theta = g(m) \quad (5)$$

and g(m) is the well-known "Complete Elliptic Integral of the Second Kind." The unwrapped 2D surface is defined by the polar coordinates: (m, γ) or in rectilinear coordinates, ($\tilde{x}$, $\tilde{y}$), where:

$$\begin{bmatrix} \tilde{x} \\ \tilde{y} \end{bmatrix} = \begin{bmatrix} m \cos \gamma \\ m \sin \gamma \end{bmatrix} \quad (6)$$

In summary, the parameters in Table 1 (below) describe the camera geometry of this multi-camera system.

TABLE 1

| | Parameter | Description |
|---|---|---|
| 1 | a | Ellipsoidal balloon geometry |
| 2 | b | |
| 3 | c | Distance offsets |
| 4 | d | |
| 5 | e | |
| 6 | f | Focal length |
| 7 | φ | Camera angulation |
| 8 | F | Barrel aberration mapping function |
| | G | |

Using the parameters of Table 1, the ($\tilde{x}$, $\tilde{y}$) coordinates of the point on the unwrapped balloon corresponding to each pixel in an image produced by a given camera can be computed. Then the intensity of that pixel can be painted on the unwrapped balloon surface. If more than one camera projects data on to the same location on the unwrapped balloon surface, the data can be combined using any number of exemplary ways, such as blending, maximum value, adaptive blending, alpha blending, weighted averaging, etc. These techniques fall into the general category of "Compositing" as described in Foley et al., "Computer Graphics Principles and Practice", 1990, Addison Wesley, 2nd Edition. ISBN 0-201-12110-7. In the overlapping areas of images from two or more cameras, the underlying anatomical structure may be slightly misaligned even after following the above steps to grossly align the image due to inaccuracies in the geometric model. In this case, a given tissue structure may appear twice in the overlapping area, similar to double vision. To address this problem, images can be locally warped by using feature tracking. See U.S. Pat. No. 6,659,953, issued Dec. 9, 2003 to Sumanaweera et al., titled "morphing diagnostic ultrasound images for perfusion assessment," for a description of an exemplary local warping technique.

Figure 16:
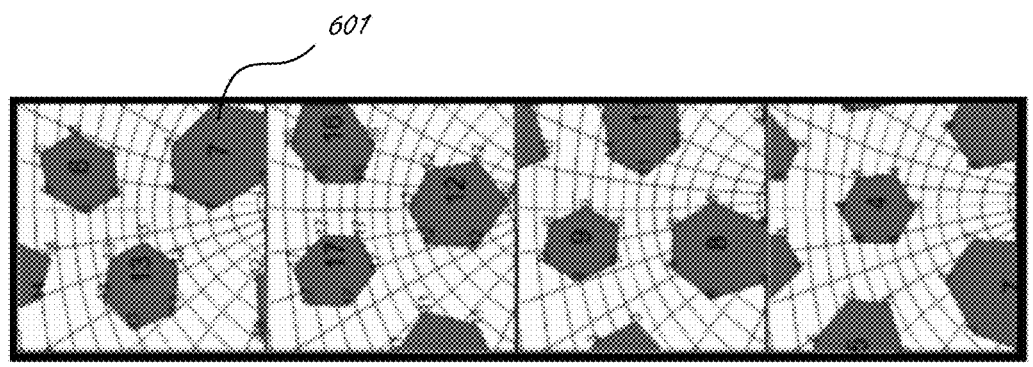
FIG. 16 shows a set of four camera images simulated using a known pattern, in this case, ablation electrodes painted on the membrane.

FIG. 16 shows a set of four camera images simulated using a known pattern, in this case, ablation electrodes 601 painted on the membrane. Electrodes 601 can be in the pattern of the eighteen electrodes shown in FIGS. 1A-1D. Electrodes 601 also have an identifier associated with them, in this case a unique alphanumeric character.

Figure 17:
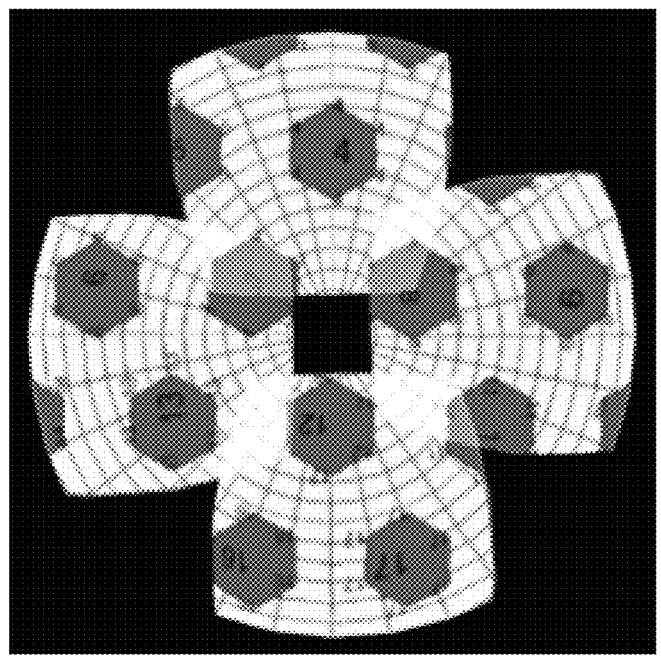
FIG. 17 shows the panoramic image generated by projecting the images from FIG. 22 back onto the unwrapped balloon surface using the methods described above.
Figure 19:
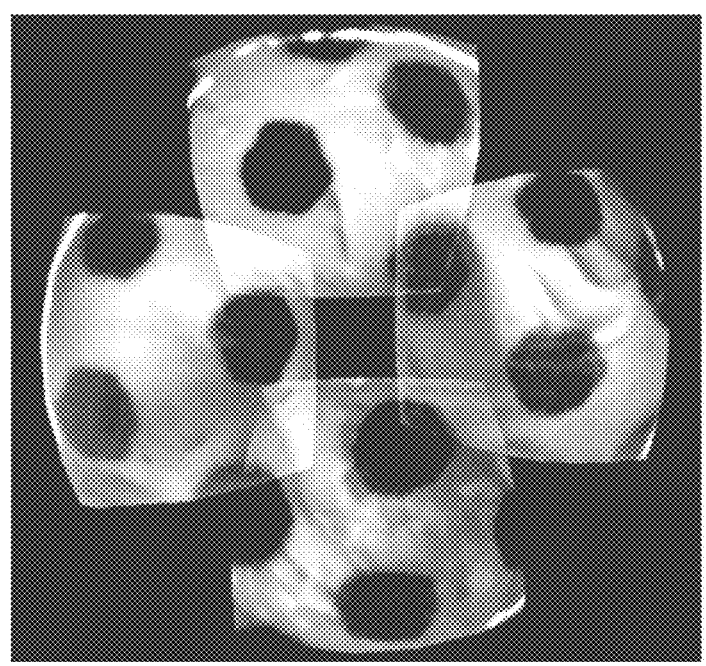
FIG. 19 shows tissue images acquired by four cameras using the methods described herein.
Figure 20:
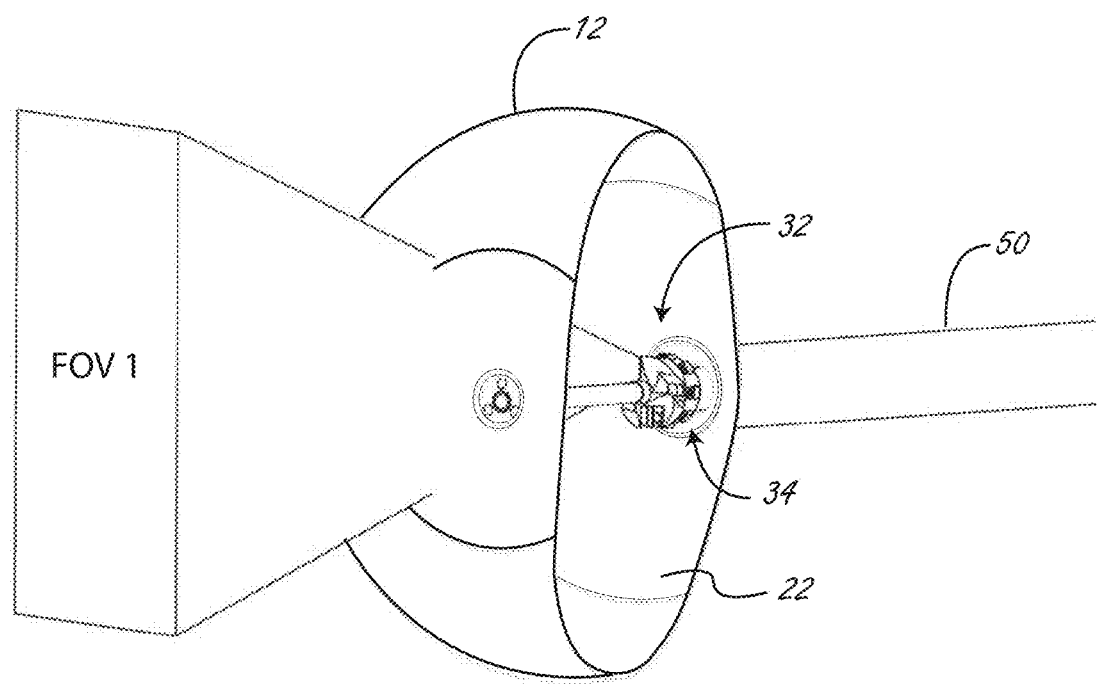
FIG. 20 illustrates only one of the four fields of view for one of the four cameras in the camera assembly.
Figure 21:
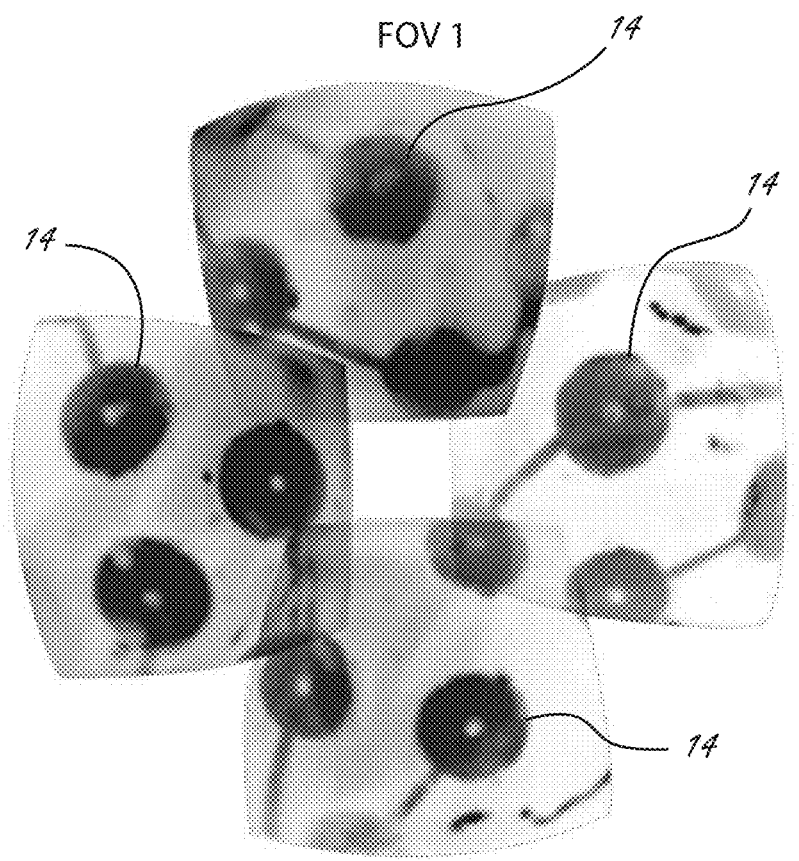
FIG. 21 illustrates the four fields of view from the four cameras, each overlaid with at least one other field of view, to give the physician a 360 degree view.

FIG. 17 shows the panoramic image generated by projecting the images from FIG. 16 back onto the unwrapped balloon surface using the methods described above. FIG. 19 also illustrates exemplary electrode identifiers in the form of numbers printed on each electrode to enable visual identification of each of the electrodes. FIG. 19 also illustrates how the collected images comprise common regions to images that are positioned adjacent to them, and that the common regions are overlapped to create the panoramic image.

Figure 18:
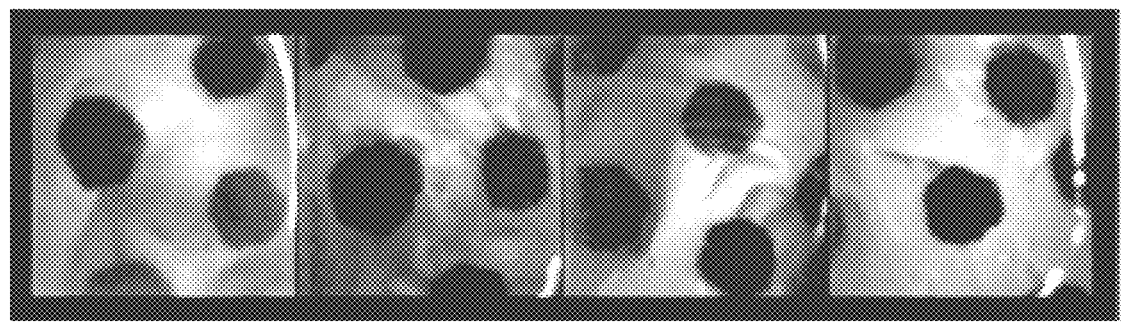
In FIG. 18 the panoramic image is generated by projecting the component images back onto the unwrapped balloon surface.

In FIG. 18 the panoramic image is generated by projecting the component images back onto the unwrapped balloon surface, but the electrodes 370 do not have electrode identifiers associated with them. FIG. 19 shows tissue images acquired by four cameras using the methods described above. FIG. 19 shows the panoramic image generated by projecting these images back onto the unwrapped balloon using the present invention.

The exemplary method above acquires an image from each of a plurality of cameras, and combines the images to produce a panoramic image. As set forth above, the images from each camera can be deformed using a geometric transformation. The deforming can comprise information associated with the known geometric relationship between the cameras. The deforming procedure can comprise geometric transformations generated using compositing in the overlapping areas of the images. The procedure can comprise the use of weighted averaging. The procedure comprises alpha blending. The deforming procedure can comprise geometric transformations generated using feature tracking in the overlapping areas of the images. The characterization of the geometric relationship between the cameras can comprise the use of experimentally determined optical targets. The geometric relationship can be determined analytically by geometrically modeling the cameras, the fixture containing the cameras and the balloon. The geometric transformation can include geometric transformations that map the balloon onto a planar surface while maintaining the distance between any arbitrary set of points on the 3D surface.

In an exemplary method of use, the catheter is used to ablate cardiac tissue in the treatment of a cardiac arrhythmia.

The catheter is advanced into the left atrium using known access procedures including guide wire and guide catheter techniques. Inflation/irrigation fluid is then pumped from a fluid source down inflation/irrigation lumen 52 to inflate the balloon to the configuration shown in FIGS. 1A-1C within the left atrium. The camera can be activated at any time during the procedure, but generally before inflation so the physician can see if there are any problems with the inflation. At this point the balloon is surrounded by blood, which can be seen. The catheter is advanced distally towards the atrial wall, and as the balloon contacts tissue the blood will be displaced, providing a clear view of the tissue. The physician can then determine if the balloon needs to be moved depending on the desired treatment tissue or desired area to map. An advantage of the visualization system in the devices herein is that the physician can easily see, simply by viewing a display showing the camera field of views, when the balloon is properly positioned. This also simplifies the system in that an analysis of reflected energy need not be performed, as in the case in some previous attempts at cardiac ablation.

Figure 24:
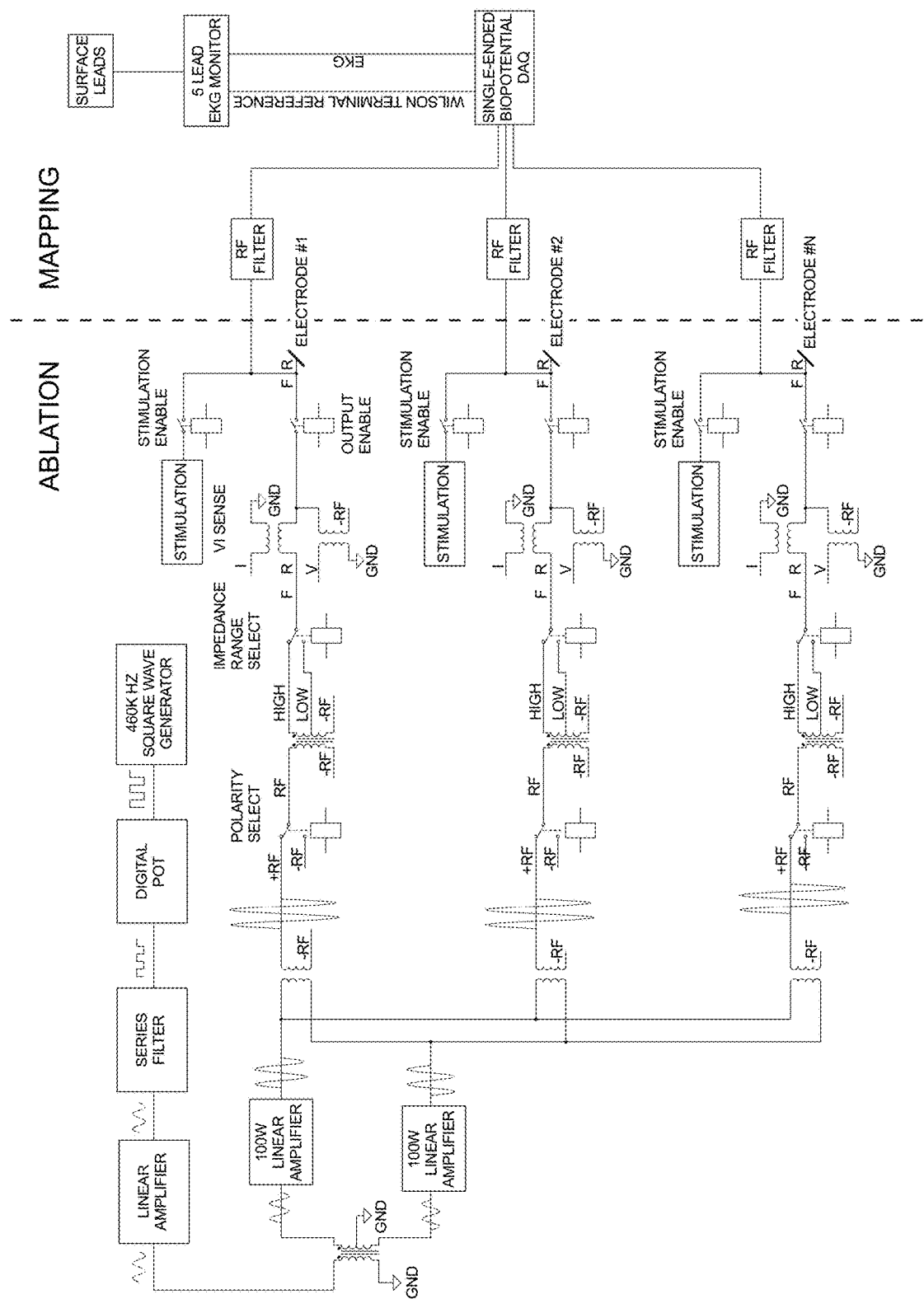
FIG. 24 is an exemplary schematic of the electrical aspect of an exemplary embodiment.
Figure 25:
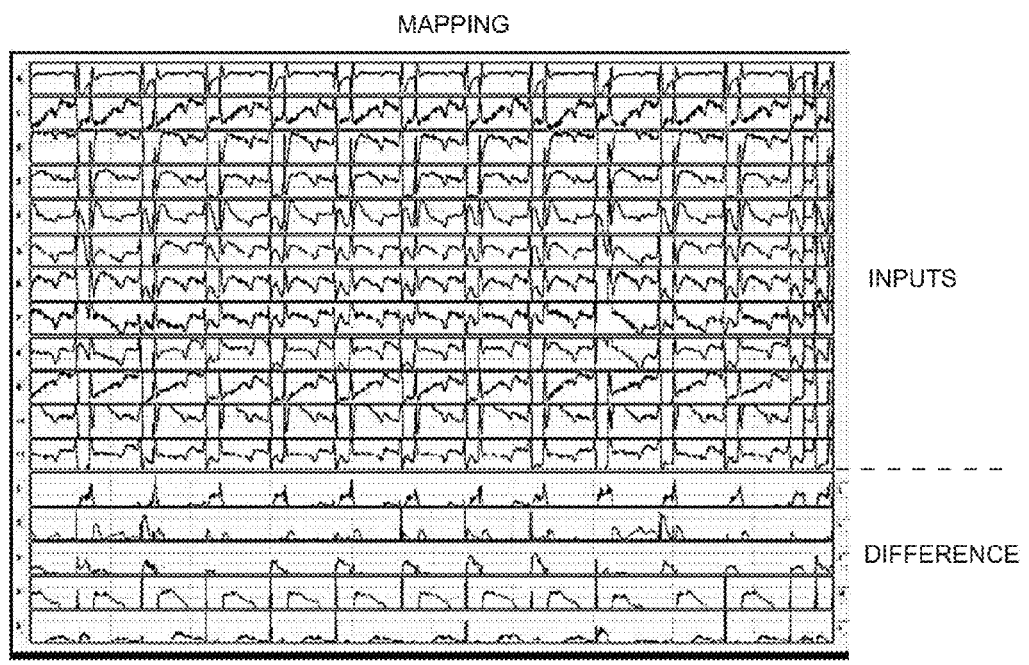
FIG. 25 illustrates mapping signals from a plurality of channels.
Figure 26:
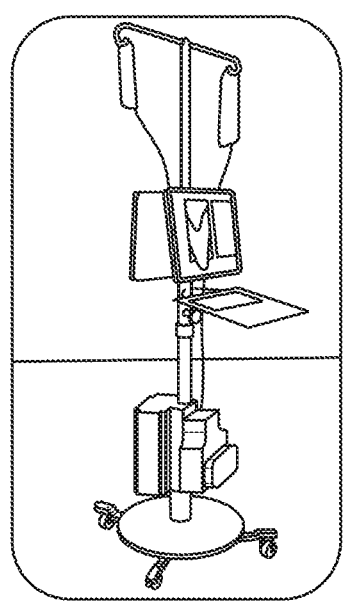
Figure 27:
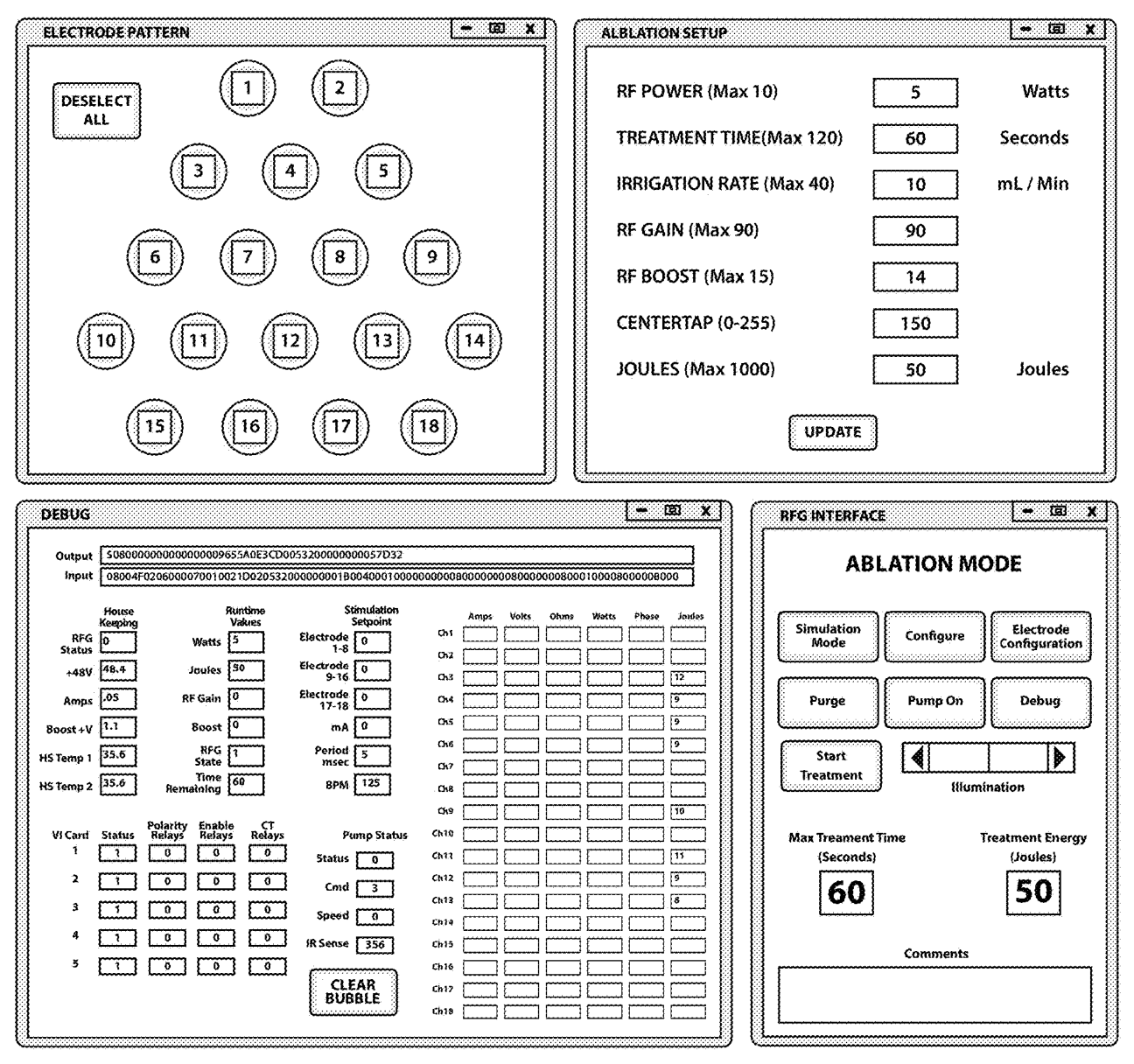

Once it has been determined, depending on the visualization information such as proper placement around a pulmonary vein or mapping electrical information, that the balloon has been properly positioned at the treatment site, an external console, generally shown in FIGS. 26 and 27, is used to activate certain electrodes and control the energy delivery parameters of the procedure. An RF generator generates the RF energy and it is delivered to the electrodes. An exemplary schematic of the electrical aspect of the embodiment shown herein is shown in FIG. 24. It is understood that eighteen channels are included while only three are shown. Alternate embodiments, not shown, may comprise more or less channels. As shown in FIG. 24, the mapping capabilities of the system are shown to the right of the electrode. Each electrode can be used in monopolar or bipolar mode, and impedance and voltage can be measured with each electrode.

The generator is configured such that electrodes can be used to map tissue, ablate tissue, and stimulate tissue, as desired. Ablation of cardiac tissue to treat aberrant signals is described generally herein and known. The generator is also configured, however, to generate and deliver electrical tissue stimulation signals to the electrodes so that the electrodes stimulate the cardiac tissue. The schematic in FIG. 24 illustrates that each electrode can be selected for either ablation or stimulation, while mapping from each electrode occurs continuously. The mapping portion includes filters configured to filter out ablation bandwidths, and other non-essential bandwidths that may be delivered or otherwise present so that mapping can occur continuously. The disclosure herein thus includes a generator configured such that each electrode can be used to both map and ablate tissue at the same time, or stimulate and ablate tissue at the same time. The system is also configured such that ablation, stimulation, and mapping can all be occurring at the same time, although the stimulation and ablation would not be occurring at any given time from the same electrode. These processes in addition can be performed sequentially.

Stimulation of the cardiac tissue can be done for a number of reasons. In an exemplary embodiment stimulation of tissue can be performed during a diagnostics procedure to make sure the electrodes are working. For example, RF energy can be delivered to a first electrode and sensed with another electrode, thereby transferring energy between pairs of electrodes to make sure the pair of electrodes is working. In this exemplary use, the stimulating energy could be delivered before the balloon makes contact with tissue or after it makes contact with tissue, as blood generally has low enough impedance so as not to prevent the diagnostic test. In an alternative embodiment cardiac tissue can be stimulated while tissue is being ablated with other electrodes. For example without limitation, three electrodes could be used to deliver ablation energy to create a lesion between the three electrodes (e.g., a linear ablation), while an electrode on one side of the lesion could be used to deliver stimulating energy to an electrode on another side of the lesion to determine if the tissue is effectively ablated. Exemplary tissue stimulation delivery signal capabilities include currents of 0 to 20 ma, pulse widths of 0 to 100 ms, repetition rates of up to 300 bpm. More preferably 0 to 10 ma, 0 to 10 ms, and up to 180 bpm. Stimulating cardiac tissue in these ways is different than mapping in that mapping measures impedance, while stimulation delivers energy configured to stimulate the cardiac tissue. The disclosure herein therefore includes methods of stimulating cardiac tissue during an ablation procedure, including before the actual ablation, while ablating, or after the ablation has occurred.

Figure 22A:
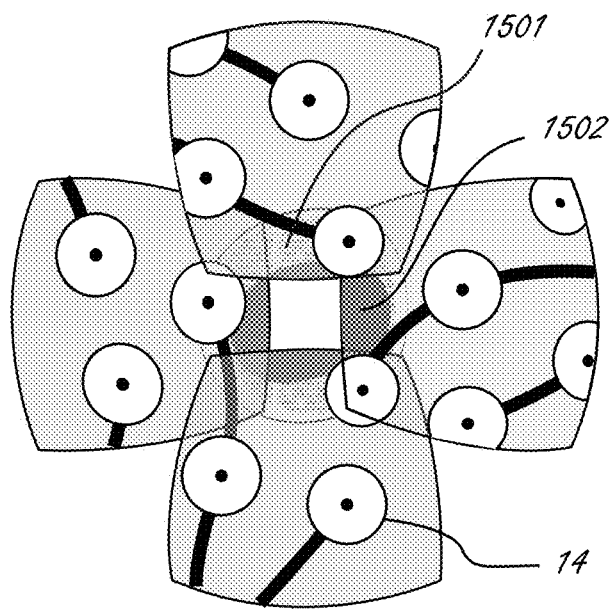
FIGS. 22A, 22B, and 22C illustrate an exemplary method of ablating cardiac tissue.
Figure 22B:
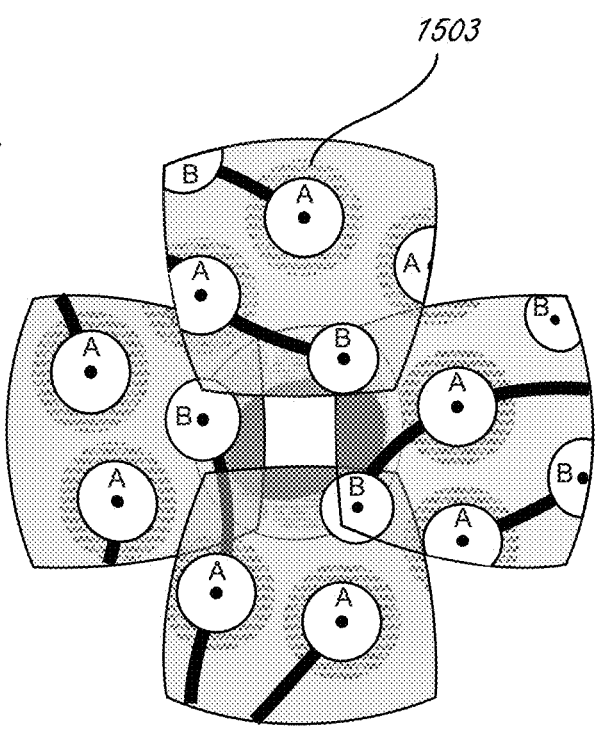
Figure 22C:
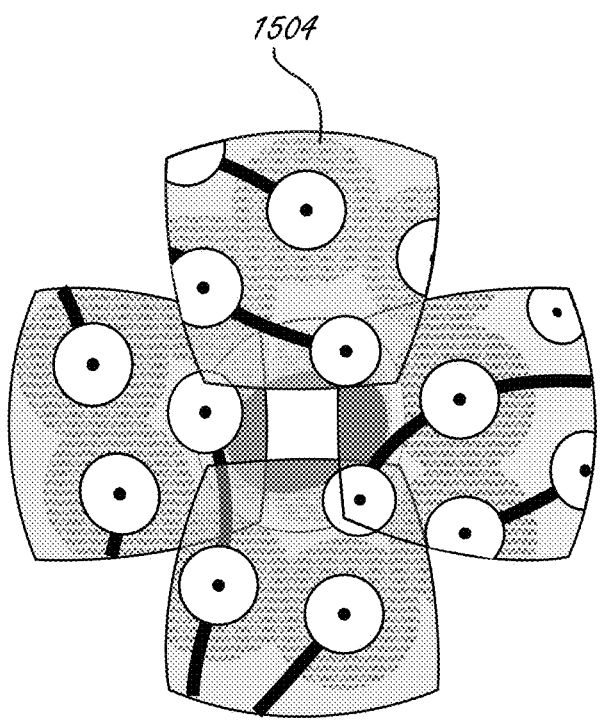

FIGS. 22A-22C illustrate an exemplary method of ablating atrial tissue around a pulmonary vein ostia to isolate the pulmonary vein, and show it from the view generated by the four field of views from the camera. FIGS. 22A-22C are meant to be the view the physician would see when using the system. Again, the blind spot in the middle can be removed depending on the camera assembly and arrangement of cameras therein. In FIG. 22A, the balloon has been advanced into contact with atrial tissue surrounding ostia 1501 of the pulmonary vein lumen 1502. None of the electrodes have been activated in FIG. 22A, although mapping procedures could also take place at this stage to assess the conduction of the cardiac tissue. FIG. 22B show certain electrodes "A" being activated and lesion regions 1503 starting to form in the tissue after the electrodes are making contact and power is applied. Electrodes designated "B" are not being activated in this example. FIG. 22C shows continued ablation of tissue and formation of lesion region 1504 that generally extends around the pulmonary vein ostia.

Figure 23A:
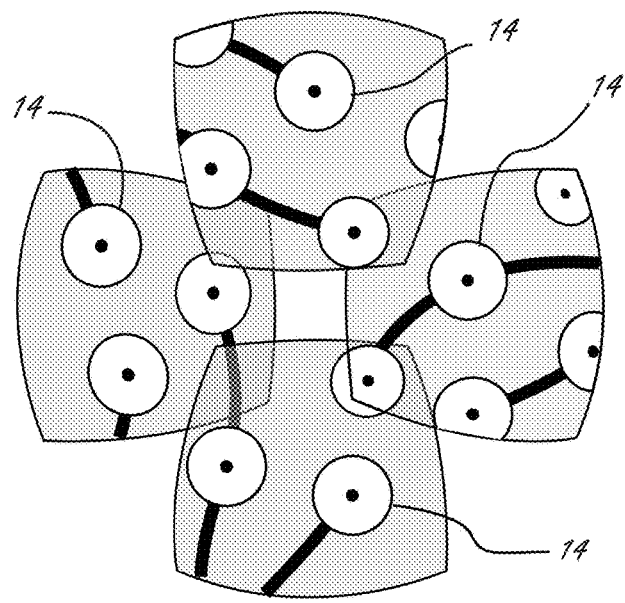
FIGS. 23A, 23B, and 23C illustrate an exemplary method of ablating cardiac tissue.
Figure 23B:
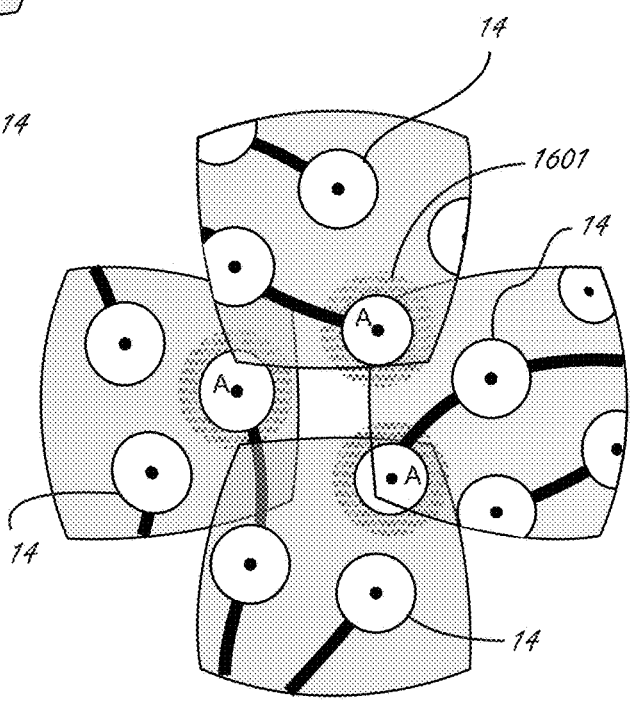
Figure 23C:
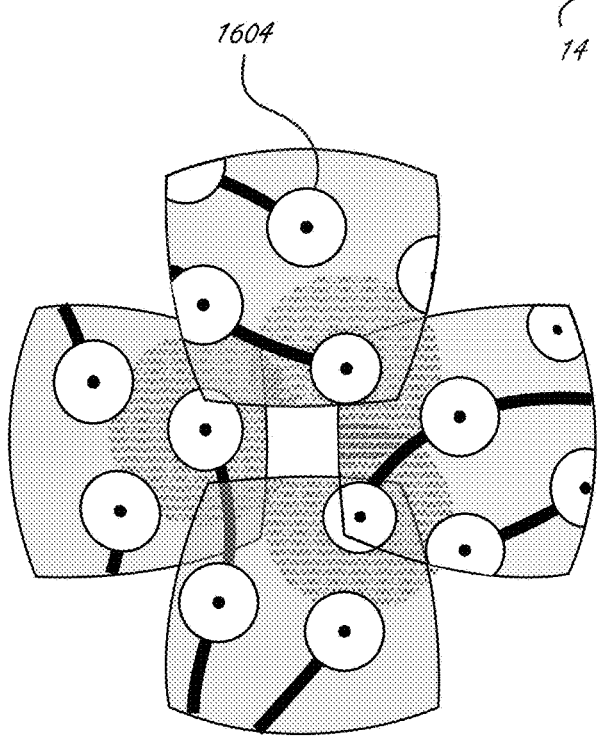

FIGS. 23A-23C illustrate an exemplary method of using the system herein to create lesion for treatment of a rotor. FIG. 23A shows the balloon advanced against cardiac tissue other than an ostia region, where none of the electrodes have been activated. FIG. 23B shows only electrodes "A" being activated, and ablation lesions 1601 starting to form where the electrodes are in contact with tissue and activated. In this embodiment, electrodes A are the distal most electrodes from each of the three flex circuits. FIG. 23C shows continued ablation and the formation of lesion region 1604 targeted at a rotor. The blind spot in the middle hides that the lesion extends over tissue that can't be seen. In alternative embodiments of use, more than three electrodes can be used to perform a rotor ablation, such as four or electrodes.

One aspect of the disclosure is a method of superimposing an image or images provided by the camera with information or an image that is an indication of at least one of a characteristic of the cardiac tissue and a characteristic of the ablation catheter. The superimposed images (or superimposed information and image) are presented to the physician in a visual display, such as a monitor, and can be part of a remote user interface. The aspect includes methods and systems adapted to superimpose images. The methods and devices herein are also adapted to obtain the information and superimpose the images.

The information that is being superimposed can be any suitable visual indicator of a characteristic of the cardiac tissue or a characteristic of the ablation catheter.

In some embodiments the information that is superimposed onto the image from the cameras is the electrical activity on the cardiac tissue contacting the expandable member.

In some embodiments the information that is superimposed onto the image from the cameras is the localized impedance of the ablation circuit.

In some embodiments the information that is superimposed onto the image from the cameras is the temperature of the cardiac tissue opposed to the balloon.

In some embodiments the camera comprising CMOS cameras are adapted to be responsive to light in the infrared range. The response can be used to estimate the temperature of the tissue before, during and or after ablation. The response can be interpreted by an algorithm and displayed superimposed to the visual light image from the cameras.

In some embodiments an accelerometer is placed at a location in, on or near the ablation balloon. The accelerometer can be used to detect the orientation of the balloon in relation to gravity. The accelerometer can produce acceleration data that is used to determine the accelerometer position in relation to an initial position. The position can be used to construct a database of locations visited by the balloon and/or information collected by the electrodes on the balloon and/or RF power applied to the balloon electrodes. The collection of information can be used to reconstruct a model to provide guidance to the physician in relation to the locations that are treated and locations that need to be treated.

FIG. 29 illustrates exemplary information and indicators that can be superimposed on the images from the cameras. Indicators 402 and 404 are examples of way to convey temperature of the tissue adjacent an electrode. For example, indicator 402 is a series of lines indicating qualitatively the temperature, such as "medium." Indicator 404 is a series of intersection lines and can indicate "high" temperature. Any type of visual indicators can thus be used to indicate the qualitative temperature of one or more tissue regions adjacent any of the electrodes.

Superimposed information 406 provides a qualitative indication of tissue temperature, in this example, 99 degrees. Information 406 is next to the image of the electrode, whereas information 408 is information that is on the electrode image. Indicator 410 is a red color superimposed on top of the electrode, providing a qualitative indication of "hot." Information 414 and 416 are superimposed to indicate that the respective electrodes are "on" and "off."

In some embodiments the superimposed information is all the same type of information. For example, each electrode can, at the same time, be superimposed with information indicating the temperature of tissue. In other embodiments, the type of superimposed information can be different for any of the electrodes.

Additional examples of the type of information that can be superimposed include electrical impedance, which can be visualized quantitatively or qualitatively using any of the indicators herein (e.g., color, numbers). Additionally, mapping signals can be superimposed on the camera images as well.

FIG. 30 represents an exemplary flexible circuit for application to the outer surface of a balloon, with a thin polyimide substrate 101 approximately 0.002-0.003" thick and a total structural thickness between 0.004-0.006".

The outline is that of the final ablation pads 102 (only the large square and the triangle). Apertures 103 are for saline flow. Circuit traces 104 terminate in exposed areas on the ablation pads. Conductive silver paint is used to create the ablation pad geometry and the exposed trace provides conductivity.

Alternately, a black adhesive may be used to darken the areas under silver painted ablation pads 102 to prevent reflections inside the balloon, as is described herein. One method of employing polyimide substrate 101 can eliminate the black adhesive providing a thinner and more compliant mounting surface.

A dielectric area 105 is provided to prevent cross talk and conductivity to the blood or other medium. The proximal side of the flex circuit has two small solder pads 106 where the wires are attached.

An assembled flexible circuit as represented in FIG. 30 can be affixed to balloon 201 as shown in FIG. 40, such balloon being located around a central stem 202, and such stem having a system to capture the image of the internal surface of the balloon (not shown) and transmit such image to a display outside the patient. An optional long protrusion 203 distal to the triangle pad which wraps around the front of the balloon to create a physical anchor for the circuit.

Additionally an accelerometer 204 is placed at a location in, on or near the ablation balloon, such accelerometer can be used to detect the orientation of the balloon in relation to gravity and to construct treatment relevant data sets as described herein.

When the physician moves the catheters as described herein, more specifically, when the physician rotates the system around the longitudinal axis of the catheter, the image display will show the internal surface of the balloon fixed and everything outside the balloon (e.g., cardiac tissue) moving. This is due to the fact that the cameras, in the embodiments herein, are fixed in relation to the catheter and balloon system.

FIGS. 32A and 32B illustrate a composite view as described herein from a four camera array as presented to the user on a display. The images are mapped to a composite image representing the arrangement and orientation of cameras carried by the balloon on the shaft within the balloon. The mapping registration relies on mapping common features within each camera field of view over each other where there are common features within two or more images. As illustrated, one electrode, the orientation registration electrode, is identifiable by a marking in the shape of an asterisk (as shown) which has been printed on the balloon prior to the electrode and is visible to the camera. In other embodiments each electrode may be marked with its own unique identifier or some or all electrodes may have different shapes which help to identify them. The common fixed features (relative to the cameras) include traces, electrodes and other fixed markings. FIG. 32A illustrates an initial image taken just after burns 502 and 504 created by electrodes 514 and 510 respectively. The balloon is centered around a pulmonary vein 506. FIG. 32B illustrates a second image captured by the camera array after the balloon is rotated. Each composite image has been processed such that the fixed features (relative to the cameras) are mapped to the user display in a fashion such that the registration mark (and hence the entire image) is rotated an amount equal and opposite to the rotation measured for the center of mass of one or more of the anatomical features around the center of the composite image such as burns 502 or 504. By so doing the image of the fixed features will rotate while the portion of the image behind the fixed features will remain fixed as the balloon is manipulated.

Disclosed here therefore is a system to, through image processing, show the internal surface of the balloon rotating while maintaining still, or fixed, the image of everything outside the balloon (e.g., tissue). In this manner, the image of everything that is not part of the catheter will remain fixed, and everything that is part of the catheter will be shown in the video to rotate. In this alternate embodiment, the image that the user views shows the fixed features (e.g., electrodes) being rotated while anatomical features remain still. The anatomical features are the non-fixed features or non-balloon related features in the tissue such as, represented in this view, the pulmonary vein, and the images of burns created by ablation. This is accomplished even though the fixed features move as the camera moves. Keeping the tissue fixed for the user, and having the device components move allows the physician to better control the movement of the device relative to the tissue. To facilitate this procedure the mean rotation of the center of mass of one or more of the key anatomical feature are calculated relative to the location of the fixed features. The mean or other suitable representation of the rotation(s) is then used to rotate the composite image as presented on the user display.

Figure 28:
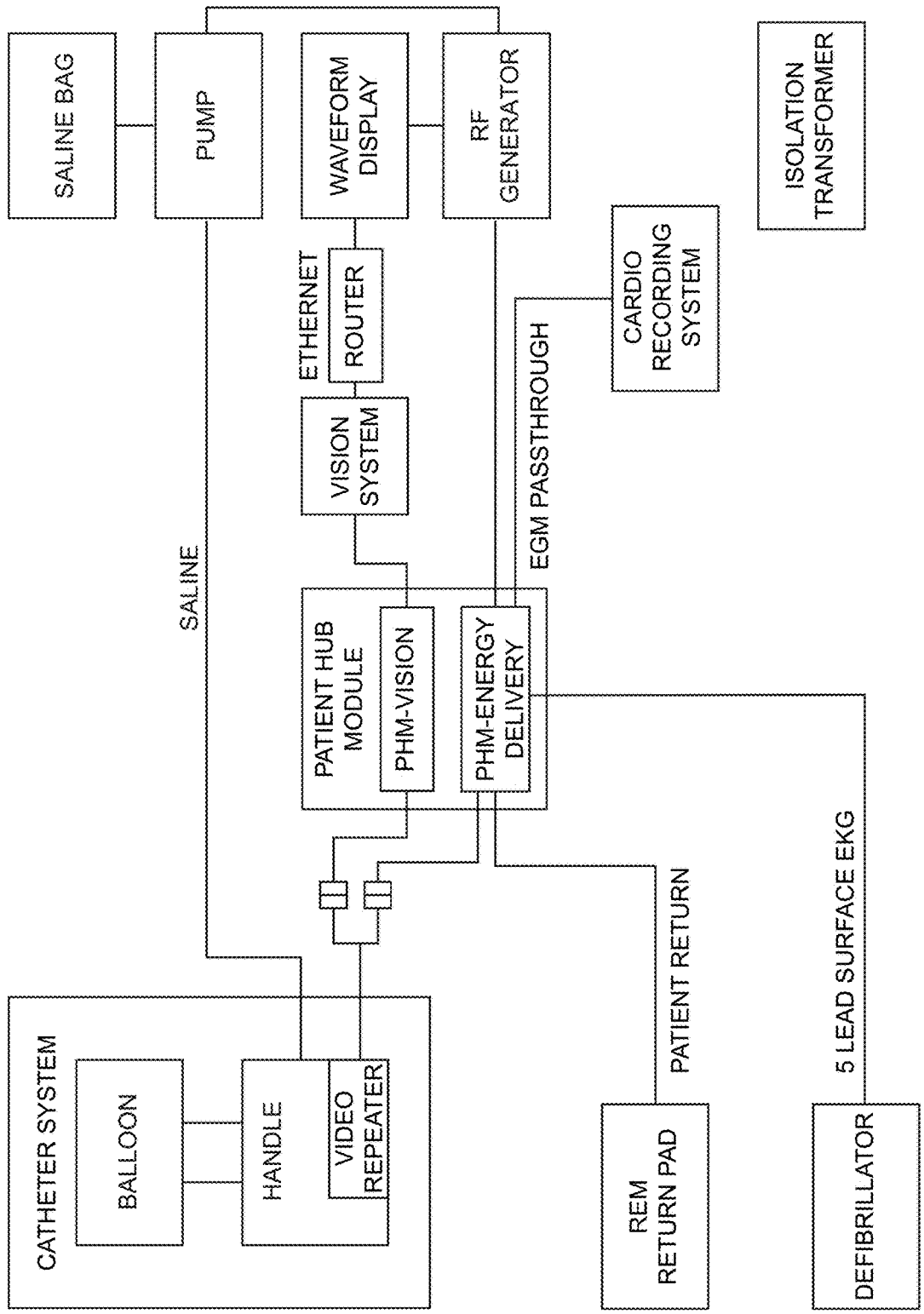
FIG. 28 illustrates an exemplary block diagram of a cardiac ablation system.

FIG. 28 illustrates an exemplary block diagram of a cardiac ablation system, details of which are described herein. Any of the system components in FIG. 29 can be incorporated and used with any of the individual components described herein.

The number and arrangement of the electrodes disposed on the expandable member, each of which is individually addressable and can be used to deliver energy in either monopolar or bipolar mode, provides for a wide variety of lesion formations without having to remove and insert a separate RF catheter. The exemplary methods shown in FIGS. 22A-C and 23A-C are merely exemplary. Linear lesions and arc lesions are additional examples of lesion shapes that can be created depending on the desired ablation procedure. In the specific example provided herein, there are eighteen individually addressable electrodes disposed on substantially the distal portion of expandable member 10. Any of them can be energized while others are not, allowing for many different lesion formations to be made in cardiac or other tissue for treating cardiac arrhythmias. Any of the electrodes can be used in bipolar mode with any other electrode as well. Depth and width of lesions may be controlled by choosing and/or varying what combination of electrodes are being used in bipolar and monopolar configurations. Monopolar configuration creates deeper, narrower lesions, and bipolar configuration creates shallower, wider lesions.

One of the advantages of the devices herein is that the number and arrangement of electrodes allow for a wide variety of lesion formations without removing and inserting a new catheter. And the visualization system allows for the entire procedure to be visualized.

Figure 7:
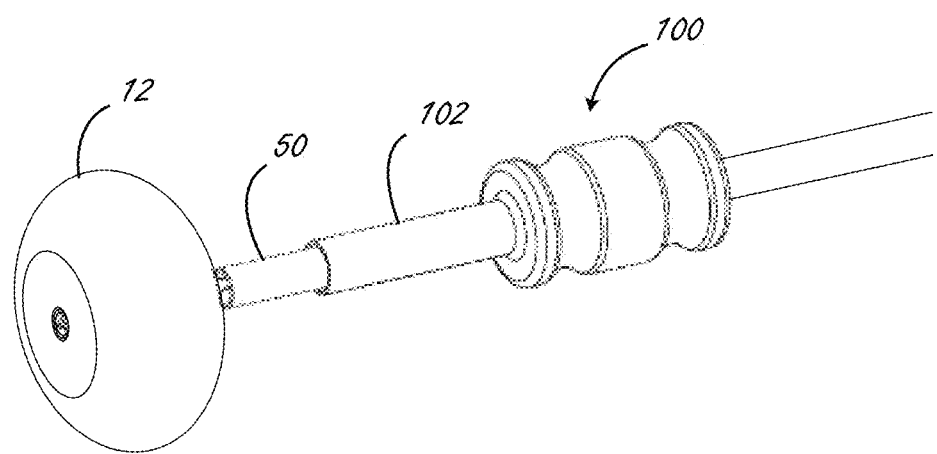
FIG. 7 illustrates the distal end of a device incorporating a slideable sheathing tool comprising a sheathing tube.

FIG. 7 illustrates the distal end of the device incorporating a slideable sheathing tool 100 comprising sheathing tube 102. In use, balloon 12 is collapsed as previously described and then the sheathing tool is slid over the collapsed balloon. The sheathing tube 102 is then fit into the delivery catheter, not shown. The sheathing fixture is then removed, leaving the collapsed balloon within the deliver catheter ready for advancement to the delivery site.

One aspect of the disclosure is a delivery catheter comprising concentric sheaths as a steering mechanism with a mapping system built into the distal tip, where a mapping basket resides during delivery in the space between the two concentric shafts and on delivery is pushed forward out into the heart chamber. Examples of deployable mapping baskets are described above. An ablation catheter may then be delivered through the delivery catheter with the mapping basket in place. Target locations for ablation can then be identified using the electrodes on the mapping basket and target locations are then ablated with the ablation catheter. The location of the ablation catheter may in addition be identified and verified by the mapping basket.

One aspect of the disclosure is an ablation catheter that includes an electrode structure that is about 1 cm to about 5 cm in diameter and resides on the end of an inflatable or expandable structure and may comprise any of the following: an ablation catheter with a balloon carrying multiple electrodes. In some embodiments the multiple electrodes are used alternatively as a single ablation electrode then as a set of individual impedance sensing electrodes capable of monitoring the inter electrode impedance. Such measurements are useful in characterizing the efficacy of the burn resulting from the ablation and/or mapping the ablated are before or after the burn. In some embodiments contact pressure sensitive electrodes may be incorporated as a means of verifying appropriate contact of the electrode to the cardiac tissue. In many embodiments irrigation is provided as described elsewhere herein, wherein the irrigation system incorporates a pressure sensor. In such embodiments contact pressure may be inferred from changes in pressure within the irrigation system associated with increasing the outflow resistance at the irrigation outflow ports press against tissue. In other embodiments a balloon within a balloon configuration is used such that irrigation pressure may be isolated from inflation pressure. The change in pressure within the inflation system then is directly correlated to the contact pressure. In another alternative cooling may be provided by recirculation within the balloon as opposed to irrigation.

In some embodiments the contact pressure of an electrode is measured by impedance matching. An alternate means of characterizing the quality of lesions is to measure changes in acoustic impedance in the ultrasonic pass band. The acoustic impedance will be changed from that of normal tissue both as a function of temperature and denaturation. In such an embodiment a forward looking US transponder can be incorporated in the balloon or on the surface of the balloon. Such a sensor may be embodied as an array of one or more transponders, an array of one or more transmitters and an array of one or more receivers, or a single transponder.

In an alternate embodiment temperature of the lesion may be monitored by microwave radiometry.

Figure 33:
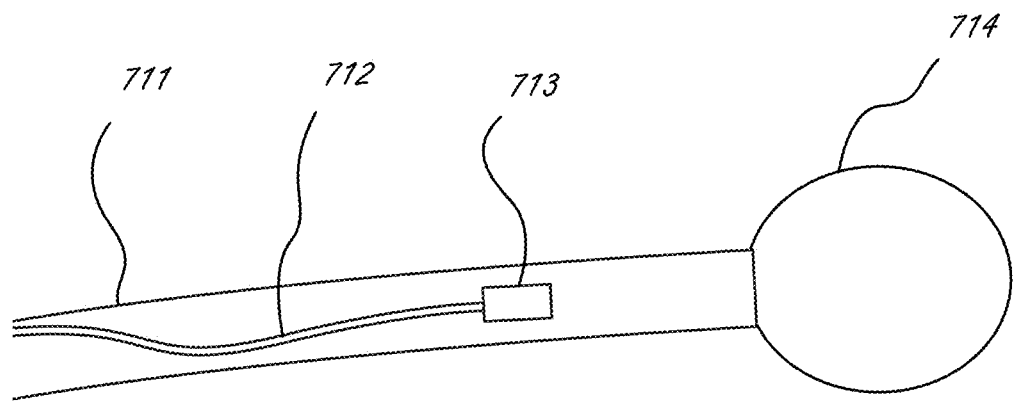
FIGS. 33 and 34 illustrate an exemplary embodiment of an ablation catheter wherein the balloon is configured for contact (physical) measurements.
Figure 34:
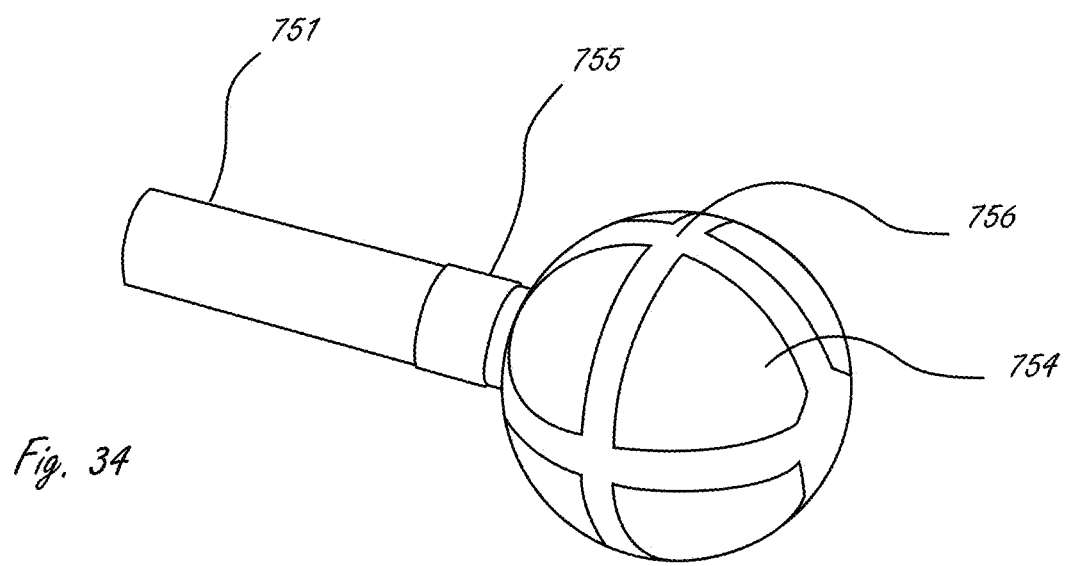

FIGS. 33 and 34 illustrate an exemplary embodiment of an ablation catheter wherein the balloon is configured for contact (physical) measurements. Contact pressure of the balloon and therefore electrodes as characterized by variations in the internal balloon pressure resulting from irrigation holes in the balloon which pass through electrodes being occluded as the electrode is pressed against the tissue. Pressure will increase transiently as the balloon is pressed against the tissue and then reach a new equilibrium associated with any decrease in outflow resistance associated with the occlusion or partial occlusion of irrigation ports. This contact pressure can be mapped by previous experiments to an electrode contact surface area.

A visual contact monitor comprised of a camera within the expandable structure monitors contact as a change in the visual appearance of transparent windows in the balloon.

The changes in visual appearance result from differences in the appearance of blood and tissue.

Contact monitoring may be used control power delivery. Measurements of electrode contact obtained by any of the means described herein can be used to mediate the amount of power delivered to an electrode. One control algorithm limits power to an electrode such that the power per area of contact surface is maintained at a constant level.

FIG. 33 illustrates a prototype balloon configured for contact measurement. Balloon 714 is affixed to the end of shaft 711. Strain gages 713 is affixed to shaft 711 and leads 712 which are interfaced with a strain gage amplifier not shown. There are two additional strain gages affixed to the shaft at plus and minus 120 degrees. FIG. 34 is a representation of a similar device in which all three strain gages are configured in strain gage assemble 755 on shaft 751 which comprises the leads to the strain gage assembly. Balloon 754 comprises electrodes 756. In alternate embodiments the pressure of enclosed volumes of fluids or gels arranged in cells near the proximal attachment of the balloon may be monitored via one or more pressure sensors. In yet other embodiments the strain gages may be replaced with displacement sensors. As indicated above measurements from such sensing systems can be mapped to an estimate of electrode contact surface. The balloon of FIG. 33 is 2 cm in diameter and that of FIG. 34 may be 1 to 3 cm in diameter. The configuration of electrodes on the device of FIG. 34 comprises eight electrodes. Such a small profile allows small delivery size and precise maneuverability. Such a system is compatible with a single RF generator and may comprise an irrigation system, not shown, to minimize unwanted injury.

The use of RF ablation in the treatment of atrial fibrillation as described herein poses the risk of thermal damage to the esophagus. This disclosure includes systems and methods to measure temperature of the esophageal wall during RF ablation. In some embodiments a balloon is placed in the esophagus and inflated to make contact with the esophageal wall. A pattern of temperature sensitive material deposited on the balloon measures the temperature change induced by RF ablation. An electronic circuit senses the temperature change to alert the operator.

A thermistor is a type of resistor whose resistance changes with temperature. A negative temperature thermistor (NTC) resistance decreases with temperature due to increased mobility of electrons and subsequent increased ability to conduct current. Commercial NTC thermistors are fabricated from common metal oxides of manganese, nickel, cobalt, iron, copper and titanium using basic ceramics technology. In the basic process, a mixture of a metal oxide powder and suitable binder are sintered in a suitable atmosphere and configuration to achieve the desired temperature coefficient characteristics.

Initial NTC thermistors were fabricated using silver sulfide (Ag2S) powder. More recently, miniaturized, planar silver ion-specific electrodes based on silver sulfide have been fabricated entirely by screen-printing using low-temperature curing polymer pastes and polyester substrates in the form of flexible foils (Sensors and Actuators B 96, 2003, 482-488). Ostensibly, in addition to sensing silver ions, such constructions may also be sensitive to temperature.

A pattern of temperature-sensitive material is deposited on a flexible balloon which is sized to occlude the esophagus. The pattern includes two flexible thermistors (flextors). The two flextors are used in a battery-powered Wheatstone bridge electrical circuit to measure the differential temperature of the two flextors. When placed in the esophagus, the differential temperature induced by RF heating is sensed. If a temperature differential exceeds a limit, the circuit alerts the operator to modify the RF ablation treatment.

Figure 35A:
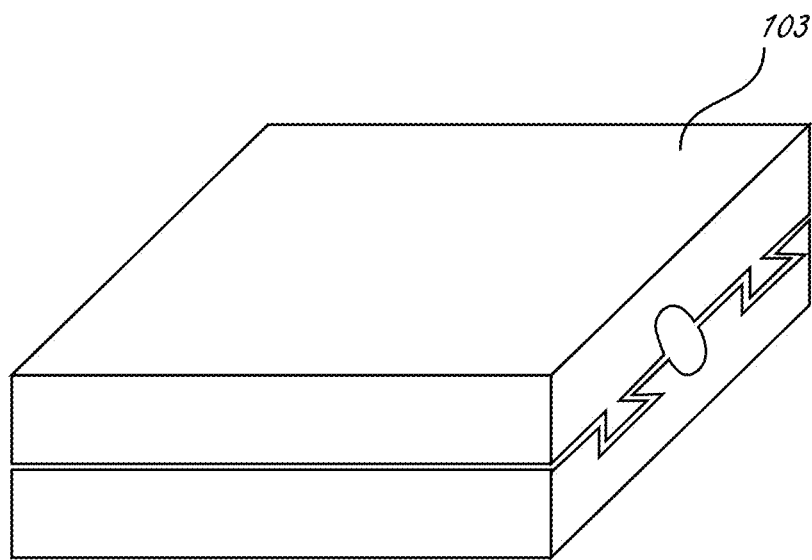
FIGS. 35A, 35B, and 35C illustrate a sheathing device that can be used to sheath an electrode assembly for minimally-invasive delivery.
Figure 35B:
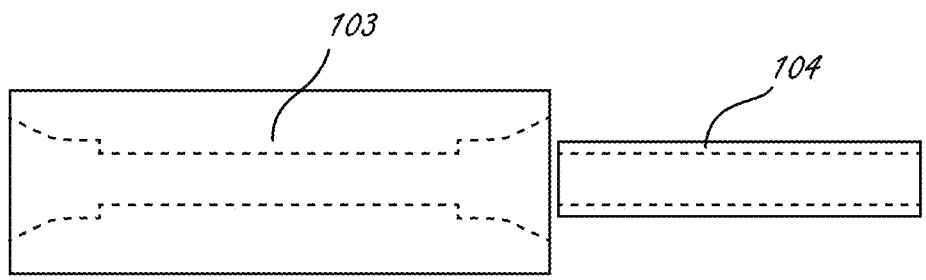
Figure 35C:
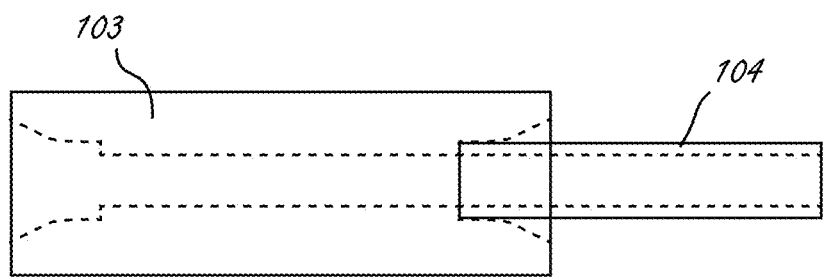
Figure 36A:
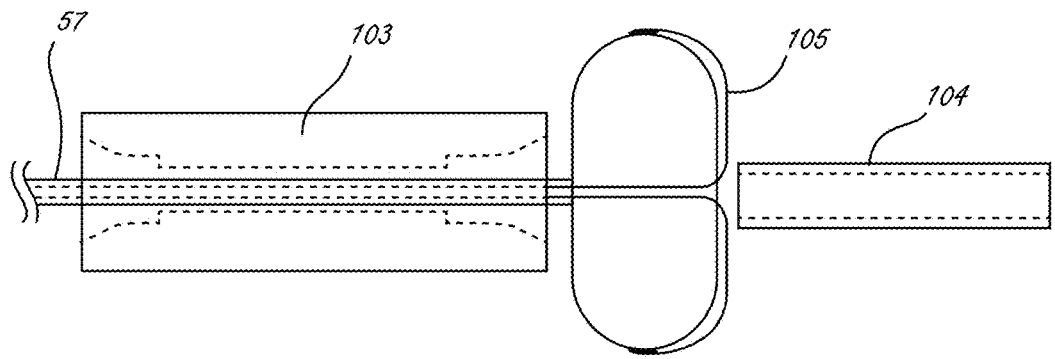
FIGS. 36A, 36B, 36C, 36D, 36E, 36F, 36G, 36H, 36I, 36J, 36K illustrate a method of sheathing an electrode assembly for minimally-invasive delivery.
Figure 36B:
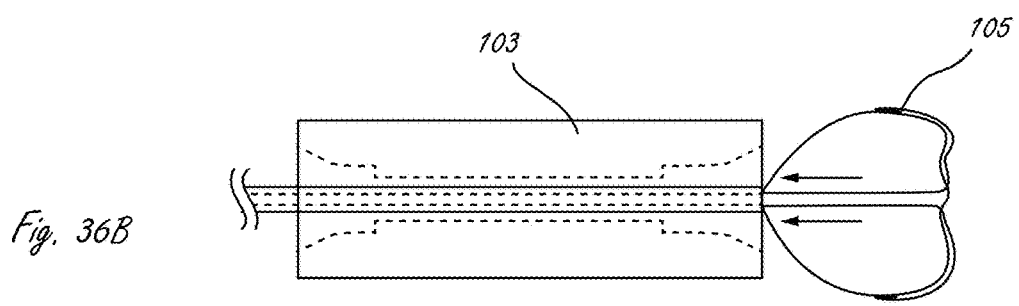
Figure 36C:
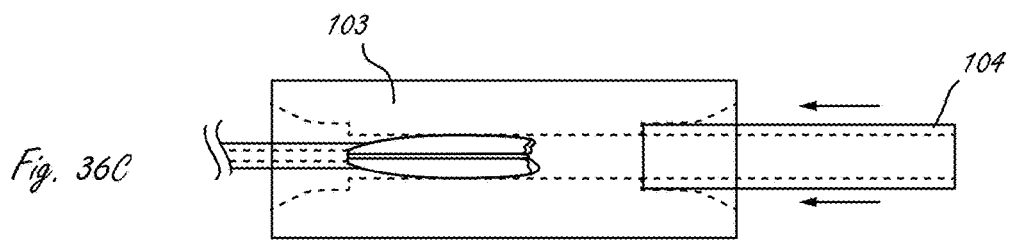
Figure 36D:
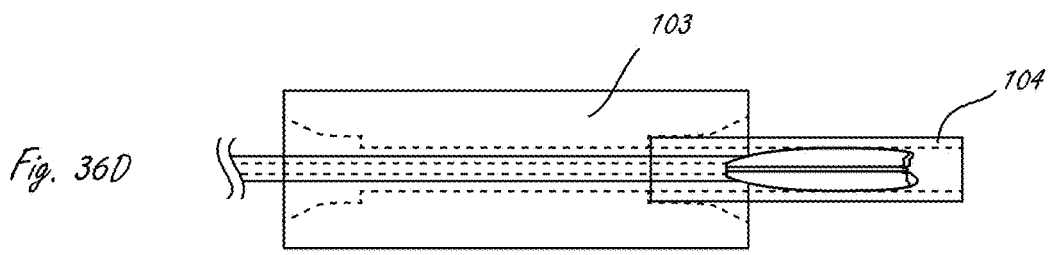
Figure 36E:
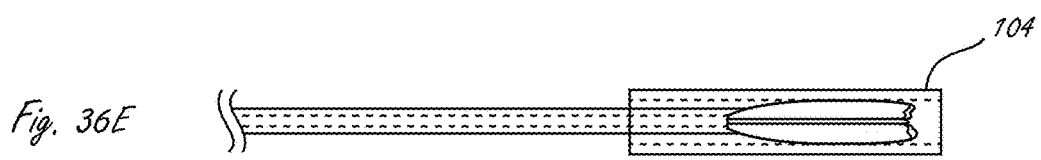

The expandable member, which in some embodiments can be an electrode assembly, can be sheathed using a sheathing fixture 103 and introduced into a sheath that is placed at the appropriate entry point, the femoral vein for example (see FIGS. 35A-35C). The sheathing fixture 103 can be a block with a predefined internal diameter for the electrode assembly 105. The fixture 103 can be manufactured as two halves that are slidable and interlockable to each other as shown in FIG. 35A. A sheathing tube 104 can be used in conjunction with the sheathing fixture 103 in that the tube 104 can slide into the sheathing fixture 103 until it reaches a hard stop as shown in FIGS. 35B and 35C. The inner diameter of the tube 104 can match that of the fixture 103. To sheath the ablation assembly 105, the catheter can be placed within the sheathing fixture 103 such that the assembly 105 is outside of the fixture 103 at one end as shown in FIG. 36A. The shaft 57 can also be placed with the two halves of the sheathing fixture 103 still separated. The assembly 105 can be pulled into the inner portion of the sheathing fixture 103. The tube 104 can be inserted into the fixture 103 until it reaches a hard stop. The shaft 57 and the electrode assembly 105 can be pushed into the tube 104 and seated within the tube 104. Once the assembly 105 and shaft 57 are securely sheathed into the tube 104, the fixture 103 can be removed from the assembly 105 by separating the two halves of the sheathing fixture 103. The sheathing tube 104 can be used to introduce the assembly 105 into a sheath that is placed to reach the desired target tissue. The assembly 105 is then pushed out of the sheathing tube 104 and travels within the introducer to reach the target site. The sheathing tube 104 remains proximal to the assembly and does not travel within the introducer sheath, not shown.

Figure 36F:
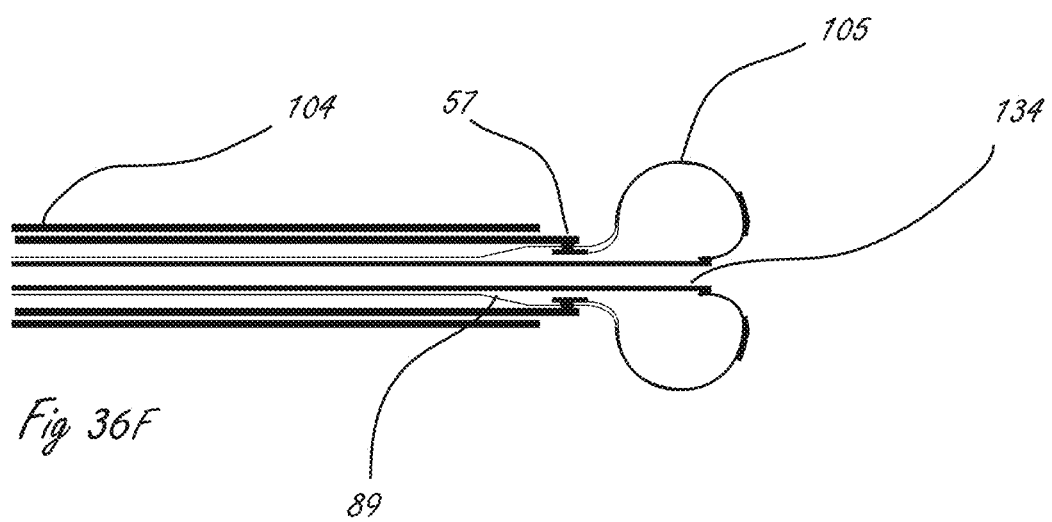
Figure 36G:
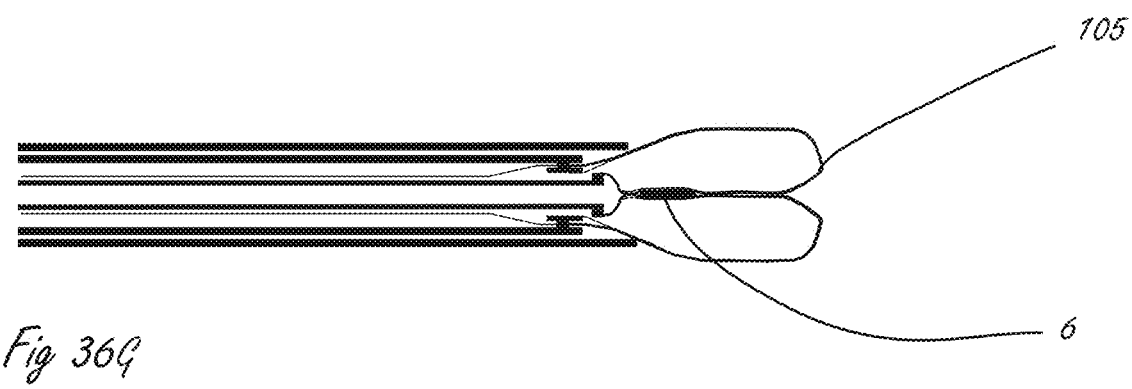
Figure 36H:
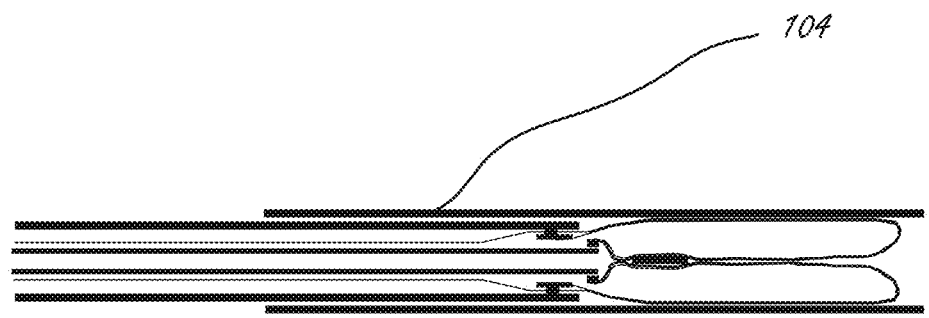

An alternate way of sheathing prior to introduction to the introducer is illustrated in FIGS. 36F-36H. The three primary stages of this process are represented in FIGS. 36F-36H and are described as follows. In this embodiment an alternate sheathing tube 104 is mounted on the outer shaft 57 at the time of manufacture as shown in FIG. 36F. The sheathing tube 104 and assembly 105 are moved relative to one another such that assembly 105 is collapsed by alternate sheathing tube 104 as indicated in FIG. 36G. As the relative motions are continued electrode assembly 105 is captured and contained within the alternate sheathing tube as shown in FIG. 36H. The alternate sheathing tube 104 and electrode assembly 105 are then introduced through an introducer valve 126 into the introducer sheath 127. Sheathing tube 104 may be a short section which interfaces with the proximal section of outer shaft 57, or may be close to the entire length of the outer shaft 57 such that it can be operated from the handle and can be used while the electrode assembly 105 is resident in within the luminal system under treatment.

Figure 36I:
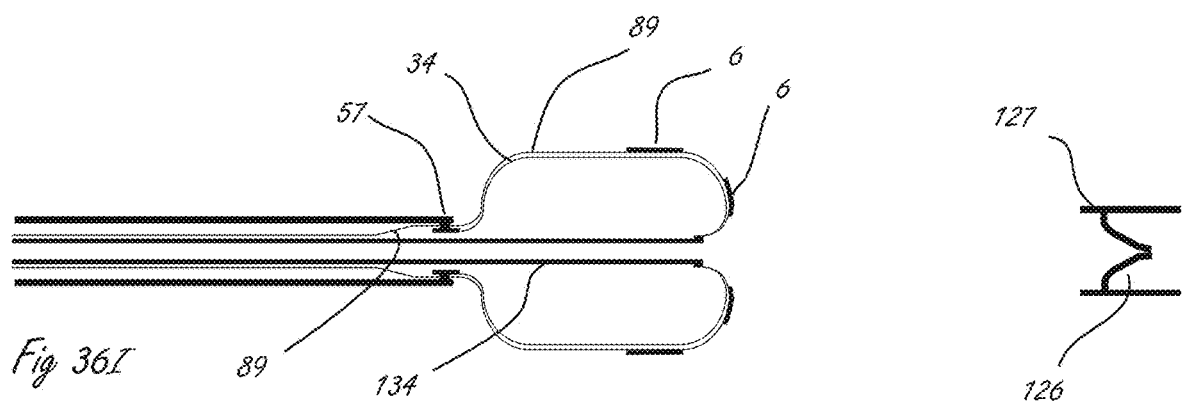
Figure 36J:
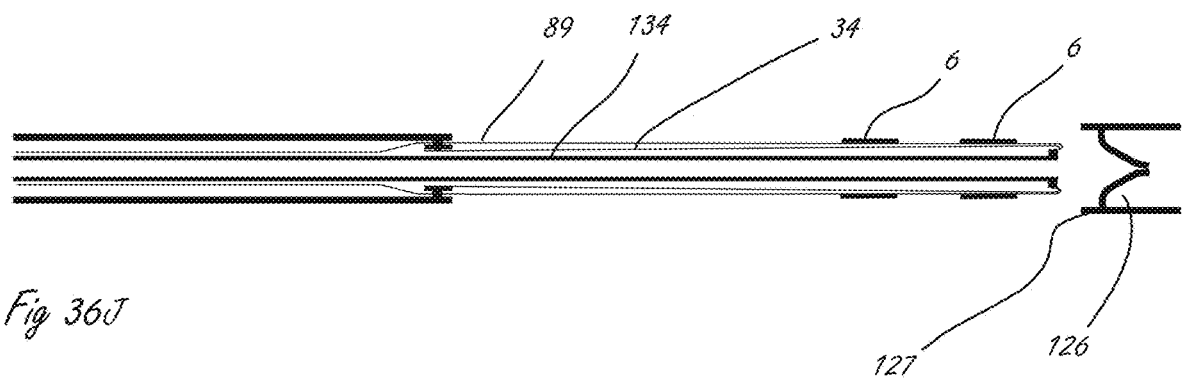
Figure 36K:
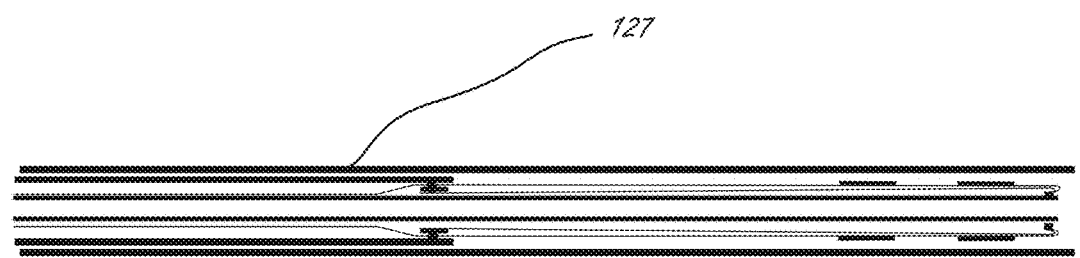

In yet another embodiment a sheathing tube may or may not be required. This embodiment is represented in FIGS. 36I-36K. In this embodiment the inner shaft 134 and the outer shaft 57 are moved relative to one another such that the electrode assembly 105 is shifted from its expanded configuration to a delivery configuration as indicated in the transition pictured from 36I-36J. As illustrated in FIG. 36K, electrode assembly 105 is shifted into introducer sheath 127 through introducer valve 126 and the device is ready for transport to the treatment site. Alternately, the device in the configuration of FIG. 36J may be delivered with a sheathing tube such as those described herein.

The assembly 105 can be delivered to the left atrium and the membrane expanded and placed at the antrum of one of the pulmonary veins. The overall shape of the membrane can be visualized using the electrodes themselves as the conductive metallic material of the electrodes can provide visualization under fluoroscopy. The radiopaque markers can be used to determine exact location of each electrode based on the marker orientation. The mapping electrodes can be used to measure initial electrical signals and can later confirm electrical conduction block post ablation. The user can select which electrodes to turn on, which ones to leave off, and which ones to set to a higher or lower power setting based on their contact with the tissue. The various methods of contact detection as described above, or a fiber optic, can be used to confirm contact of the electrodes with the tissue. The device is then set to the appropriate power and temperature settings, irrigation turned on to the desired level, and energy transmission initiated. The mapping electrodes can be used now to determine successful conduction block. Once conduction block is achieved, the catheter and moved over to the next target location, another pulmonary vein or atrial wall, for ablation.

Figure 37A:
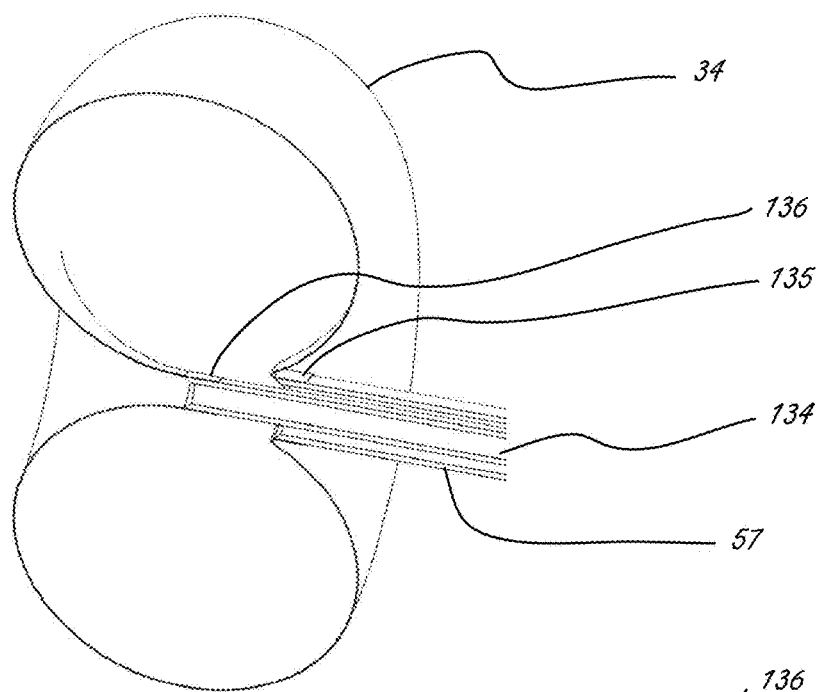
FIGS. 37A, 37B, and 37C illustrate two embodiments of an electrode supporting membrane and shaft interface.
Figure 37B:
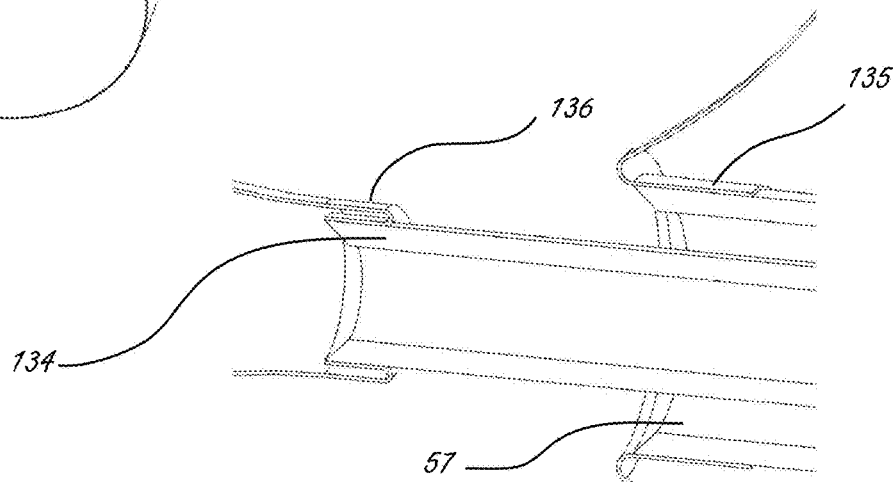
Figure 37C:
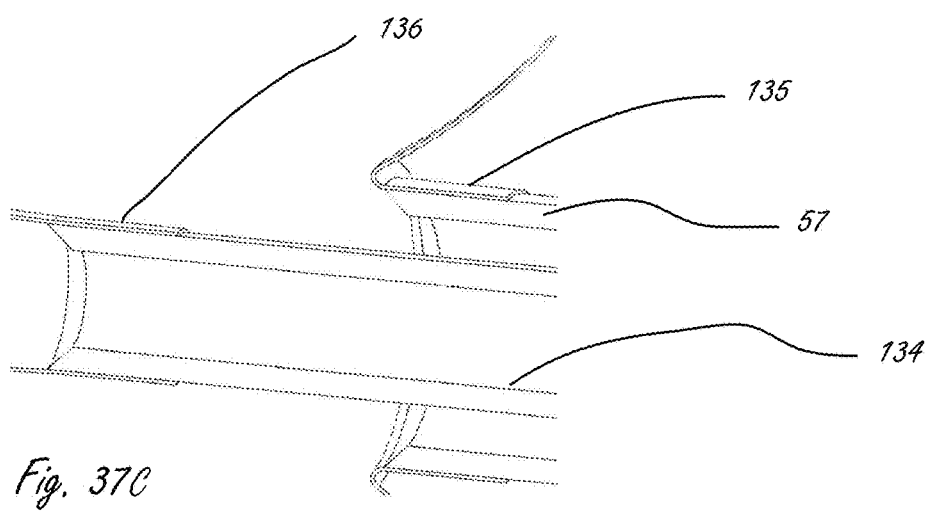

In FIGS. 37A-37C, 38A and 38B are illustrated various configurations by which catheter shafts may be interfaced to the expandable membranes 34 associated with the electrode assembly 105. FIG. 37A and detailed views in FIGS. 37B and 37C illustrate how the outer diameter (OD) of an inner shaft 134 and an outer shaft 57 may be interfaced to the various surfaces of an expandable member 34. FIG. 37B illustrates an expanded view of an interface in which the outer surface 135 of the expandable membrane 34 is interfaced to the OD of the inner shaft 134 and the inner surface 136 of the expandable membrane 34 is interfaced with the OD of outer shaft 57. In FIG. 37C, the interface to the outer shaft remains the same as that illustrated in FIG. 37B, but the inner surface of expandable membrane 34 is interfaced with the OD of inner shaft 134. Although not shown, a single shaft may also be used to interface with the distal and proximal interfaces of the expandable membrane 34. In this embodiment, a spacer can be used at the distal end. Alternatively, both interfaces on the expandable structure can be fabricated at the same inner diameter (ID).

Figure 38A:
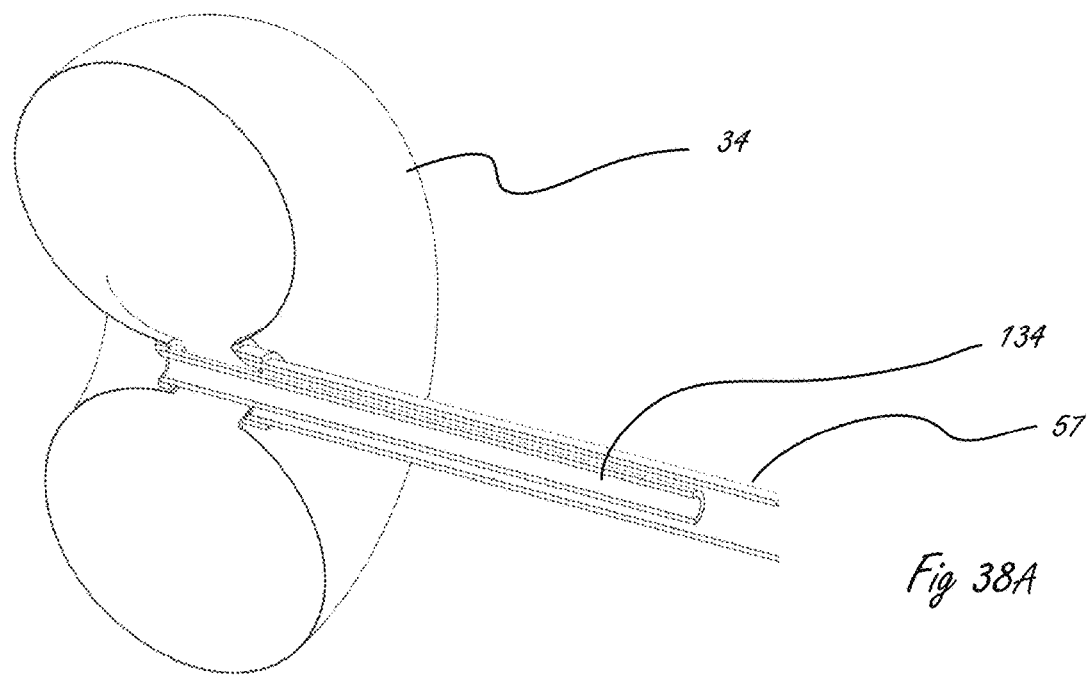
FIGS. 38A and 38B illustrate an alternate embodiment of an electrode supporting membrane and shaft interface.
Figure 38B:
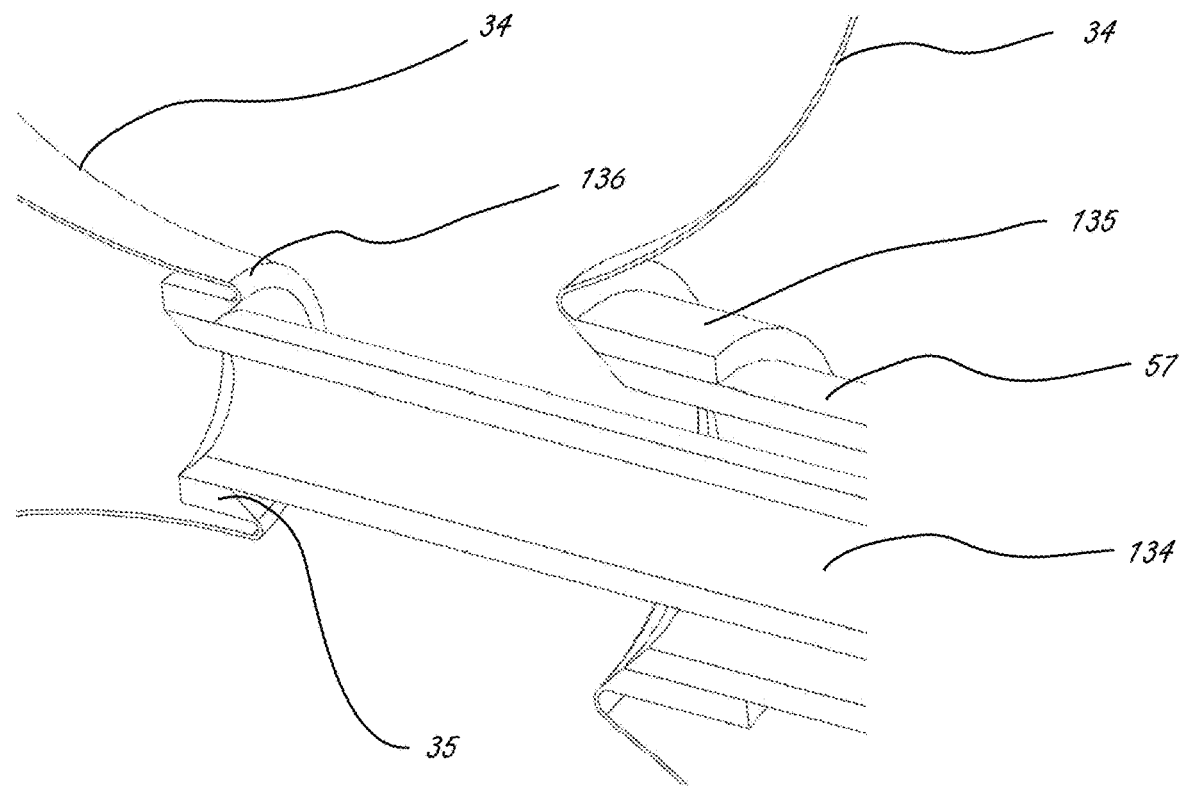
Figure 39A:
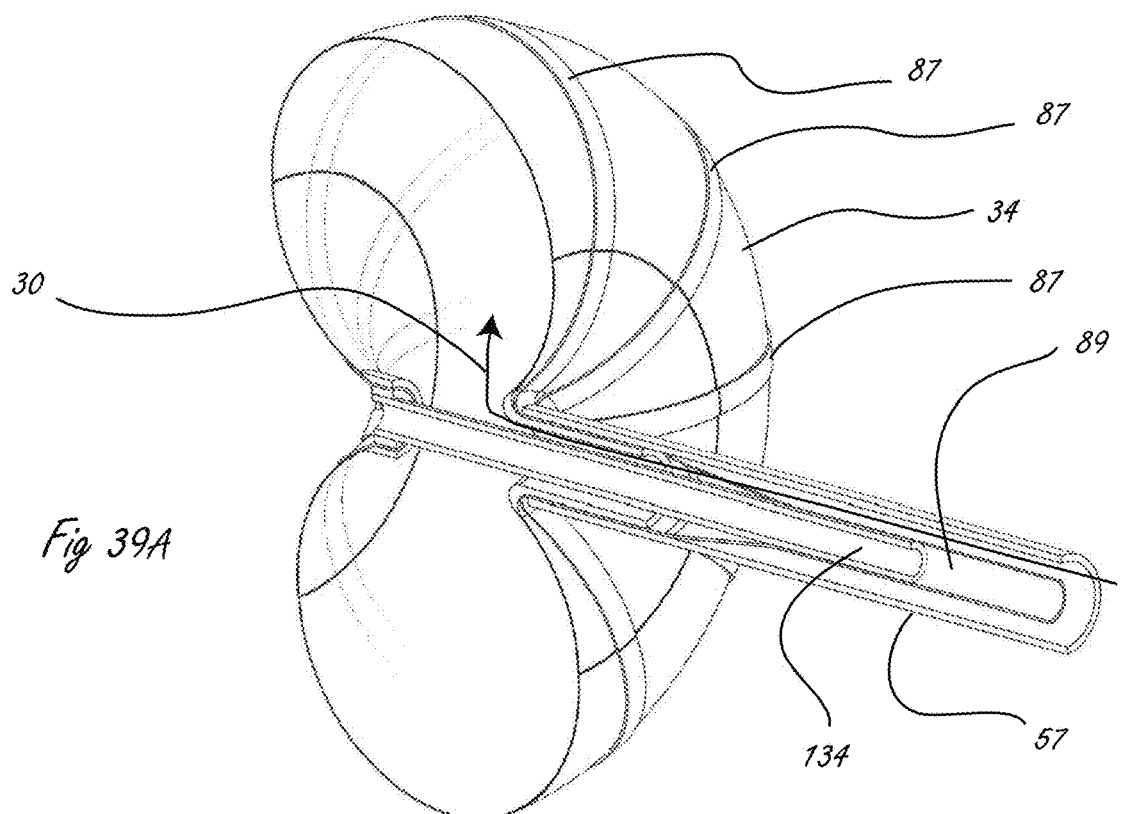
FIGS. 39A, 39B, and 39C illustrate an alternate embodiment of an electrode supporting membrane and shaft interface.
Figure 39B:
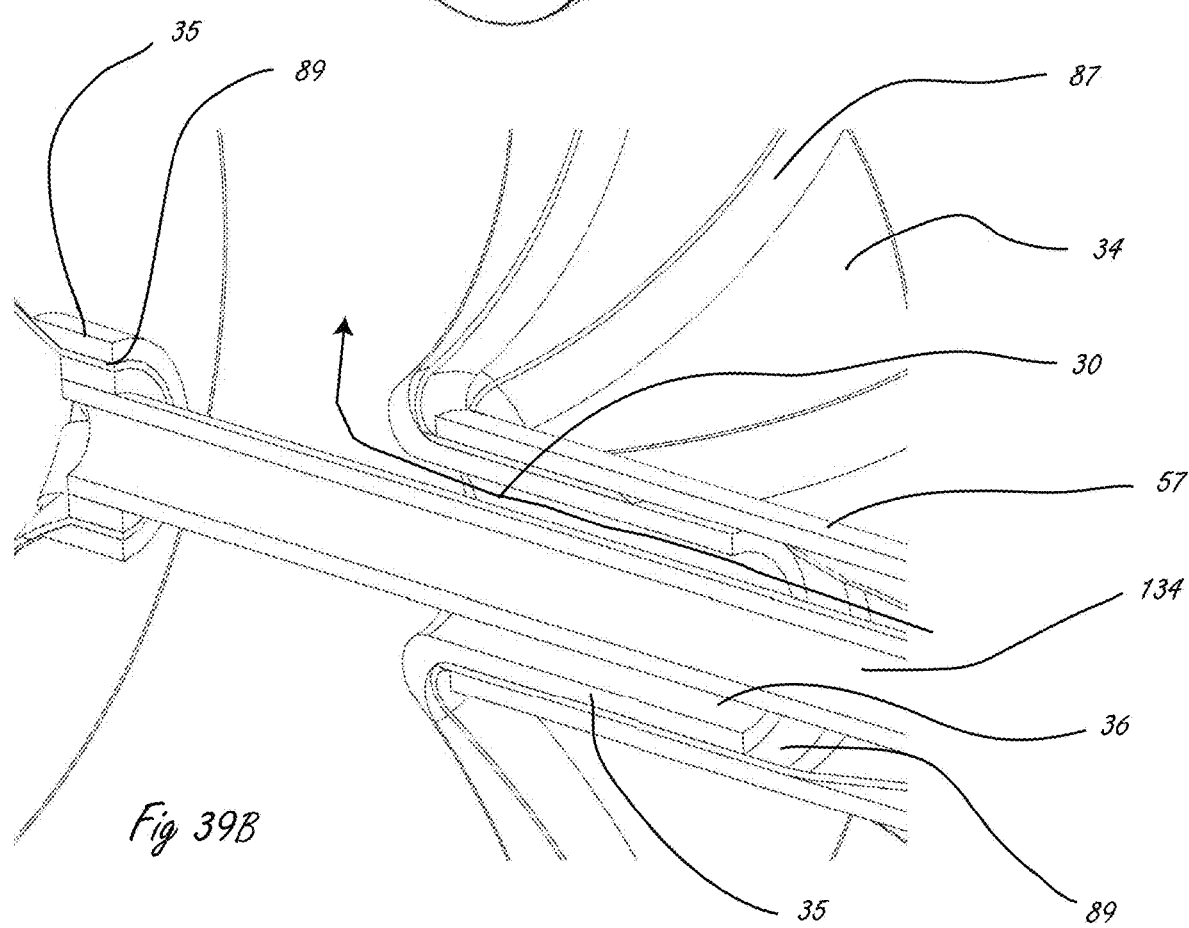

FIGS. 38A and 38B illustrate the interface of FIG. 37B where the expandable member portion of the interface incorporates a thickened section 35. FIGS. 39A and 39B illustrate the interface of FIG. 37C where the expandable member portion of the interface incorporates a thickened section 35 and additional structure associated with the electrode assembly 105 are also incorporated. The interface of FIGS. 39A-39C has particular advantage when presenting electrodes on the distal surface of the electrode assembly 105 as all portions of the shaft to which the expandable member 34 is interfaced reside proximal to the distal end of the shafts on inflation or a portion of the expandable member 34 is substantially distal to the distal end of the assembly or the distal end of the shaft.

Cooling procedures, either by direct irrigation at or near the electrodes or circulating cooling fluids through the expandable structure, are especially useful when the target tissue is not at the surface to which the electrodes are in closest proximity, but deeper into the adjoining tissue. Cooling the expandable structure or the irrigation fluid can allow for higher energy delivery while protecting the tissue near or in contact with the expandable structure while still allowing damage to tissue further away from the electrode. One such embodiment which allows for irrigation is shown in FIG. 39A. The membrane 34 is attached to the outer shaft 57 at the proximal end and to inner shaft 134 at the distal end, the inner shaft 134 being of a smaller diameter than the shaft 57 allows for passage of saline 30 in between the two shafts. The ends of the membrane may be thickened sections 35. In this particular embodiment, the flex circuit 89 is affixed to the inner catheter 134 and the distal branches of the flex circuit 87 are affixed to the membrane 34. Passage of saline 30 or other irrigation fluid is allowed as the flex circuit is slotted in the transition region. A close-up of the construction of FIG. 39A is shown in FIG. 39B. The distal branches of the flex circuit 87 are attached to the outside of the membrane 34, so the transition from the attachment to the inner shaft 134 to attachment to the outer shaft 57 occurs at or near the membrane junction. This transition section will also contain the slotted features for saline passage. The membrane at this attachment point is not attached to the inner shaft 134 which allows the space necessary for saline 30 to flow through into the membrane and provide a cooling mechanism.

Figure 39C:
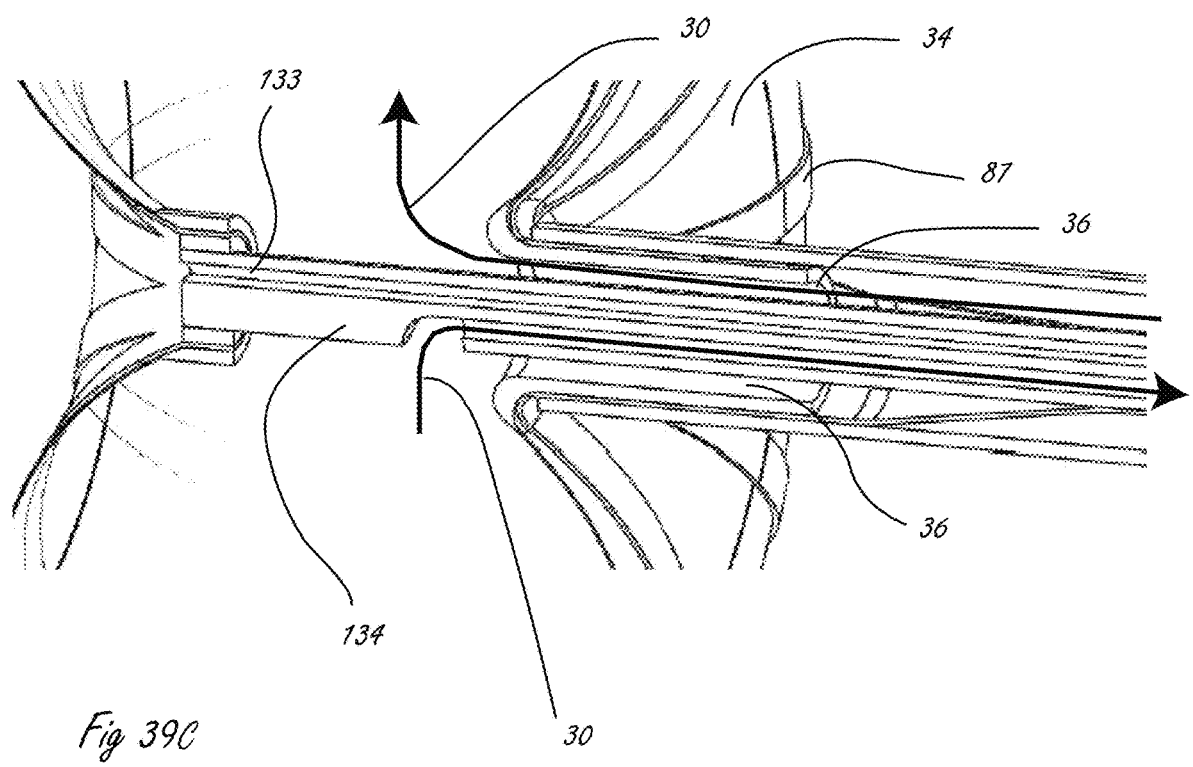

FIG. 39C shows an alternate embodiment which can be used both for the irrigation and for recirculation of a cooling fluid. This embodiment expands on the previously described embodiment in FIGS. 39A and 39B, by incorporating an inner shaft 134 with two lumens, one of which is used as a return for the cooling fluid. The membrane is inflated with saline 30 via the inflation lumen 36 and, saline 30 exits via the opening into the flow return lumen of the inner shaft 134. The other lumen in the inner shaft 134 is used as guide wire lumen 133. Inner shaft 134 and the guidewire lumen 133 may be separate entities of a multi-lumen catheter. Irrigation may also be incorporated with a circulating fluid cooling system by additional saline exit holes at the membrane as previously disclosed.

Figures 40A, 40B:
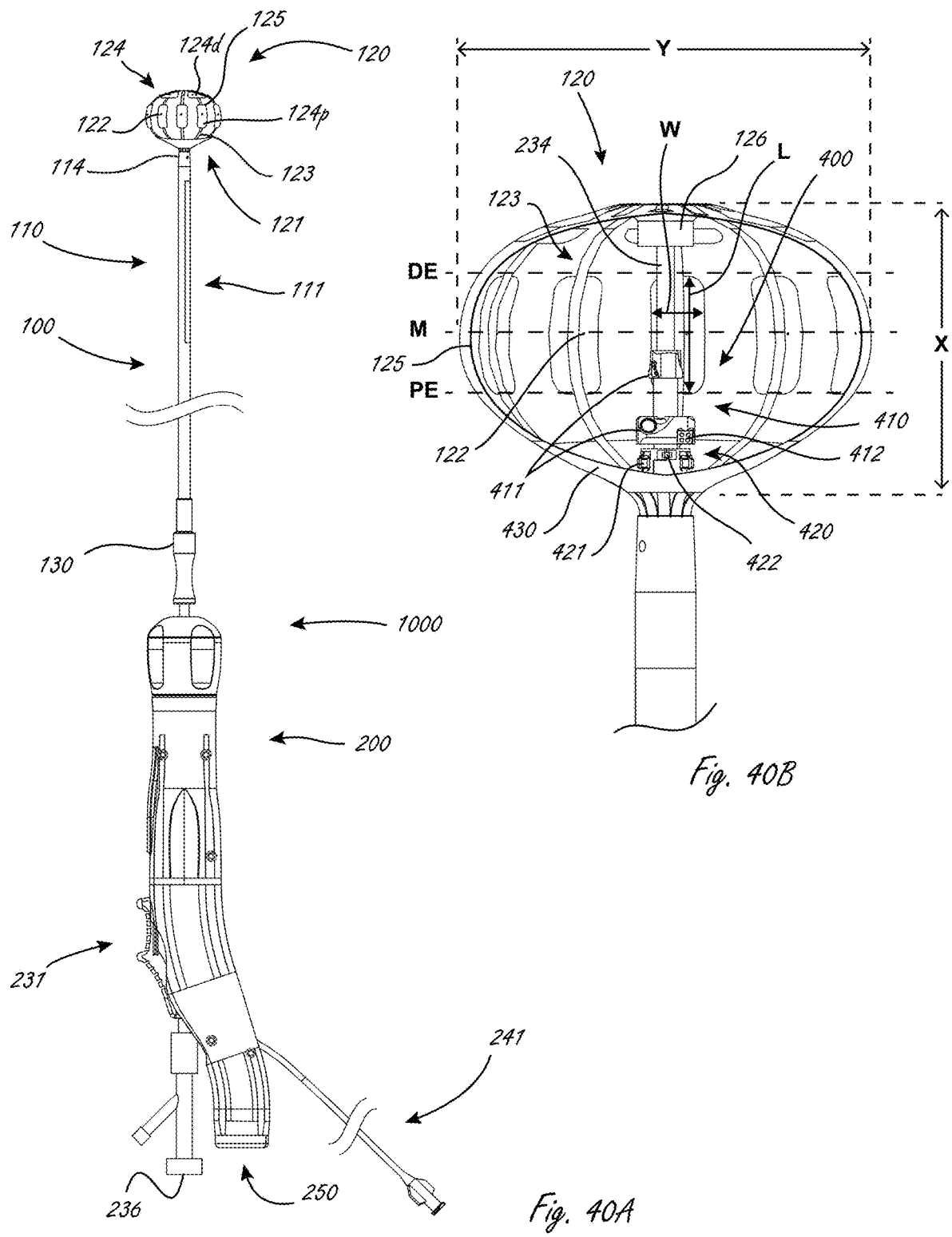

FIGS. 40A, 40B, and 40C illustrate an exemplary embodiment of an energy delivery device 1000, which includes endovascular diagnostic and/or interventional tool 120, catheter 100 adapted and configured to be steered in steerable section 111, and external device 200 configured and adapted to be manipulated by a user to control at least one aspect of catheter 100 and/or tool 120. FIG. 40A shows the entire device 1000 (the visible components of it) from the proximal end to the distal end. FIG. 40B illustrates a distal region of device 1000. FIG. 40B shows a cutaway of tool 120 to better show visualization system 400 therein. FIG. 40C illustrates a perspective view of the distal region.

In this embodiment, tool 120 is similar in some ways to the other expandable members described herein. Tool 120 includes an expandable balloon 125, one or more flexible circuits 123 carried by balloon 125, and a plurality of electrodes 124$p$ and 124$d$ carried directly or indirectly by balloon 125. Electrodes 124$d$ and electrodes 124$p$ include longitudinally aligned distal electrodes 124$d$ and longitudinally aligned proximal electrodes 124$p$. Longitudinally (or axially) aligned as used herein means that at least two things have distal ends that in are disposed in a plane and proximal ends that are disposed in a plane, the planes orthogonal to a longitudinal axis of the device. In other embodiments, only one of the distal ends and proximal ends may be disposed in a plane. In the embodiment in FIGS. 40A and 40B, electrodes 124$p$ have distal ends in plane DE, and proximal ends in plane PE. Tool 120, in the side view of FIG. 40B, a location "M" with the greatest linear dimension Y between outer surfaces of tool 120, the linear dimension measured orthogonal to the longitudinal axis of the device. For example, for a perfectly spherical tool, the location with the greatest linear dimension would be the equator of the sphere. The proximal electrodes 124$p$ are disposed external to the surface of the balloon, and extend over the location M. Proximal electrodes 124$p$ extend further distal to and proximal to the location M. Proximal electrodes 124p are thus considered to be disposed on both the proximal and distal portions of the tool 120. In this embodiment the proximal ends of electrodes 124p extend as far proximally from location M as distal ends of electrodes 124p extend distally from location M. Positioning at least some of the electrodes at this location can allow the tool to map and/or ablate tissue located further from the distal end of the tool than other embodiments herein. In this embodiment, electrodes 124p are symmetrical about location M. Proximal electrodes 124p have lengths (measured in the anterior-to-posterior direction) that are greater than their widths (widths being measured orthogonal to the longitudinal axis), wherein the length and width are measured when the electrodes are flat in a plane. The lengths can be at least twice as long as the widths, such as between two and four times as long as the widths. Proximal electrodes 124p have lengths that are at least twice as long (measured in the anterior-to-posterior direction) than the distal electrode, with the dimensions measured when the electrodes are flat in a plane. Distal electrodes 124d are generally distally facing in that they face further distally than radially outward. Proximal electrodes 124p are considered to be facing radially outward. Any of the disclosure above with respect to flexible circuit construction and components can be incorporated into this and any other embodiment herein.

In the embodiment in FIG. 40B (and optionally in FIG. 48 as well), the lengths of the rectangular proximal electrodes can be, in some embodiments, from 0.6 cm to 9 cm, such as 0.65 cm to 0.85 cm, such as 0.75 cm. The widths of the rectangular proximal electrodes can be, in some embodiments, from 0.25 cm to 0.45 cm, such as 0.3 cm to 0.4 cm, such as 0.35 cm. The lengths of the triangular distal electrodes can be, in some embodiments (when measured in the flat configuration of FIG. 48), from 0.6 cm to 0.7 cm, such as 0.65 cm. The widths of the triangular distal electrodes can be, in some embodiments (when measured in the flat configuration of FIG. 48), from 0.6 cm to 0.8 cm, such as 0.7 cm. For the triangular distal electrodes, the lengths of facing edges of the electrodes (the parallel edges) can be, in some embodiments from 0.35 cm to 0.55 cm, such as 0.43 cm.

FIG. 40C also illustrates how some flex circuit arms of tool 120 can include a plurality of sensing electrodes 419. Sensing electrodes 419 are disposed on alternating flex circuit arms around the balloon. In this embodiment sensing electrodes 419 are disposed on arms with only one ablation electrode (one of electrodes 124p), and are both distal to the ablation electrode. Mapping electrodes 419 are generally disposed between two adjacent distal electrodes 124d. In this embodiment, the flex circuit arms that include two ablation electrodes do not have any sensing electrodes, although in some uses electrodes 124p and/or 124d can be used as sensing electrodes. Sensing electrodes 419 are distally, or front, facing, which allows them to be more easily pushed up against tissue.

Tool 120 also includes a plurality of irrigation apertures 122, which in this embodiment extend through the electrodes and the balloon. In this embodiment, each electrode has an irrigation aperture 122 therethrough.

In some embodiments the greatest radial dimension "Y" (see FIG. 40B) of the tool 120 when expanded is from 0.5 to 3 inches, such as 0.5 to 2 inches, such as 0.5 to 1.5 inches, such as about 1 inch. In some embodiments the deployed axial length "X" of the tool 120 when expanded is from 0.25 to 2 inches, such as 0.25 to 1.5 inches, such as 0.25 to 1 inches, such as about 0.75 inches. Device 1000 also includes visualization system 400, at least a portion of which is disposed within the balloon. Visualization system 400 is identified within the balloon in FIG. 40B, and is shown by itself in FIGS. 41A-41D. Visualization system 400 includes a camera system 410, which includes distal camera subassembly 413 axially spaced apart from proximal camera subassembly 414 by axial distance 416. Each of the two camera subassemblies 413 and 414 include two lens assemblies (411) and sensors (412). Within each camera subassembly, each lens assembly is 180 degrees from the other lens assembly. The lens assemblies in each camera subassembly are 90 degrees from the lens assemblies in the other camera subassembly.

In a side view, the pairs of lenses in each subassembly 413 and 414 are axially aligned (in planes normal to the orthogonal to the longitudinal axis). The lenses in different subassemblies are axially spaced at fixed distances.

Visualization system 400 also includes housing 415, which houses the components of the camera system 410. Housing 415 can be machined and/or molded, for example, and the other components (e.g., lenses and sensors) can then be secured to housing 415.

Visualization system 400 also includes illumination assembly 420, which is disposed proximal to the camera system 410. The illumination assembly 420 includes a plurality of light sources (e.g., LEDs) 421 (only one light source is labeled for clarity) disposed around the illumination assembly 420. In some embodiments lighting flex circuit 423, which carries the electronics for the lighting assembly 420, is secured to the illumination assembly 420, as shown. Illumination assembly 420 is disposed such that light from the light sources is emitted at diffuser 430, as is described above.

Visualization system 400 also includes optional temperature sensor 422.

Housing 415 includes lumen 417 extending therethrough, through which guidewire lumen 234 (see FIG. 40B) extends. The proximal end of visualization system 400 is secured to a shaft of the device.

Figure 42A:
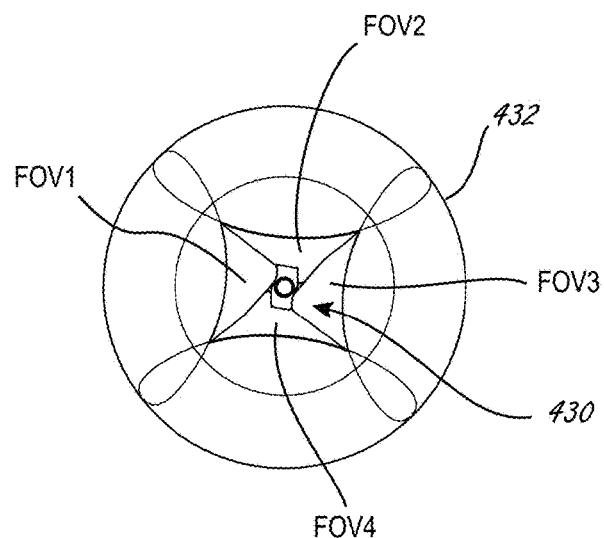
FIGS. 42A, 42B, 42C, and 42D illustrate exemplary fields of view of the cameras in the visualization system in FIGS. 41A, 41B, 41C, and 41D.
Figure 42B:
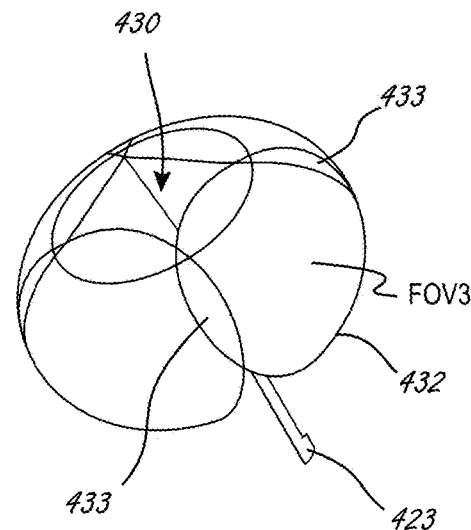

FIGS. 42A-42D illustrate fields of view as conical volumes truncated at the surface of balloon 125 for the four different cameras, each of which has a lens. FIG. 42A is a distal end view showing field of views FOV1-4 of the four different lenses, with the region 432 showing the field of views merged into a large field of view. FIG. 42B is a perspective view of FIG. 42A. The region 432 is the portion of the balloon within the field of views. The field of views do not include region 430 at the distal end of the balloon, through which the guidewire lumen passes. Region 430 can also be seen in FIG. 42A, which is somewhat rectangular because two lenses are axially spaced from the other two lenses. FIG. 42B illustrates overlap regions 433 in which adjacent fields of view overlap, which allows for a continuous 360 degree image to be obtained by integrating adjacent fields of view.

Figure 42C:
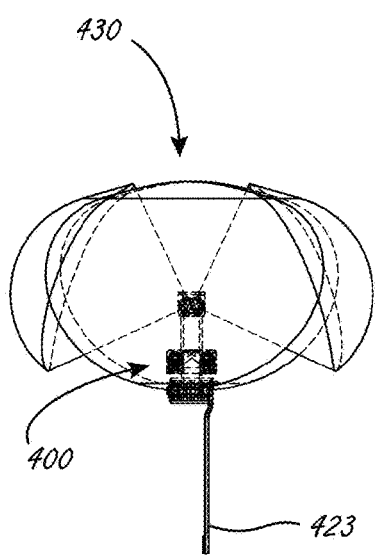
Figure 42D:
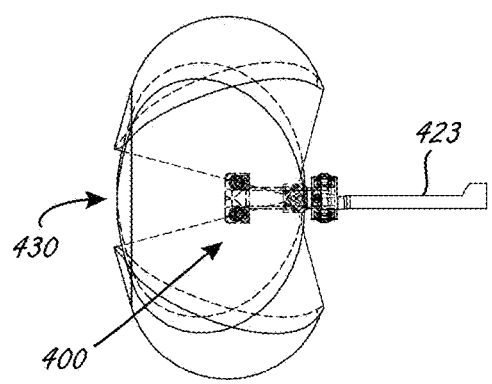

FIGS. 42C and 42D are side views showing the four fields of view.

Figure 43:
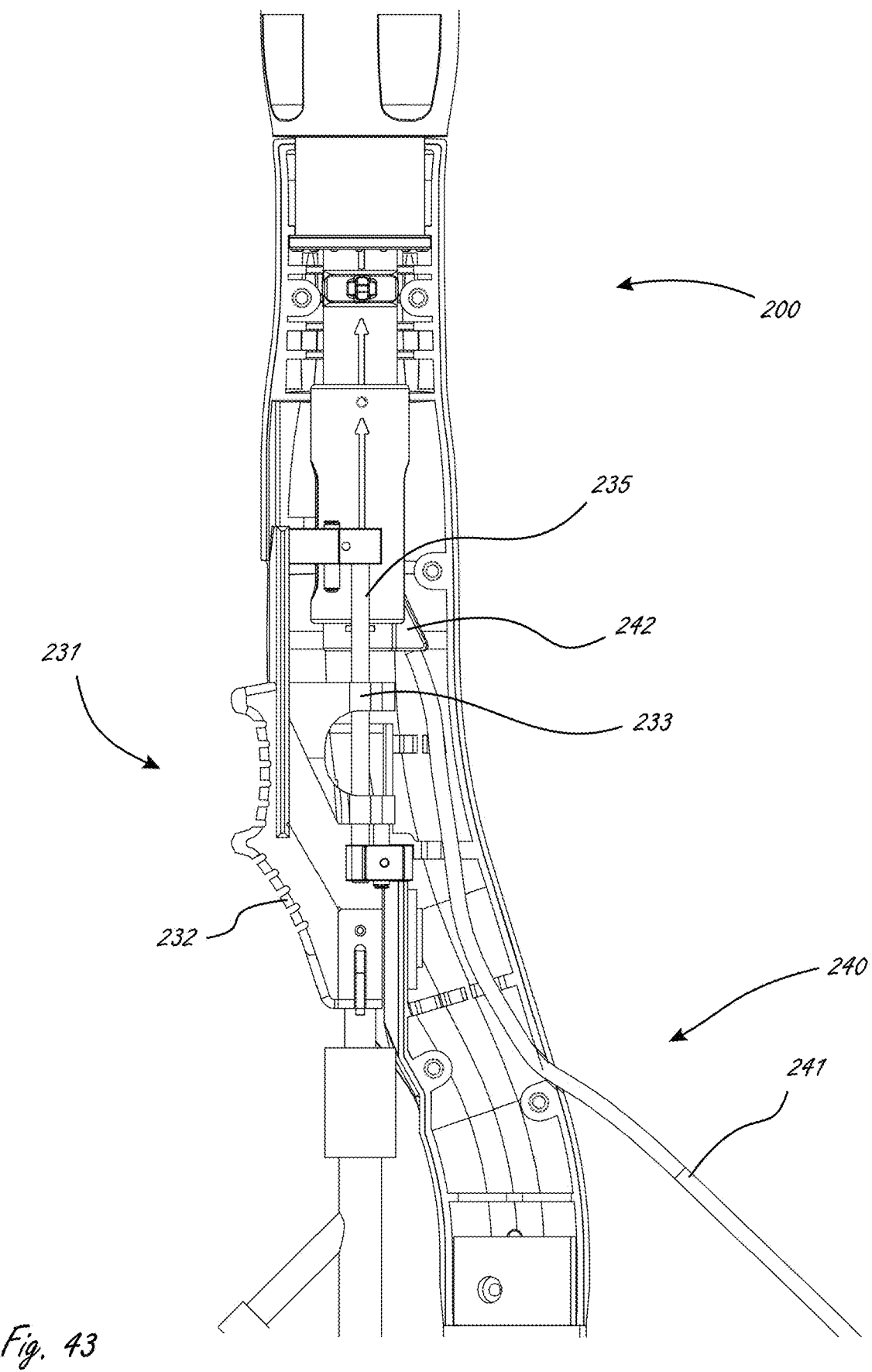
FIGS. 43 and 44 illustrate a merely exemplary external device that includes an actuator adapted to control the position of a distal region of a balloon.

The energy delivery device also includes external device 200 that can be in the form of a handle. In this embodiment in FIGS. 40A and 40B, device 200 includes an actuator 231 that is adapted to control deployment and/or sheathing of the expandable member. In this embodiment actuator 231 (see FIGS. 43 and 44) is adapted to move guidewire lumen 234 axially (forward and backwards) relative to the outer catheter structure 110. Because the distal end of the balloon is secured to (either directly or indirectly) the guidewire lumen, movement of the guidewire lumen (via actuator 231) moves the distal end of the balloon. Actuator 231 is also an example of an external actuator that can control movement of the guidewire lumen (and thus the balloons).

Figure 44:
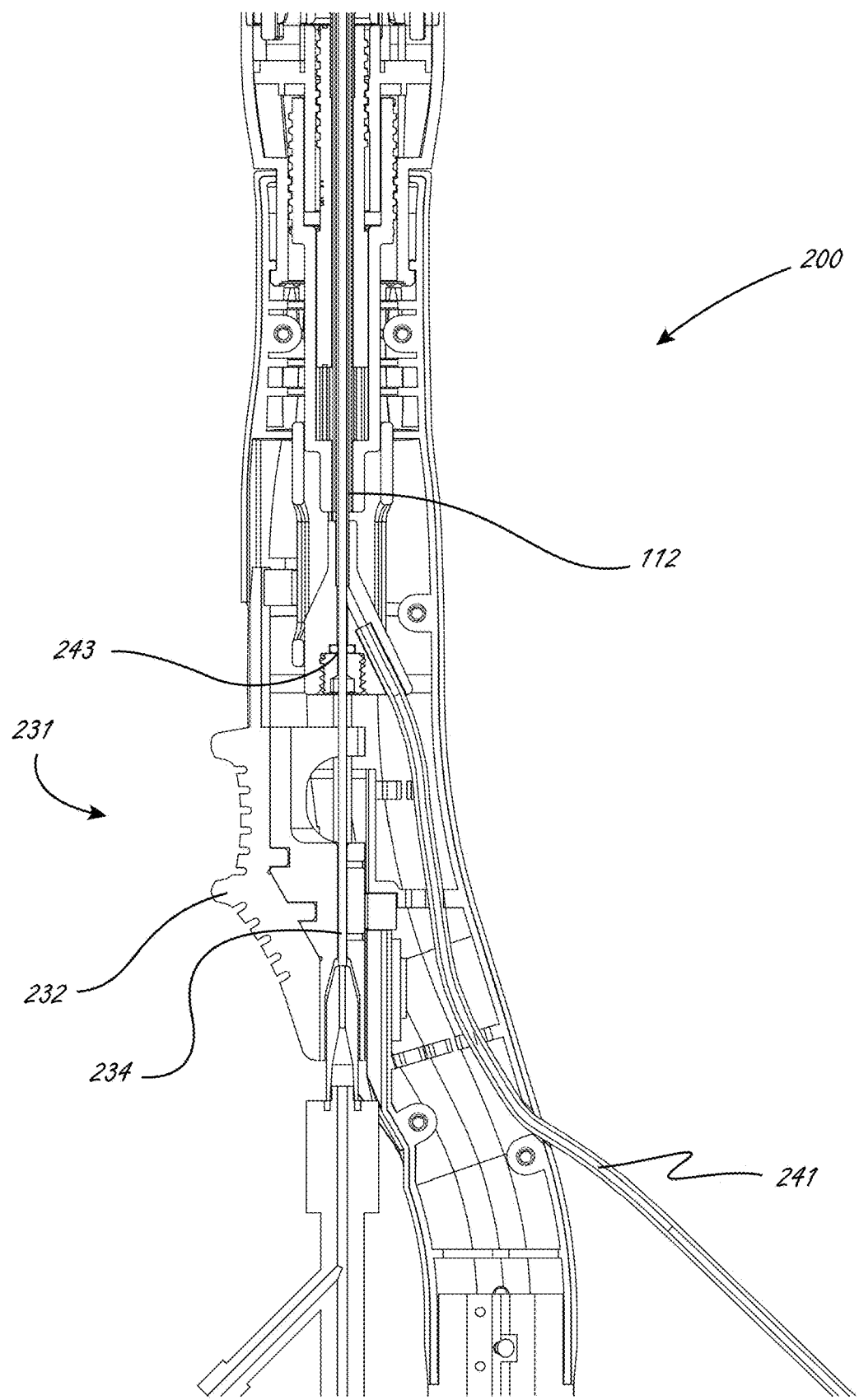

Actuator 231 can include an expandable member control grip 232, a slider 233 riding on one or more slides 235, the slider affixed to a guide wire lumen 234 (see FIG. 44). The external device also includes a hemostatic valve carried at its proximal end 236. In some embodiments the energy delivery device also comprises an irrigant supply system 240 comprising irrigation supply line 241, an irrigant manifold 242, a manifold comprising a guide wire lumen seal 243 through which a guide wire lumen passes.

The energy delivery device can also include an electrical interface 250 (see FIG. 40A) comprising at least an external interface to all cabling/wiring required to operate the on board electrical components.

In some embodiments the energy delivery device has the following characteristics: effective length: 70 cm; the steerable section a deflection angle: 0-120 deg, or −60 to +60; max actuation displacement: 30 mm; a maximum length change when steering is fully actuated: ~3 mm.

Figure 45A:
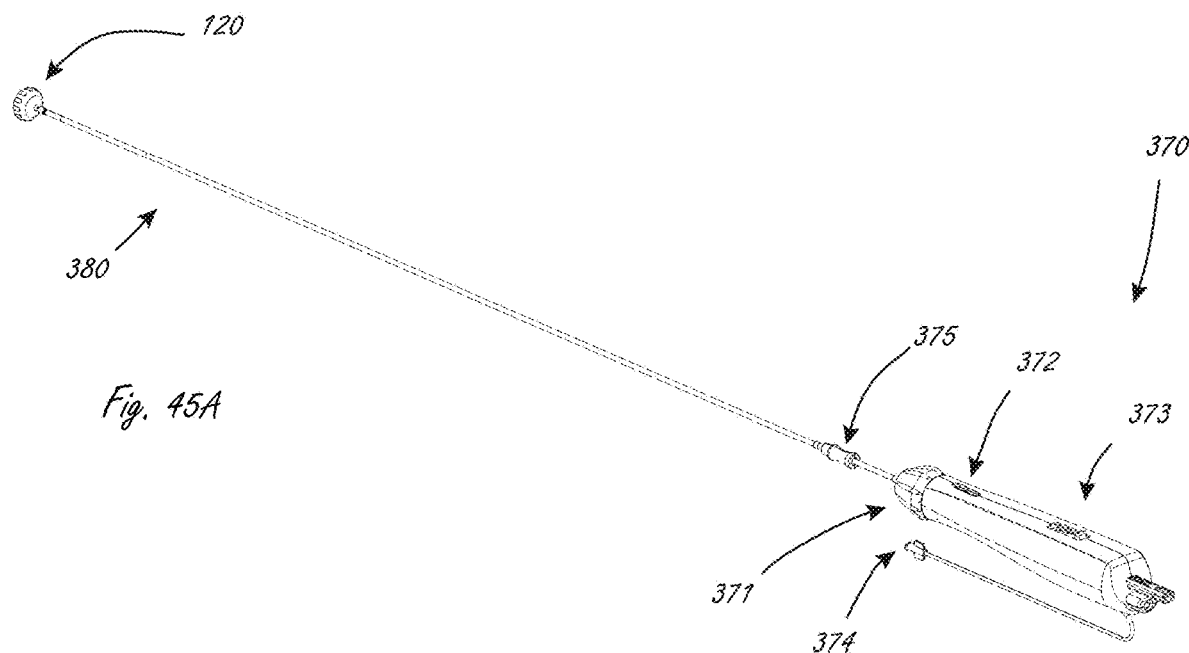
FIGS. 45A and 45B illustrate an exemplary therapeutic and/or diagnostic medical device.
Figure 45B:
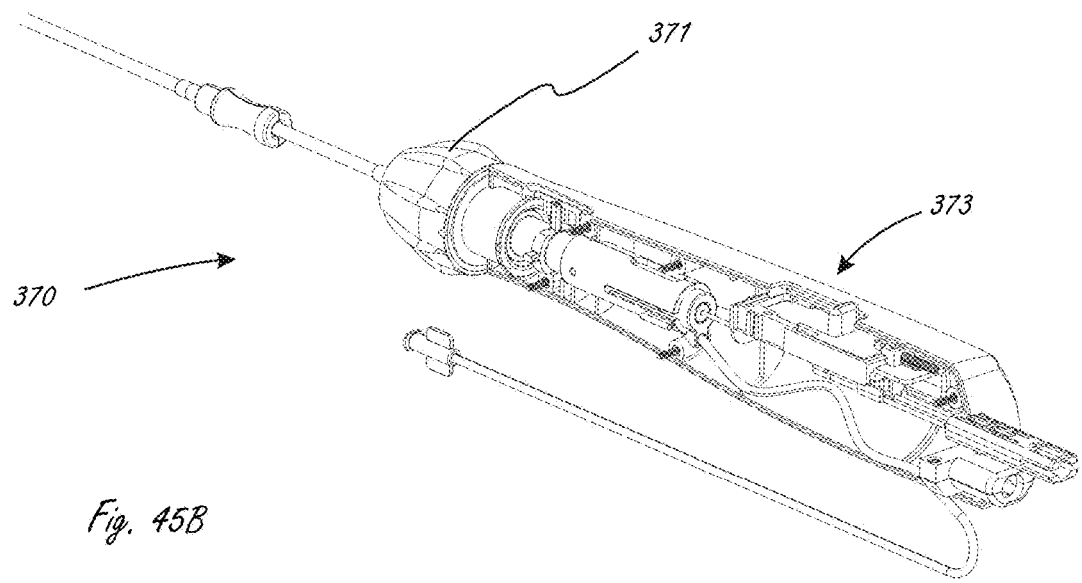
Figure 45C:
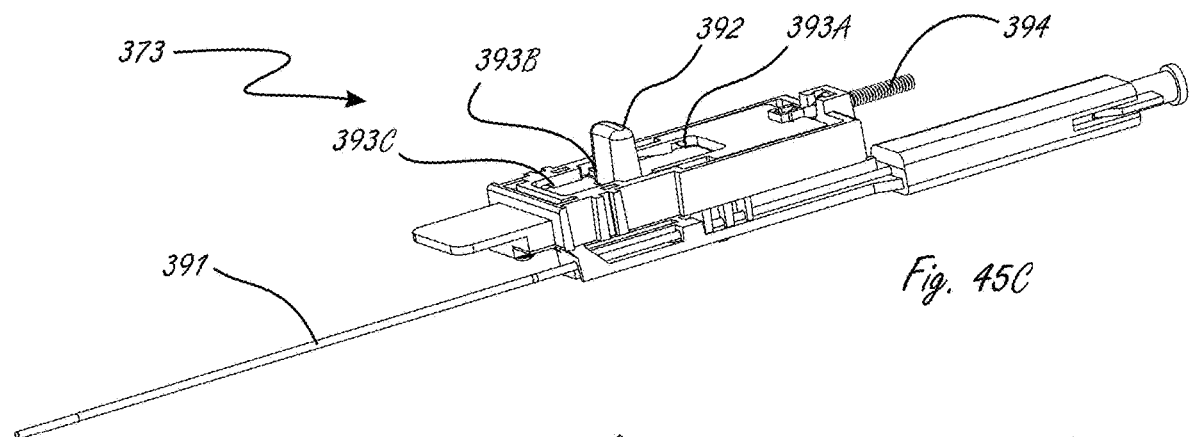
FIG. 45C illustrates an exemplary actuator of the external device in the medical device from FIGS. 45A and 45B.

FIGS. 45A-C illustrate an alternative handle 370 coupled to catheter and tool 380. FIG. 45B shows handle 370 with one half of the handle housing removed. Handle 370 includes actuator 371 that can be used to steer the steerable catheter as set forth above. Balloon deployment control 373 is in operable communication with the guidewire lumen. Movement of balloon deployment control 373 distally and proximally moves the guidewire lumen. Handle also includes steering indicator window 372, which allows a user to see a component inside the handle that indicates to what degree the catheter has been steered by actuating actuator 371.

FIG. 45C illustrates balloon deployment control 373 interfaced to guidewire lumen 391, which in turn is used to control the deployment and sheathing of the balloon. The mechanism comprises user interface slider 392, to be actuated by the user, which has three separate locking positions. The locking positions 393A, 393B, and 393C correspond to balloon full deployed, balloon partially deployed, and balloon configured for sheathing. The user interface slider 392 is in turn interfaced with the proximal portion of the guidewire lumen 391, the distal end of which is (directly or indirectly) attached to the distal end of the balloon. Position 393A is when slider 392 is pulled all the way back, which is when the guidewire lumen, and thus the distal end of the balloon will be in the most proximal position. Adjuster 394 is used at the time of manufacture to set a desired distance between positions 393B and 393C, corresponding to a desired length of the balloon when fully deployed/expanded.

Figure 46:
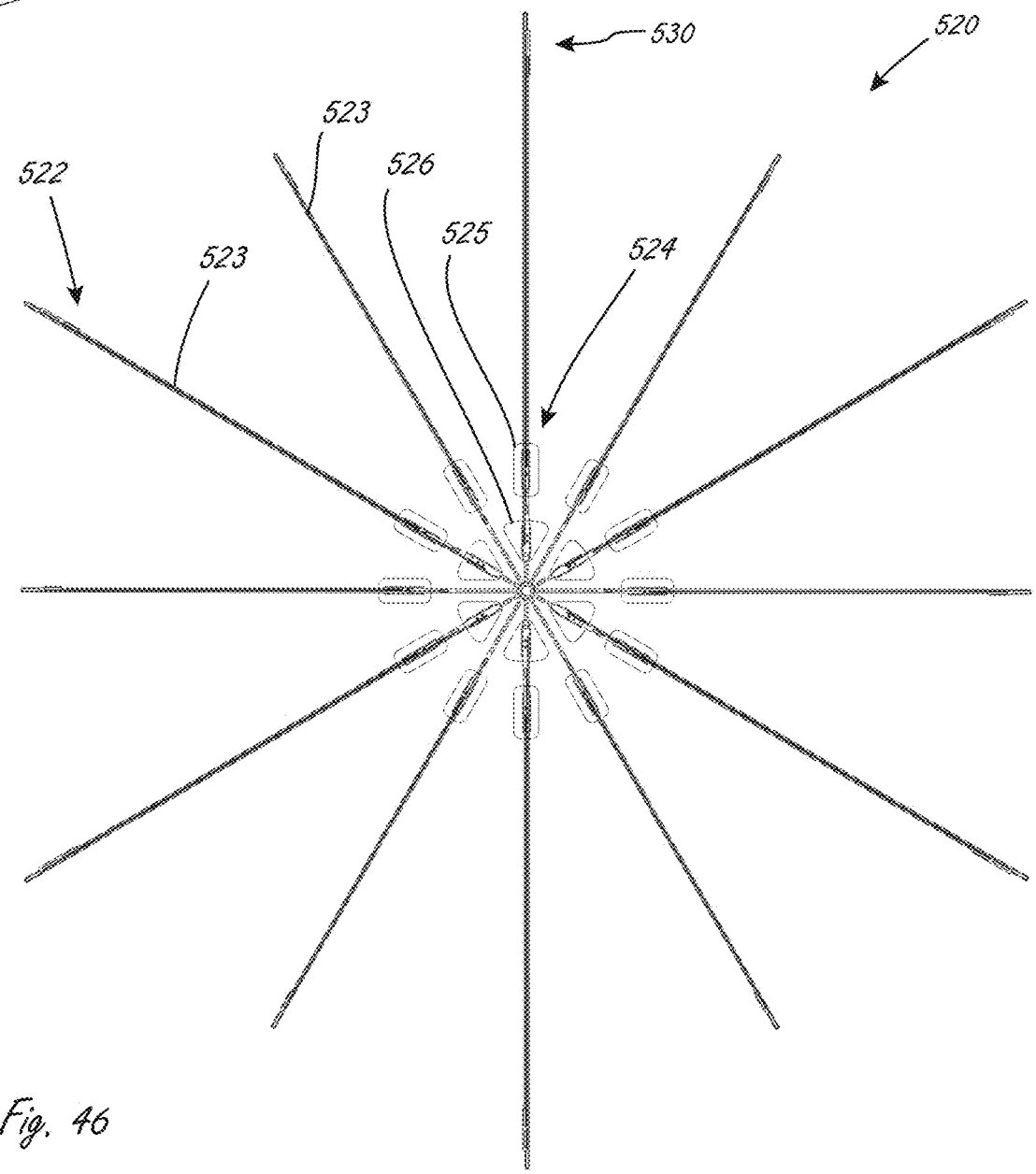
FIG. 46 illustrates an exemplary flex circuit and electrode design.

FIG. 46 shows a planar configuration of exemplary flexible circuit and electrode assembly 520, which is an example of a flexible circuit/electrode assembly that may be positioned on the balloon structure in FIGS. 40A and 40B. While in some manufacturing processes the electrodes are applied after the flexible circuit has already been applied to the balloon, the electrodes and the flexible circuit may be shown together herein in planar configurations without the balloon for clarity and to illustrate relative positions of components more easily. Assembly 520 includes flexible circuit 522 and a plurality of electrodes 524 that are disposed over at least a portion of flexible circuit 522. Flexible circuit 522 includes a plurality of elongate members, or arms, 523 (twelve are shown) secured together, optionally integrally, at a distal hub. Each of the elongate members 523 alone can also be considered a flexible circuit as that term is used herein. Plurality of electrodes 524 (which may be referred to herein as ablation electrodes) include a plurality of proximal electrodes 525 in an annular configuration and a plurality of distal electrodes 526 in an annular configuration. Twelve proximal electrodes 525 and six distal electrodes 526 are shown. The proximal and distal electrodes can be positioned on the balloon as is shown in FIGS. 40A and 40B, and aspects of the embodiment in FIGS. 40A and 40B can similarly be incorporated into the assembly 520 from FIG. 46. In this embodiment, proximal electrodes 525 have general rectangular configurations, and the distal electrodes 526 have general triangular configurations. Six of the flexible circuit fingers 523 have both proximal 525 and distal 526 electrodes secured over them, while six of the flexible circuit fingers have only proximal electrodes 525 secured over them. The fingers alternate in this manner around the flexible circuit, as shown in FIG. 46. All circuit fingers converge at central hub 537. In some alternative embodiments the traces and the electrodes are integral, such that the electrodes are not deposited on top of the conductive trace.

FIGS. 47A-47H show detailed views of portions of two adjacent elongate members 523 of the flexible circuit from FIG. 57, labelled 523a and 523b. FIG. 47A shows the distal regions of elongate members 523a and 523b, and FIGS. 47B and 47C show the proximal regions of elongate members 523a and 523b, respectively. FIG. 47D shows a detail of cross section A-A (shown in FIG. 47A) through elongate member 523b and a proximal electrode 525. In this embodiment, each of the elongate members 523 (which may also be referred to as "arms") generally includes, as can be seen in the cross section in FIG. 47E, substrate layer 532, one or more conductor layers 528, and one or more insulation layers 533. Substrate layer 532 can be adhered directly to the balloon 554 by an adhesive 559. Electrode 525 comprising an elastomeric conductor layer 560 is disposed over the substrate layer and one or more adhesive layers, the one or more insulation layers, and the one or more conductor layers. In some embodiments the elastomeric conductor layer will replace the adhesive layer. FIG. 47E is an even further enlarged subsection of section A-A. FIG. 47F illustrates cross section B-B, and FIG. 47G a further enlarged subsection of section B-B elucidating the various layers. FIG. 47H illustrates the use of adhesive 559 at section C-C where no elastomeric electrode is used. As will be discussed later, proximal electrode 525 is in electrical communication with conductor 528P at a region 529 where there is an absence of insulation layer between conductor 528P and proximal electrode 525. Region 529 can be formed by removing a region of previously applied insulation layer 533, such as by ablating a select region of insulation layer 533. Other techniques for creating the electrical connection can be used. Such ablation procedures may be carried out by laser ablation procedures which can make use of fiducial markings 561 and 562. In general, the insulation layer can be deposited over the entire structure defined by the substrate layer.

Elongate member or finger 523a includes a substrate layer, three discrete elongate conductor layers 528D, 528M, and 528P extending along the elongate member. Conductor layers 528D and 528P are in electrical communication with distal electrode 526 and proximal electrode 525 at regions 529D and 52P, respectively. The electrical communication regions 529D and 529P can be formed as described above with reference to FIG. 47D. The elongate arms 523 in this embodiment also include dedicated mapping electrodes 527, which are disposed distal to the proximal electrodes. Mapping electrodes 527 are regions of the flexible circuit at which the insulation layer 533 has been removed (or was never deposited), exposing a conductor and may or may not include a defined enlarged portion of conductor, a pad. A flexible electrode material is not disposed over conductor 528M in this embodiment, but in other embodiments mapping electrodes could have a separate flexible electrode material disposed over conductor 528M.

The distal electrodes have a generally triangular configuration, tapering towards the distal end. The proximal electrodes have a generally rectangular configuration.

The flexible circuits also include identification markers 534, which can be visualized and aid in identification the location of the electrodes. In this embodiment, markers 534 are disposed between the substrate layer and the balloon layer, adhered to the substrate. They are disposed such that they overlap with a distal region of the electrodes. Gold is an example of the material of markers that can enable visualization. The distance between, location, number, and arrangement of markers may be varied to identify each arm marked.

Elongate members 523 can optionally include one or more adhesive aperture 535, to improve adhesion of the substrate to the balloon.

The regions of the substrate layer that are under the proximal and distal electrodes include a plurality of projections 536 (also referred to as protrusions) that extend outward from the sides of the substrate. These projections improve the adhesion between the balloon and the substrate, as an adhesive 559 can occupy the spaces between the projections. In some embodiments, regions of the substrate that are not under the electrodes may include the projections.

A substrate can include one or more projections 536, and they can extend from one or both sides. The projections shown are regularly spaced apart, but need not be. The projections in this embodiment extend slightly in the distal direction (i.e., not orthogonally and not proximally) to reduce the risk of catching the projections on the delivery catheter during sheathing, but in other embodiments may extend in other direction. By saying that they extend in the distal direction, the projections are not orthogonal to the longitudinal axis of the arms. The projections can have other configurations as well.

The protrusions in this embodiment have the same configuration, but the configurations may vary. At least 50% of the plurality of protrusions have the same general configuration.

The protrusions can have a width 515 from 0.001 inch to 0.5 inches, such as from 0.001 inch to 0.25 inches, such as from 0.001 inch to 0.1 inch, such as from 0.001 inch to 0.01 inches, such as 0.001 inch to 0.007 inches (this is the shorter of the dimensions in the embodiment in FIG. 47A). The protrusions can have a length 517 from 0.001 inches to 0.05 inches, such as 0.001 inch to 0.025 inches, such as 0.001 inch to 0.01 inches, such as 0.001 inch to 0.005 inches, such as about 0.015 inches (the lengths are greater than the widths in the embodiment in FIG. 47A). One or more protrusions can be axially spaced apart by an axial distance 519 from 0.001 inches to 0.5 inches, such as 0.001 inch to 0.25 inches, such as 0.001 inch to 0.1 inches, such as 0.001 inch to 0.05 inches, such as about 0.010 inches. In this embodiment the substrate comprises at least 5 protrusions on a first side, and at least 5 protrusions on a second side. In this embodiment there are eighteen protrusions projection from each side of the substrate under the proximal electrodes, while there are sixteen protrusions projection from each side of the substrate under the distal electrodes. In some embodiments there are between 5 and 25 projections extending from one or both sides of the substrate. The interior angle between the protrusions and the longitudinal axis of the device can be less than 90 degrees, such as 85 degrees or less, such as 80 degrees or less, such as 75 degrees of less, such as 70 degrees or less, such as 65 degrees or less, such as about 60 degrees.

In this embodiment each elongate member 523 includes three conductors, each terminating at an interconnect pad 531 at a proximal end. In this embodiment conductor 528P terminates at pad 531P, conductor 528M terminates at pad 531M, and conductor 528D terminates at pad 531D. The pads 531D, M, and P are not aligned longitudinally (i.e., axially), to reduce the radial footprint of the proximal pad region. The pads are in electrical communication with additional conductors that carry the electrical signals to the proximal end of the energy delivery device. For example, the additional conductors can extend along a shaft of the energy delivery device.

As can be seen in FIG. 46, adjacent elongate member 523 have different lengths. For example, in FIG. 46, the elongate member 523 at the twelve o'clock position is longer than the elongate member 523 at the one o'clock position. The two o'clock position elongate member 523 is the same length as the twelve o'clock elongate member 523. Varying the elongate member lengths staggers the wider proximal ends of the elongate members so that they are not all aligned axially. The interconnects 530 (twelve in this embodiment) are spaced generally relatively close together on a shaft proximal to the end of the balloon (see the example configuration in FIG. 40B). By staggering the proximal ends of the elongate members, they are not spaced quite so closely and all of the proximal ends of the elongate members can more easily fit around the shaft to which they are mounted.

FIG. 46 is an example of a flexible circuit comprising first and second arms spaced from one another along at least a portion of their lengths, the first arm comprising a first conductive member and the second arm comprising a second conductive member, the first conductive member extending to a proximal region of the first arm, and the second conductive member extending to a proximal region of the second arm, and wherein the first arm has a proximal end that extends further proximally than a proximal end of the second arm. In this embodiment, the first arm is one of a plurality of first arms, and the second arm is one of a plurality of second arms, each of the plurality of first arms having a proximal end that extends further proximally than a proximal end of each of the plurality of second arms. When coupled to a balloon, the plurality of first arms and the plurality of second arms are carried by the balloon in an alternating arrangement around at least a portion of the balloon. In this embodiment, each of the plurality of first arms has a proximal end that extends to the same axial position along the device as each of the other proximal ends of the plurality of first arms.

Figure 48:
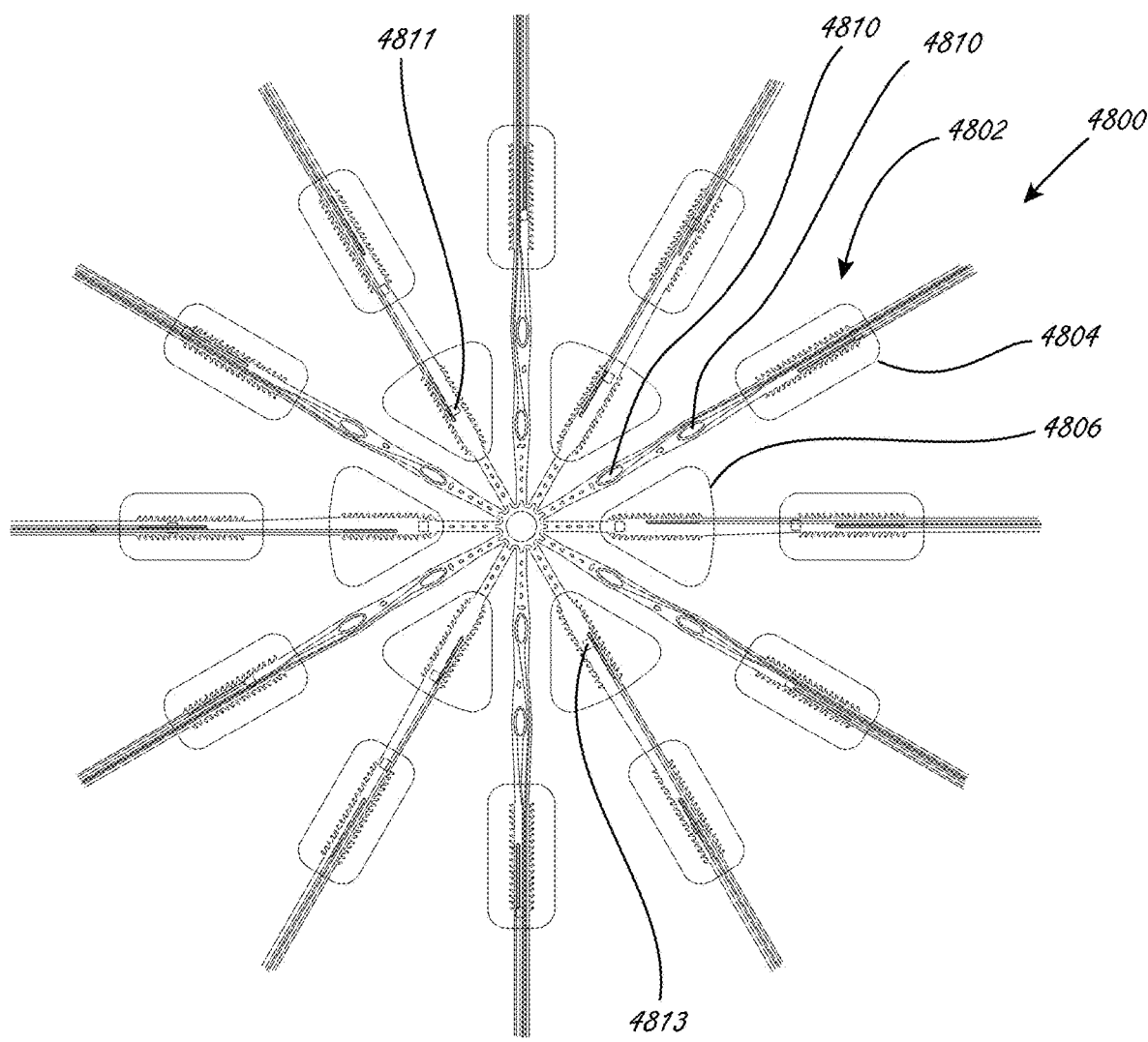
FIG. 48 illustrates an exemplary flex circuit and electrode design.

FIG. 48 illustrates an alternative planar configuration of exemplary flexible circuit and electrode assembly 4800, which is shown coupled to a balloon in FIG. 40C. Assembly 4800 is similar to that shown in FIGS. 46 and 47, but there are some differences. For example, assembly 4800 also includes a plurality of arms 4802, proximal electrodes 4804 and distal electrodes 4806. Some of the arms, however, include at least two sensing electrodes 4810 distal to an ablation electrode. Arms that are adjacent to those arms with two sensing electrodes do not have any mapping electrodes. Arms that only have two ablation electrodes and do not have mapping electrodes only have two conductive traces therein. Arms that have one ablation electrode and two sensing electrodes have three conductive traces thereon. Assembly 4800 can, in all other respects, include aspects of the assembly from FIGS. 46 and 47, such as the protrusions. The flex circuit can include electrode identifiers 4811 for the proximal electrodes, and electrode identifiers 4813 for the distal electrodes. The location of the electrode identifiers varies between electrodes, and this allows the user to know what electrode is being visualized when in use. The electrodes identifiers have varying positions along the length of the electrodes. Varying the locations and/or numbers of the identifiers on both the proximal and distal electrodes allows the user to know exactly which electrode is being visualized. The location of the electrode varies in a pattern, for both the proximal and distal electrodes.

Figures 49A, 49B:
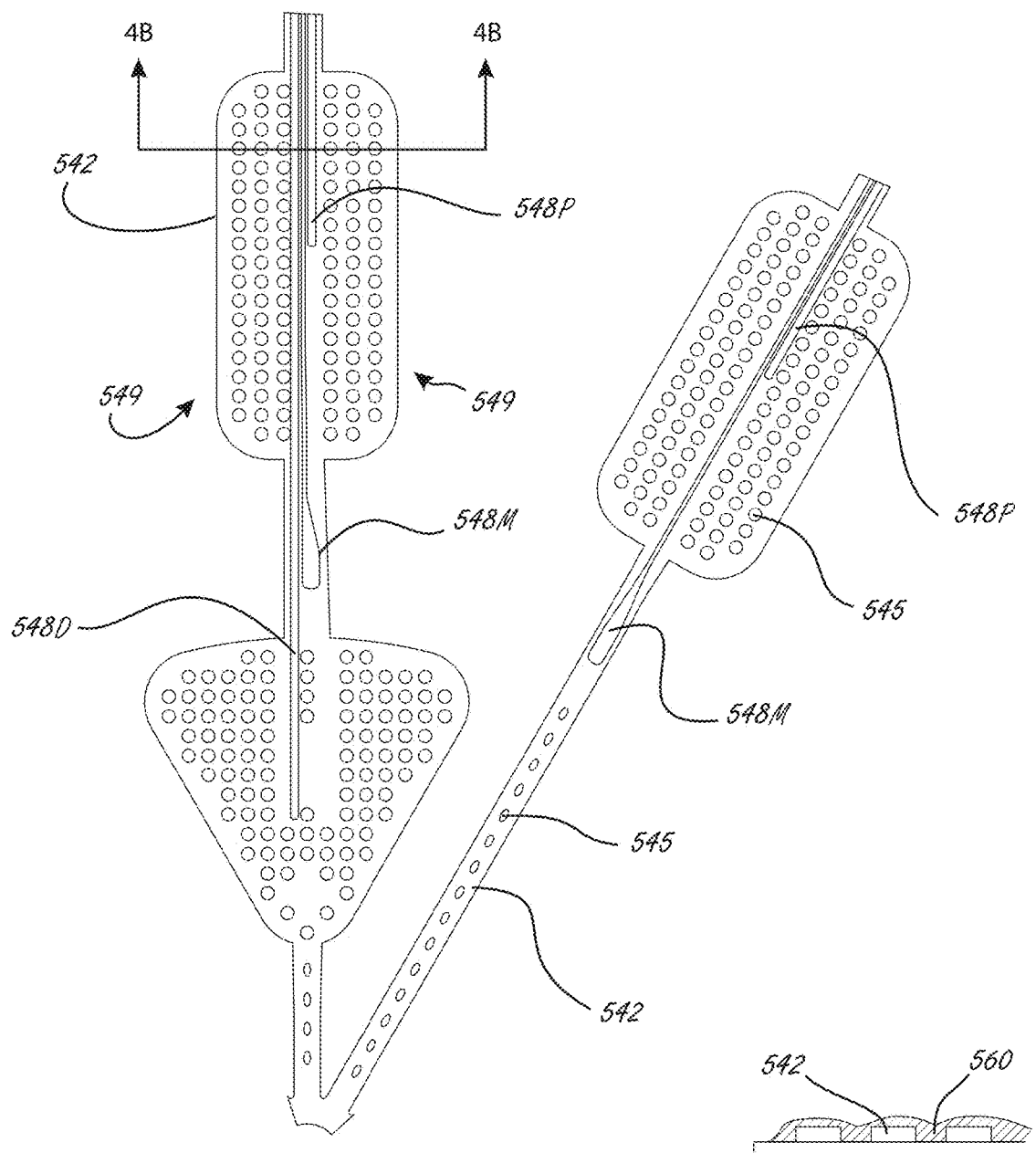
FIGS. 49A and 49B illustrate a portion of an exemplary flex circuit.

FIGS. 49A and 49B illustrates an alternative flexible circuit, showing only substrate 542 and conductors 548P, 548M, and 548D, similar to the embodiment above. Substrate 542 includes extensions 549 that extend radially to the sides from the elongate member. Substrate 542 includes a plurality of apertures 545 therein, which can enhance adhesion to the balloon, and provide for greater substrate flexibility. The mesh extensions can have the same or substantially the same configuration/shape of the proximal and distal flexible electrodes that will be disposed over the flex circuit. In this embodiment the proximal extensions have substantial rectangular shapes, and the distal extensions are generally triangularly shaped.

Figure 50A:
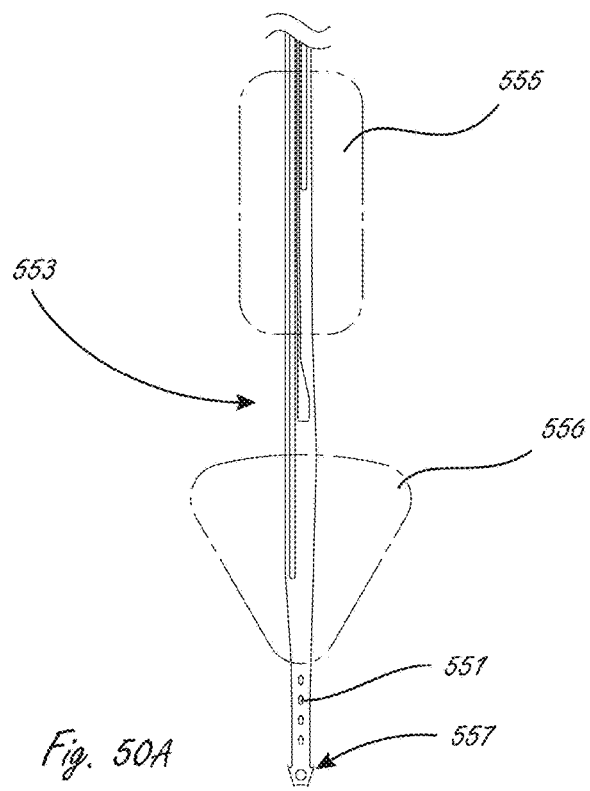
FIGS. 50A and 50B illustrate exemplary elongate members that are not integrally formed with other elongate members, or with a distal hub, but are each secured to a distal hub.
Figure 50B:
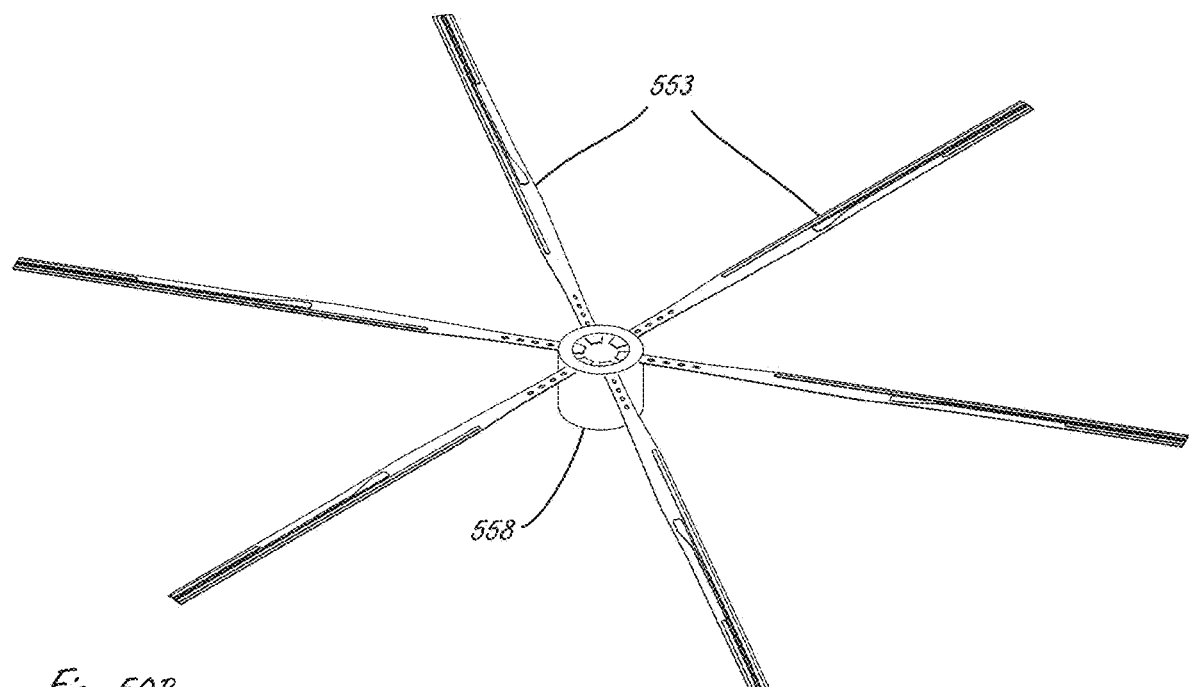

FIGS. 50A and 50B illustrates an exemplary elongate member 553 that is not integrally formed with other elongate members, or with a distal hub. In this embodiment all of the elongate members can be individually formed, and then secured together at a distal hub 558 at an interface. This can reduce the amount of wasted material during manufacturing since the elongate members don't need to be cut out of a single piece of starting material. Proximal electrode 555 and distal electrode 556 footprints are also shown. Glue holes 551 can also be formed in the substrate. Elongate member 553 has a hub interface 557 at its distal end. FIG. 50B shows elongate member 553 secured to distal hub 558. More elongate members would also be secured to hub 558. Elongate member 553 and hub 558 can be secured together using a variety of well-known techniques including sandwiching between elements of a multi-piece distal hub, or insert molding in a distal hub. Distal hub 558 secures the balloon to the guidewire shaft, as is disclosed in the embodiments above.

In alternate embodiments of a multi-piece flex-circuit array, each element may have a central hub with elongate members extending in both (e.g., opposite) directions. Each element can then be stacked with the central hub aligning with the guide wire lumen. For example, in the embodiment in FIG. 50B, the elongate elements that are 180 degrees apart could be part of the same element.

It may be advantageous during cardiac intervention to have available to the operator a compact-size version of any of the embodiments described herein. The system may provide the user with a one-shot style energy delivery device well suited for, but not limited to, single-point ablation touch-ups within the cardiac chamber, for example. This possible alternate embodiment of the disclosure may comprise a relatively small balloon in a compact design with a plurality of flexible circuits comprising elastomeric electrodes and optional mapping sensors extending proximally to distally along the exterior surface of the balloon and affixed to low-profile flexible circuits. The device can also include, within the expandable member, one or more imaging and illumination components similar to any of the systems described herein. The compact tool design may allow for greater maneuverability in small spaces and may offer a steerable portion integrated into an attached catheter.

FIGS. 51A, 51B, 52 and 53 illustrate exemplary embodiments of a steerable energy delivery device comprising flexible low-profile elastomeric electrodes and sensor assemblies with an onboard imaging system in a compact design.

FIG. 51A illustrates an exemplary distal portion of compact energy delivery device 5800, an alternate configuration to the embodiment presented in figured 40A and 40B, but without showing user control handle 200. Device 5800 includes a catheter 5810 configured to be steered in steerable section 5811, a compact-sized endovascular diagnostic and/or interventional tool 5820 adapted to be manipulated by a user via a control mechanism (not shown) to control at least one aspect of catheter 5810 and/or tool 5820.

FIG. 51B is a detailed perspective view of compact interventional tool 5820 located at the distal end region of device 5800. Compact tool 5820 comprises expandable balloon 5801 with a plurality of irrigation ports 5852 (only one is labeled), one or more elongate members 5822, and a plurality of elastomeric electrodes 5824. Exemplary diameters for compact balloon 5801 (and any compact balloons herein) can be in the range of 5 mm to 20 mm, such as 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, and 20. In some embodiments the balloon has a diameter between 8 mm and 20 mm, or 8 mm and 18 mm, or 8 mm and 15 mm. Elastomeric electrodes 5824 may be disposed axially and external to the surface of balloon 5801 where they overlay the elongate member 5822 comprising a substrate, at least one conductor, and optionally insulators. A plurality of these flexible circuits may extend from the distal end of balloon 5801 where they are secured at distal hub 5858. Elastomeric electrodes 5824 may contain openings as shown that allow mapping sensors 5827 (only one labeled) embedded in elongate member 5822 (such as in the manner shown above) to be exposed to the treatment area (e.g., heart tissue) thereby facilitating mapping sensor data to the user.

In this exemplary embodiment, the elastomeric electrodes 5824 are spaced 90 degrees apart around the balloon, and are longer than they are wide, extending over both the distal and proximal portions of the balloon.

Energy delivery device 5800 may also comprise a visualization system 5840 disposed proximally within the balloon. Visualization system 5840 can include camera system 5833 and a plurality of light sources 5835 (e.g., LEDs). Camera system 5833 may comprise a single camera or a plurality of cameras, and a single camera configuration is shown in FIG. 51B. The expandable member also includes a proximal diffuse reflector 5830, aspects and functionality of which are described above in previous embodiments. Suitable aspects of any of the embodiments above may be incorporated in this energy delivery device. The visualization system may alternatively be adapted and configured like any of the visualization systems herein.

In this embodiment the irrigation fluid (which inflates the balloon) passes through an irrigation lumen within the catheter and over the plurality of light sources 5835 (e.g., LEDs). The irrigation fluid can cool the light sources as is flows past the light sources and into the balloon. This provides an added benefit of preventing the light sources from overheating during use. In some embodiments the powering of the illumination elements is synchronized with the delivery of irrigation fluid such that illumination is only performed while irrigation is performed. In addition or other embodiments irrigation is served to illumination element temperature.

Figure 52:
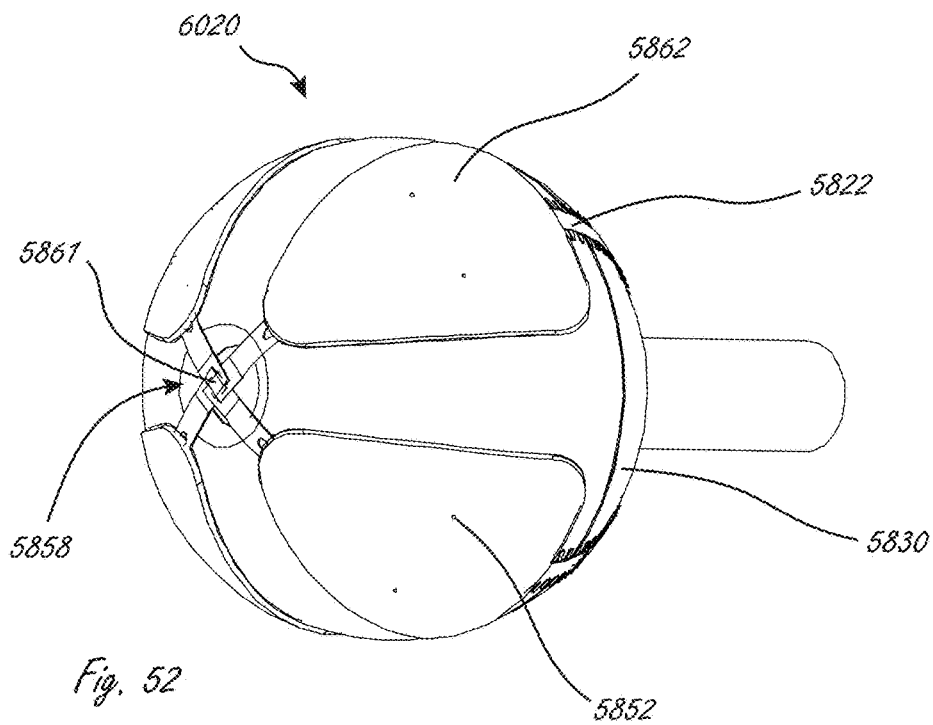
FIG. 52 illustrates an exemplary embodiment of a steerable energy delivery and/or diagnostic device comprising flexible low-profile electrodes and sensor assemblies with an onboard imaging system in a compact design.

FIG. 52 illustrates an exemplary embodiment of a compact tool 6020, a variation on device 5820, showing elastomeric electrodes 5862 with integrated irrigation holes 5852 (only one labeled) allowing the transmission of irrigant through both expandable member 5801 and electrodes 5862 during a procedure.

Figure 53:
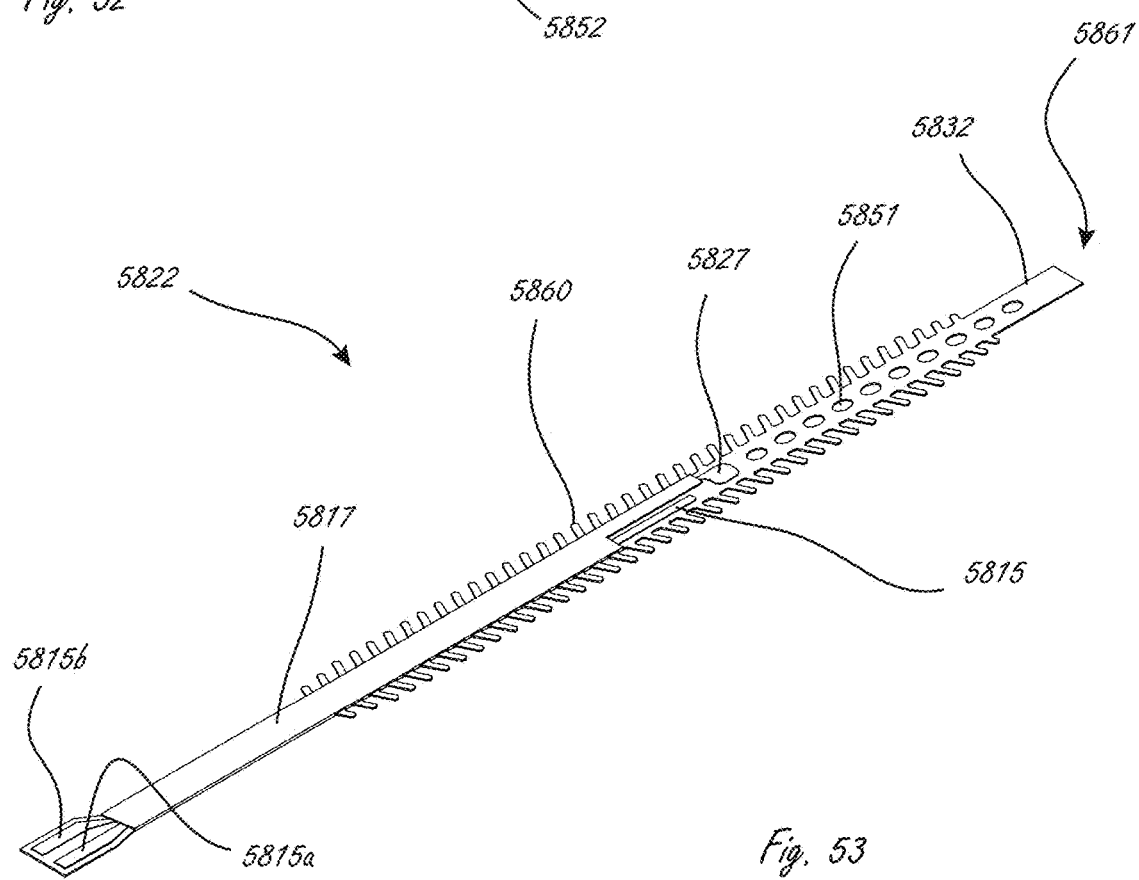
FIG. 53 illustrates an exemplary elongate member, or arm, of a flex circuit.

Compact tools 5820 and 6020 may comprise one or more elongate members 5822 shown in FIG. 53. The elongate members may be referred to herein as flexible circuits. Elongate member 5822 comprises substrate 5832, conductors 5815, insulator 5817, and optional mapping sensor 5827. Proximal is at the bottom left and distal is at the top right in FIG. 61. Distributed along the length of the substrate 5832 are a plurality of glue holes or adhesive apertures 5851 to aid in assembly and a plurality of projections comprised in a feathered edge 5860. Feathered edges 5860 and adhesive apertures improve the adhesion between the plurality of elongate members 5822 glued to the exterior surface of balloon 5801. Elongate members 5822 may also comprise mapping sensor 5827, this sensor may be of any variety of sensors as described herein. Sensor 5827 is interfaced to a control unit via conductor 5815b which runs parallel to electrode conductor 5815a. Both conductors are isolated beneath insulator 5817. Conductors 5815a and 5815b connect proximally from flexible circuit 5822 to the distal end of catheter 5810, thereby establishing conductive paths through the catheter to power sources, user interfaces and operator controls. The distal end 5861 of flexible circuit 5822 terminates at distal hub 5858 at the distal most point of expandable member 5801.

In the embodiments in FIGS. 51A, 51B, and 52, the balloons are generally spherical. "Generally spherical" refers to shapes that one skilled in the art would say are spherical.

Figure 54:
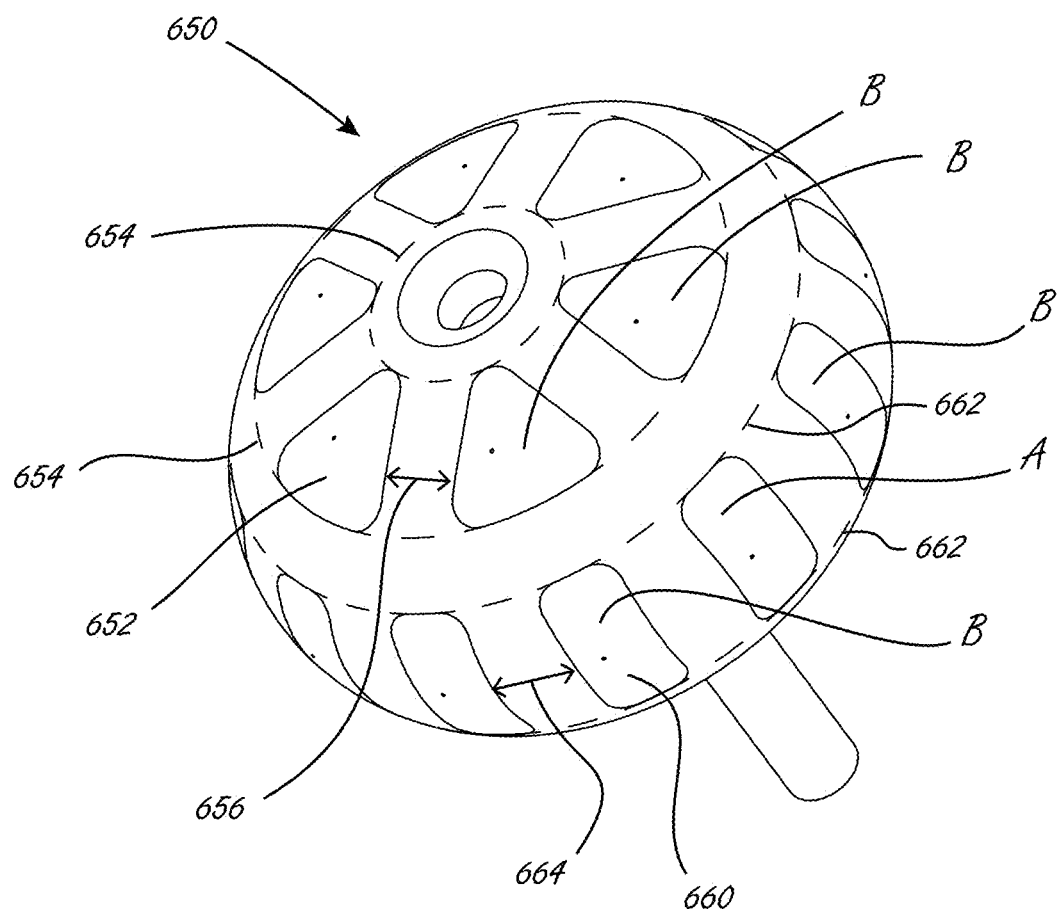
FIG. 54 illustrates an exemplary electrode pattern carried by a balloon, and exemplary spacing of the plurality of electrodes.

One of the benefits of some of the embodiments herein is that it is possible to get a complete burn in tissue between any adjacent electrodes, when operating in bipolar mode. This allows any two adjacent electrodes to be operated in bipolar mode and effectively ablate tissue between those electrodes. This creates a significant advantage when in use, as it increases the physician's options for ablating the desired tissue region. FIG. 54 illustrates an exemplary working end of an ablation catheter, showing only the location of electrodes relative to the balloon for clarity. The location and configuration of the electrodes in FIG. 54 is generally the same as in FIGS. 40A and 40B. "Adjacent" electrodes in this context refers to, for a particular electrode, the closest electrodes surrounding the particular electrode. For electrode "A" in FIG. 54, the adjacent electrodes are electrodes "B."

One of the aspects of the device that allows complete burns to be reliably created between adjacent electrodes is the power density of the device when in use. "Power density" as used herein refers to power per area, either with respect to surface area of one or more electrodes, or surface area of one or more electrodes and surface area of the balloon in between adjacent electrodes.

The disclosure below provides a quantitative assessment for power density in an exemplary use of the device shown in FIGS. 40A and 40B. In the description below, inner electrode area is referred to as "EI." "Outer electrode area" is referred to as "EO." "Inner space area" is referred to as "AI." "Outer space area" is referred to as "AO." "Bipolar set area" is referred to as "BPX." "Area total" is referred as to "Areatotal_X." "Power" is referred to as "Ptotal_X."

FIG. 54 illustrates, for ablation member 650, inner electrodes 652 (also referred to herein as distal electrodes), outer electrodes 660, inner electrode boundaries 654, inner electrode spacing 656, outer electrode boundaries 662, and outer electrode spacing 664.

In an exemplary method of use, the power delivered per electrode for full electrode contact was 8 W, and the power delivered per electrode for partial electrode contact was 10 W. Table 2 below illustrates power densities calculated based on surface areas of the inner electrodes 652 being 0.272 cm2, outer electrodes 660 having surface areas of 0.273 cm2, spacing area 656 between inner electrodes to be 0.221 cm2, spacing area 664 between outer electrodes to be 0.288 cm2. Power density is calculated as power/area.

The thickness of the atrial wall is about 1 mm to 10 mm, generally 1 mm to 3 mm. The average power density across the thickness of the heart can thus be calculated using any of the powers described herein and the area that defined by the heart thickness and the width of the tissue through which the energy is passing. The width of the tissue through which the energy is passing is generally the same as the length of the electrode, or the length of electrode sides that are facing each other, any of which described herein can be used to calculate the power densities.

TABLE 2

| Feature | Area (cm^2) | Power max density full contact (W/cm^2) | Power max density partial contact (W/cm^2) |
| --- | --- | --- | --- |
| Inner electrode | .27 | 29 | 37 |
| Outer electrode | .27 | 29 | 37 |
| Inner space | .22 | | |
| Outer space | .29 | | |
| Bipolar inner set | .77 | 10 | 13 |
| Bipolar outer set | .83 | 13 | 12 |
| Total inner set | 3.0 | 16 | 20 |
| Total outer set | 6.7 | 14 | 18 |

Table 3 and the analysis below illustrates some alternative devices, illustrating how devices with smaller electrode areas results in much higher power densities that than when the current device is used with somewhat similar power inputs. Using the data from Table 3, the device labeled "4 mm Tip" has a power density of about 90 W/cm2 when the power input is 30 W. The PVAC devices has a power density of about 147 W/cm2 when a max 10 W power is used. The MASC and MAAC have power densities of about 220 W/cm2 when a max 10 W power is used.

TABLE 3

| Electrode Surface Area | 33.7 mm² | 13.64 mm² | 9.09 mm² |
| --- | --- | --- | --- |
| Power Input | 30 W | Max 10 W | Max 10 W |
| Current Density | 0.016 A/mm² | 0.015 A/mm² | 0.018 A/mm² |

The disclosure provides methods of use that include power densities of less than about 40 W/cm2, when calculated based on the surface area of a particular electrode, and when there is full contact between the electrode and tissue. The disclosure provides methods of use that include power densities of less than about 25 W/cm2, when calculated based on the surface area spanning two electrodes and the spacing between them.

Figure 55:
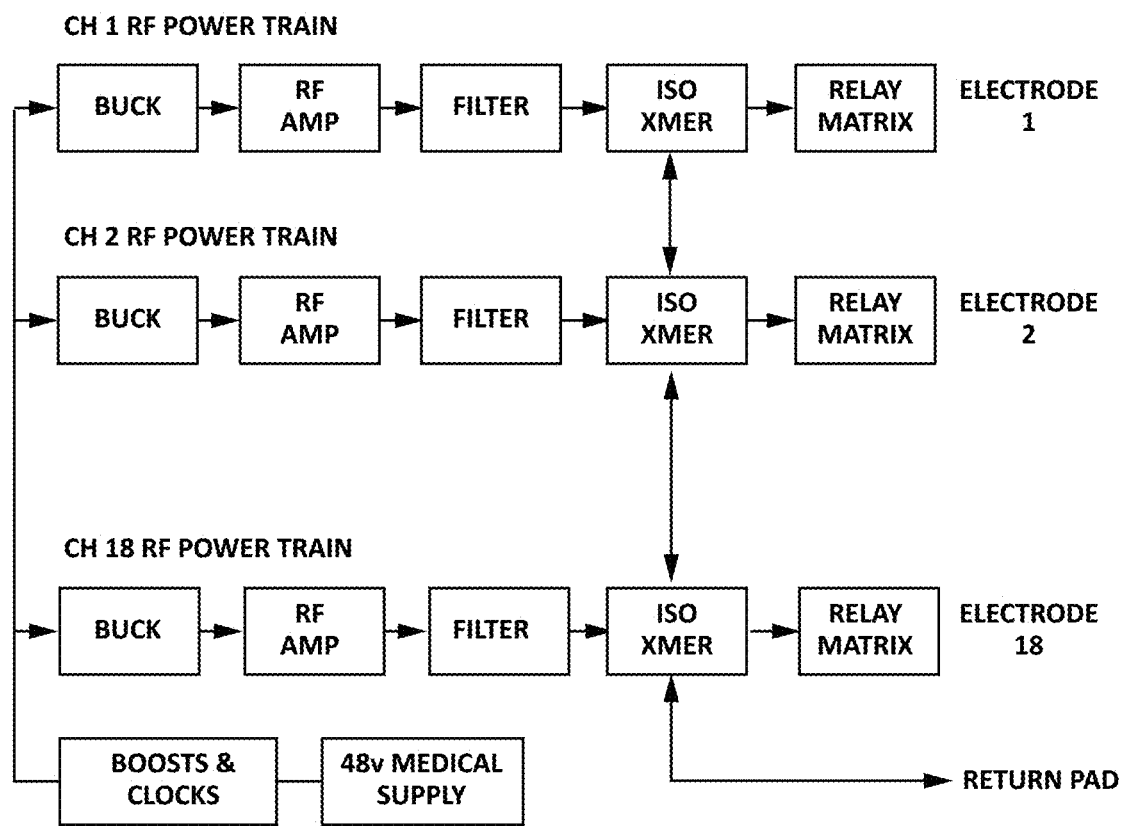
FIG. 55 illustrates an exemplary schematic for an exemplary power train, which can be used with any of the medical devices herein.

FIG. 55 illustrates an exemplary schematic for an exemplary power train. The boost block boosts the voltage out of the 48 volt medical grade supply to a voltage sufficient to deliver the desired power at the channel with the greatest impedance, typically 8 or 10 Watts. The bucks allow the adjustment of individual channel power. With respect to the filters, the signals to this point are square wave. The filters round out the corners to approach a sin wave. The relay matrix selects from local bi polar return, power pass through, or open circuit. The V/I/phase measure—feedback in PID loop, used to calculate electrode impedance, phase is used to control power by correcting for phase angle.

What is claimed is:

1. A cardiac tissue ablation device, comprising:
   an inflatable and flexible balloon disposed at a distal region of an elongate member, the balloon having a toroidal or spherical configuration when inflated;
   a flexible substrate branch adhered to an outer surface of the balloon along the length of the flexible substrate branch, the flexible substrate branch extending lengthwise from a proximal region of the balloon to a distal region of the balloon and extending widthwise from a first outer edge to a second outer edge;
   an adhesive for adhering the flexible substrate branch to the balloon, the adhesive disposed along and on top of a periphery of the flexible substrate branch in a region where an electrode is carried by the flexible substrate branch,
   wherein, at a distal location that is distal to where the electrode is carried by the flexible substrate branch, the adhesive is also disposed over an entire width of the flexible substrate branch from the first outer edge to the second outer edge;
   the electrode carried by the flexible substrate branch, the electrode flexible such that the electrode conforms to a curved configuration of the balloon when the balloon is inflated to the toroidal or spherical configuration; and
   a conductor in electrical communication with the electrode.

2. The device of claim 1, further comprising an elongate balloon actuator extending within the balloon, the elongate balloon actuator secured to a distal region of the balloon, wherein the elongate balloon actuator is axially movable relative to the elongate member.

3. The device of claim 2, wherein the elongate balloon actuator has a lumen therein sized to receive a guidewire.

4. The device of claim 1, further comprising a plurality of flexible substrate branches, of which the flexible substrate branch is one, each of the plurality of flexible substrate branches adhered to the outer surface of the balloon along the length of the flexible substrate branch, each of the flexible substrate branches extending lengthwise from the proximal region of the balloon to the distal region of the balloon and extending widthwise from a first outer edge to a second outer edge, and each of the plurality of flexible substrate branches carrying the electrode; wherein the adhesive is disposed along and on top of a periphery of each of the plurality of flexible substrate branches in a region where the electrode is carried by the flexible substrate branch, and wherein, for each of the plurality of flexible substrate branches, at a distal location that is distal to where the electrode is carried by the flexible substrate branch, the adhesive is also disposed over an entire width of the flexible substrate branch from the first outer edge to the second outer edge, and wherein the flexible substrate branch, in the region where the electrode is carried by the flexible substrate branch, has a width that is greater than a width of the flexible substrate branch at the distal location.

5. The device of claim 4, wherein the plurality of flexible substrate branches each have distal ends that are each secured to an annular member disposed at the distal region of the balloon.

6. The device of claim 5, wherein the plurality of distal ends are not directly attached to each other, but are secured relative to one another by the annular member.

\* \* \* \* \*